(12) United States Patent
Terada et al.

(10) Patent No.: US 7,576,910 B2
(45) Date of Patent: Aug. 18, 2009

(54) MICROSCOPE AND SAMPLE OBSERVATION METHOD

(75) Inventors: Hirotoshi Terada, Hamamatsu (JP);
Ikuo Arata, Hamamatsu (JP);
Masaharu Tokiwa, Hamamatsu (JP);
Hiroshi Tanabe, Hamamatsu (JP);
Shigeru Sakamoto, Hamamatsu (JP);
Yoshio Isobe, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 11/979,592

(22) Filed: Nov. 6, 2007

(65) Prior Publication Data

US 2008/0074739 A1  Mar. 27, 2008

Related U.S. Application Data

(63) Continuation of application No. 11/333,550, filed on Jan. 18, 2006, now Pat. No. 7,312,921, which is a continuation-in-part of application No. 10/880,100, filed on Jun. 30, 2004, now Pat. No. 7,110,172.

(30) Foreign Application Priority Data

Feb. 27, 2004 (JP) .......................... P2004-053343
Jan. 19, 2005 (JP) .......................... P2005-012103

(51) Int. Cl.
*G02B 21/00* (2006.01)
(52) U.S. Cl. ....................... 359/383; 359/368
(58) Field of Classification Search ........................ None
See application file for complete search history.

(56) References Cited

U.S. PATENT DOCUMENTS 4,477,155 A  10/1984 Sato et al.

(Continued)

FOREIGN PATENT DOCUMENTS

EP  0 977 192 A1  2/2000

(Continued)

OTHER PUBLICATIONS

ISTFA 2003 "Photoemission and OBIRCH Analysis With Solid Immersion Lens (SIL)", ISTFA 2003, pp. 1-20.

(Continued)

*Primary Examiner*—Lee Fineman
(74) *Attorney, Agent, or Firm*—Drinker Biddle & Reath LLP

(57) ABSTRACT

For a semiconductor device S as an inspected object, there are provided an image acquisition part 1, an optical system 2 including an objective lens 20, and a solid immersion lens (SIL) 3 movable between an insertion position including an optical axis from the semiconductor device S to the objective lens 20 and a standby position off the optical axis. Then observation is carried out in two control modes consisting of a first mode in which the SIL 3 is located at the standby position and in which focusing and aberration correction are carried out based on a refractive index $n_0$ and a thickness $t_0$ of a substrate of the semiconductor device S, and a second mode in which the SIL 3 is located at the insertion position and in which focusing and aberration correction are carried out based on the refractive index $n_0$ and thickness $t_0$ of the substrate, and a refractive index $n_1$, a thickness $d_1$, and a radius of curvature $R_1$ of SIL 3. This provides a microscope and a sample observation method capable of readily performing observation of the sample necessary for an analysis of microstructure or the like of the semiconductor device.

8 Claims, 33 Drawing Sheets

U.S. PATENT DOCUMENTS

| | | |
|---|---|---|
| 5,004,307 A | 4/1991 | Kino et al. |
| 5,125,750 A | 6/1992 | Corle et al. |
| 5,208,648 A | 5/1993 | Batchelder et al. |
| 5,220,403 A | 6/1993 | Batchelder et al. |
| 5,422,498 A | 6/1995 | Nikawa et al. |
| 5,764,613 A | 6/1998 | Yamamoto et al. |
| 5,939,709 A | 8/1999 | Ghislain et al. |
| 5,940,545 A | 8/1999 | Kash et al. |
| 6,002,792 A | 12/1999 | Oguri et al. |
| 6,441,359 B1 | 8/2002 | Cozier et al. |
| 6,475,398 B2 | 11/2002 | Kitahata |
| 6,594,086 B1 | 7/2003 | Pakdaman et al. |
| 6,608,359 B2 | 8/2003 | Kitahata |
| 6,621,275 B2 | 9/2003 | Cotton et al. |
| 6,656,029 B2 | 12/2003 | Kitahata |
| 6,687,058 B1 | 2/2004 | Ippolito et al. |
| 6,961,672 B2 | 11/2005 | Kasapi |
| 2001/0053117 A1 | 12/2001 | Ichimura et al. |
| 2003/0202255 A1 | 10/2003 | Pakdaman et al. |
| 2003/0210057 A1 | 11/2003 | Cotton et al. |
| 2006/0109562 A1 | 5/2006 | Arata et al. |

FOREIGN PATENT DOCUMENTS

| | | |
|---|---|---|
| JP | 05-80247 | 4/1993 |
| JP | 05-157701 | 6/1993 |
| JP | 06-300824 | 10/1994 |
| JP | 7-18806 | 3/1995 |
| JP | 07-190946 | 7/1995 |
| JP | 10-150086 | 6/1998 |
| JP | 11-003534 | 1/1999 |
| JP | 2000-171611 A | 6/2000 |
| JP | 2001-023230 | 1/2001 |
| JP | 2001-034998 A | 2/2001 |
| JP | 2002-189000 | 7/2002 |
| JP | 2003-502705 | 1/2003 |
| JP | 2003-181672 A | 7/2003 |
| WO | WO 00/79313 | 12/2000 |
| WO | 2005/043210 A1 | 5/2005 |

OTHER PUBLICATIONS

ISTFA Nov. 2003, Conference Proceedings from the 29th International Symposium for Testing and Failure Analysis, pp. 325-329.

Fig.20
(a)
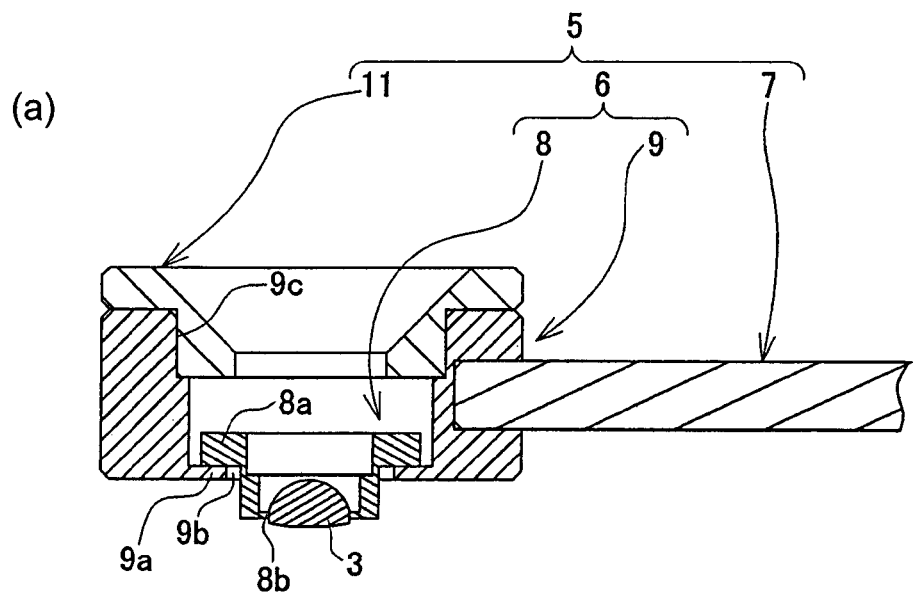
(b)
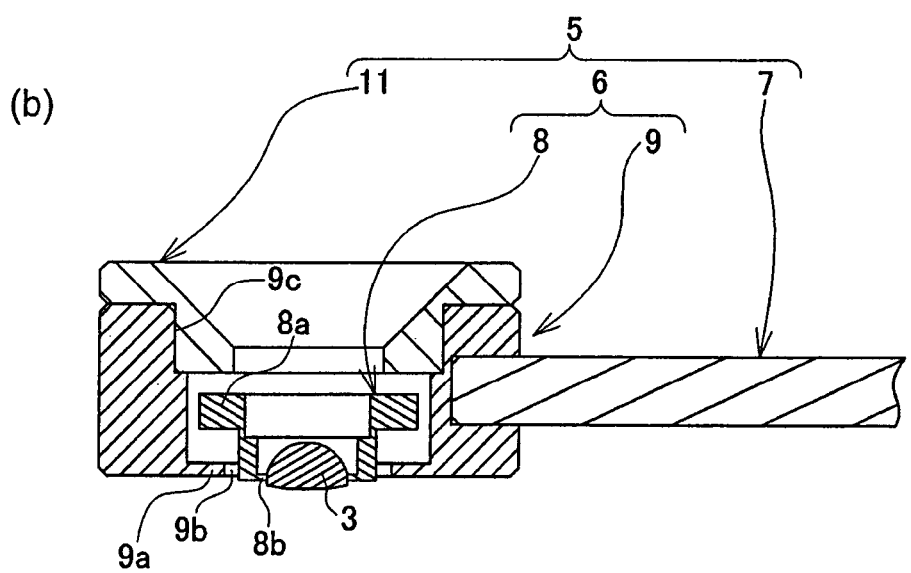

MICROSCOPE AND SAMPLE OBSERVATION METHOD

RELATED APPLICATION

This application is a continuation application of application Ser. No.11/333,550 filed on Jan. 18, 2006 now U.S. Pat. No. 7,312,921, which is a Continuation-In-Part of prior U.S. application Ser. No. 10/880,100 filed on Jun. 30, 2004, (now U.S. Pat. No. 7,110,172), each application being incorporated by reference herein in their entirety.

BACKGROUND OF THE INVENTION

1. Field of the Invention

The present invention relates to a microscope used for observing a sample such as a semiconductor device at a predetermined observation plane and through the sample, and a sample observation method.

2. Related Background Art

In recent years, many of semiconductor devices are being fabricated using face down bonding and flip chip bonding with a device surface (active circuit surface) at the bottom side of a substrate. In inspection of such semiconductor devices, it is sometimes difficult to expose the device surface of the substrate without disassembling a package, depending upon a type of the package and a mounting direction. Even in cases where a device surface of a substrate mounted not using the flip chip mounting can be exposed, but where semiconductor devices are highly integrated or multilayered, it is becoming hard to observe interconnections, devices, etc. in lower layers. Correspondingly, a method proposed is one of observing a semiconductor device through a substrate from the back side opposite the device surface.

The conventional known semiconductor inspection apparatus include an emission microscope (Japanese Patent Application Laid-Open No. H7-190946), an OBIRCH device (Japanese Patent Application Laid-Open No. H6-300824), a time-resolved emission microscope (Japanese Patent Application Laid-Open No. H10-150086), and so on. In observation using such microscopes, since silicon (Si) used as a material of the substrate, of the semiconductor device transmits near-infrared light, the observation is carried out using infrared light or the like. In recent years, however, the semiconductor devices as inspected objects are being miniaturized more and more, and it is becoming hard for the conventional inspection apparatus using visible light or infrared light, to analyze the microstructure, because of restrictions from the diffraction limit in the optical system.

For this reason, in a case where the microstructure of a semiconductor device is analyzed to detect an abnormal portion in a circuit pattern such as transistors and interconnections formed in the semiconductor device, an abnormality-existing range is first narrowed down to some extent by an inspection apparatus using visible light or infrared light. Then the narrowed-down range is further observed by a method with an observation apparatus such as an electron microscope with higher resolution to detect an abnormal portion in the semiconductor device.

SUMMARY OF THE INVENTION

The method of performing the observation in high resolution with the electron microscope after the inspection with light as described above has a problem that the inspection of semiconductor device requires a great deal of effort and time, for example, because of complicated preparation and installation of the semiconductor device as an inspected object.

On the other hand, a solid immersion lens (SIL) is known as a lens for enlarging an image of an observed object. The SIL is a lens of hemispherical shape, or of hyperhemispherical shape called a Weierstrass sphere, and is normally a compact lens element about 1 mm to few mm in size. When this SIL is placed in contact with the surface of the observed object, it can increase the numerical aperture NA and magnification and implement observation in high spatial resolution. However, inspection with the SIL has not been put to practical use yet in the field of the inspection of semiconductor devices, in view of its handling, observation control, and so on. This is also the case in observation of samples except for the semiconductor devices.

The present invention has been accomplished in order to solve the above problem, and an object of the invention is to provide a microscope capable of readily carrying out observation of a sample necessary for an analysis of microstructure of a semiconductor device and the like, and a sample observation method.

In order to achieve the above object, a microscope according to the present invention is a microscope for observing a sample at a predetermined observation plane, comprising: (1) an optical system comprising an objective lens and adapted to guide an image of the sample; (2) objective lens driving means for driving the objective lens to achieve focusing and aberration correction for the sample; (3) a solid immersion lens arranged at a position including an optical axis from the sample to the optical system; and (4) controlling means for controlling the objective lens driving means, wherein (5) the controlling means has a solid immersion lens mode, as a control mode, in which the focusing and aberration correction are carried out under a correction condition set based on a refractive index $n_0$ of the sample and a thickness $t_0$ of the sample up to the observation plane, and a refractive index $n_1$, a thickness $d_1$, and a radius of curvature $R_1$ of the solid immersion lens.

A sample observation method according to the present invention is a sample observation method of observing a sample at a predetermined observation plane and through an optical system comprising an objective lens, the sample observation method comprising: (a) a correction step of placing a solid immersion lens at an insertion position including an optical axis from the sample to the optical system and carrying out focusing and aberration correction under a correction condition set based on a refractive index $n_0$ of the sample and a thickness $t_0$ of the sample up to the observation plane, and a refractive index $n_1$, a thickness $d_1$, and a radius of curvature $R_1$ of the solid immersion lens; and (b) an enlarged image observation step (second image observation step) of observing an enlarged image of the sample in a state after completion of the focusing and aberration correction in the correction step.

The microscope and sample observation method described above are adapted for observation of a sample carried out through the sample and at a predetermined observation plane, such as inspection of a semiconductor device carried out from the back side through the substrate, and are configured to perform the observation of the sample by using the control mode (solid immersion lens mode) of carrying out the observation under the observation condition set in view of the optical parameters of the sample and the solid immersion lens in the presence of the solid immersion lens. This makes it feasible to suitably acquire the enlarged image in the presence of the solid immersion lens, and thus to readily perform the observation of the microstructure of the sample and the like.

A specific example of the observation of the sample is an example in which the sample is a semiconductor device and in which the semiconductor device is observed from its back side through a substrate. In this case, the aforementioned microscope is used as a semiconductor inspection apparatus, and implements easy accomplishment of inspection such as the analysis of microstructure of the semiconductor device. The optical system for guiding the image of the sample may be provided with image acquiring means for acquiring the image of the sample.

A solid immersion lens holder is preferably a solid immersion lens holder comprising: a base part to be attached to an objective lens; and a lens holding part provided with the base part, extending in a direction of an optical axis of the objective lens, and holding a solid immersion lens at an end portion thereof, wherein the lens holding part holds the solid immersion lens so that light emerging from the solid immersion lens to the base part side travels through a region outside the lens holding part and toward the base part, and wherein the base part has a light passing portion which transmits the light emerging from the solid immersion lens to the base part side, toward the objective lens.

Alternatively, a solid immersion lens holder is preferably a solid immersion lens holder for holding a solid immersion lens to be used in observation of an observation object placed in a recess of a sample holder, the solid immersion lens holder being attached to an objective lens, holding the solid immersion lens so as to avoid contact with a side wall of the recess during observation of a peripheral part of the observation object, and transmitting light emerging from the solid immersion lens to the objective lens side, toward the objective lens.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 20 is a figure including vertical sectional views showing (a) a state of the SIL holder at the standby position and (b) a state of the SIL holder at the insertion position, respectively.

DESCRIPTION OF THE PREFERRED EMBODIMENTS

Figure 1:
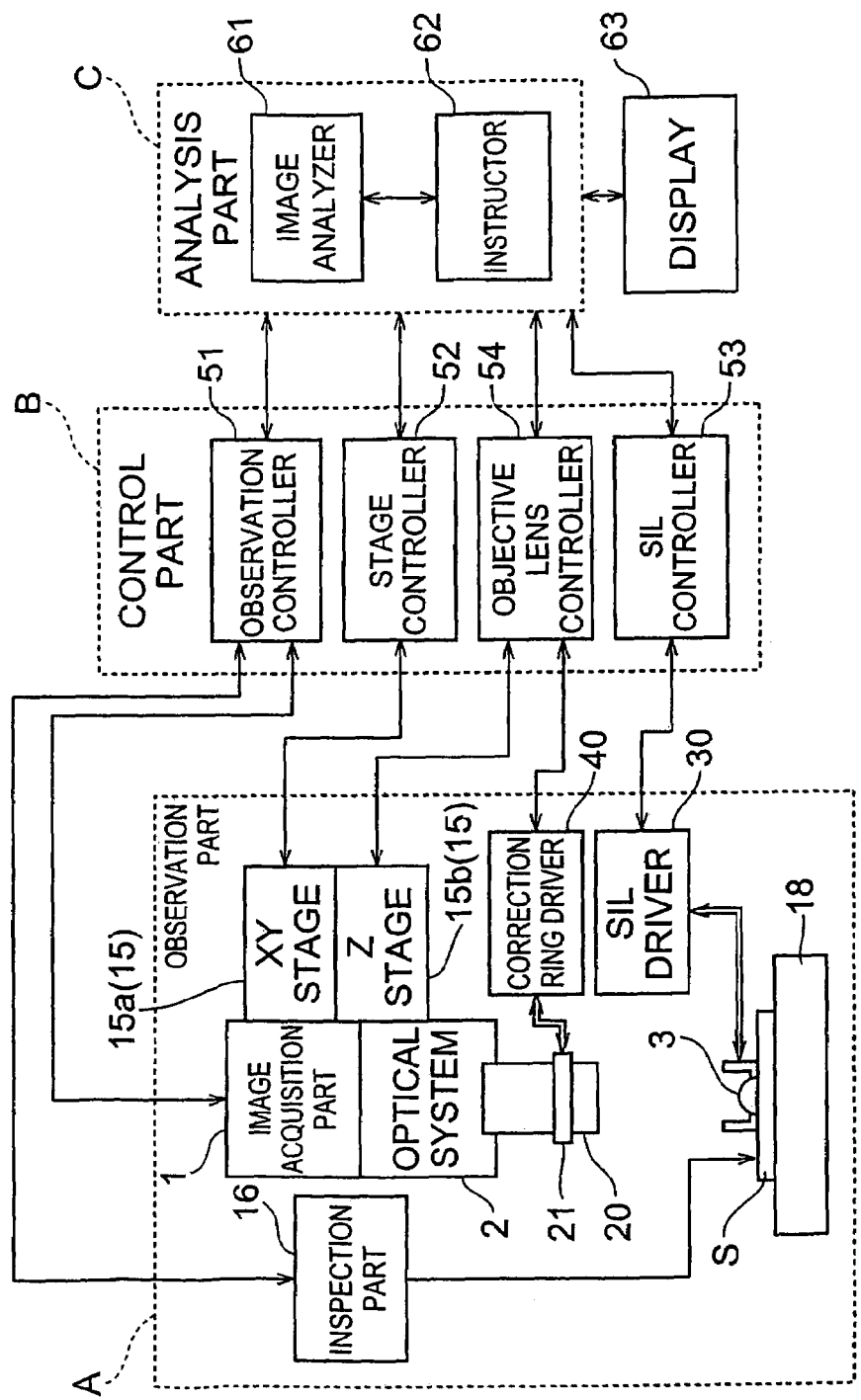
FIG. 1 is a block diagram schematically showing a configuration of an embodiment of the semiconductor inspection apparatus.

Preferred embodiments of the microscope and the sample observation method according to the present invention will be described below in detail with reference to the drawings. In the description of drawings the same elements will be denoted by the same reference symbols, without redundant description. It is also noted that dimensional ratios in the drawings do not always agree with those in the description.

First, a basic configuration of a semiconductor inspection apparatus being a microscope according to the present invention will be described. FIG. 1 is a block diagram schematically showing a configuration of an embodiment of the semiconductor inspection apparatus according to the present invention. The present apparatus is an inspection device adapted for a semiconductor device S, for example, in which a circuit pattern consisting of transistors, interconnections, etc. is formed on a device surface, as a sample of an inspected object (observed object), and is configured to set the device surface at an observation plane and observe to inspect the semiconductor device S through the substrate from the back side opposite the device surface. Here the microscope and sample observation method according to the present invention are applicable to any cases where the observation of the sample is carried out at the predetermined observation plane and through the sample, but the present invention will be described below mainly about the semiconductor inspection apparatus and inspection method as an application example thereof.

The semiconductor inspection apparatus in the present embodiment is comprised of an observation part A for observation of the semiconductor device S a control part B for control of operations of respective portions in the observation part A, and an analysis part C for processing, instructions, etc. necessary for the inspection of the semiconductor device S. The semiconductor device S as a sample of an inspected object, i.e., an observed object by the present inspection apparatus is mounted on a stage 18 in the observation part A so that a device surface as an observed surface thereof is placed on the stage 18 side and so that the back surface is up.

The observation part A has an image acquisition part 1 housed in a black box (not shown), an optical system 2, and a solid immersion lens (SIL) 3. The image acquisition part 1 is, for example, a means comprised of a photodetector, an image pickup device, or the like and adapted to acquire an image of the semiconductor device S. The optical system 2 for guiding an image of light from the semiconductor device S to the image acquisition part 1 is disposed between the image acquisition part 1, and the semiconductor device S mounted on the stage 18.

The optical system 2 is provided with an objective lens 20 at a predetermined position opposite to the semiconductor device S, to which the light from the semiconductor device S is incident. Light, for example, emerging from or reflected from the semiconductor device S is incident to the objective lens 20 and travels through the optical system 2 including the objective lens 20, to the image acquisition part 1. Then the image acquisition part 1 acquires the image of the semiconductor device S to be used in inspection.

The image acquisition part 1 and the optical system 2 are integrally constructed in a state in which their optical axes are coincident with each other. An XYZ stage 15 consisting of an XY stage 15a and a Z stage 15b is provided for these image acquisition part 1 and optical system 2. The XY stage 15a is used for moving the image acquisition part 1 and optical system 2 in the X-Y plane (horizontal plane) to set the observation position (inspection position) for the semiconductor device S. The Z stage 15b is used for moving the image acquisition part 1 and optical system 2 in the Z direction (vertical direction) to adjust the focal point relative to the semiconductor device S. This permits the Z stage 15b to function as a focusing means for changing the distance between the substrate of the semiconductor device S and the objective lens 20 of the optical system 2 to effect focusing in observation.

Figure 2:
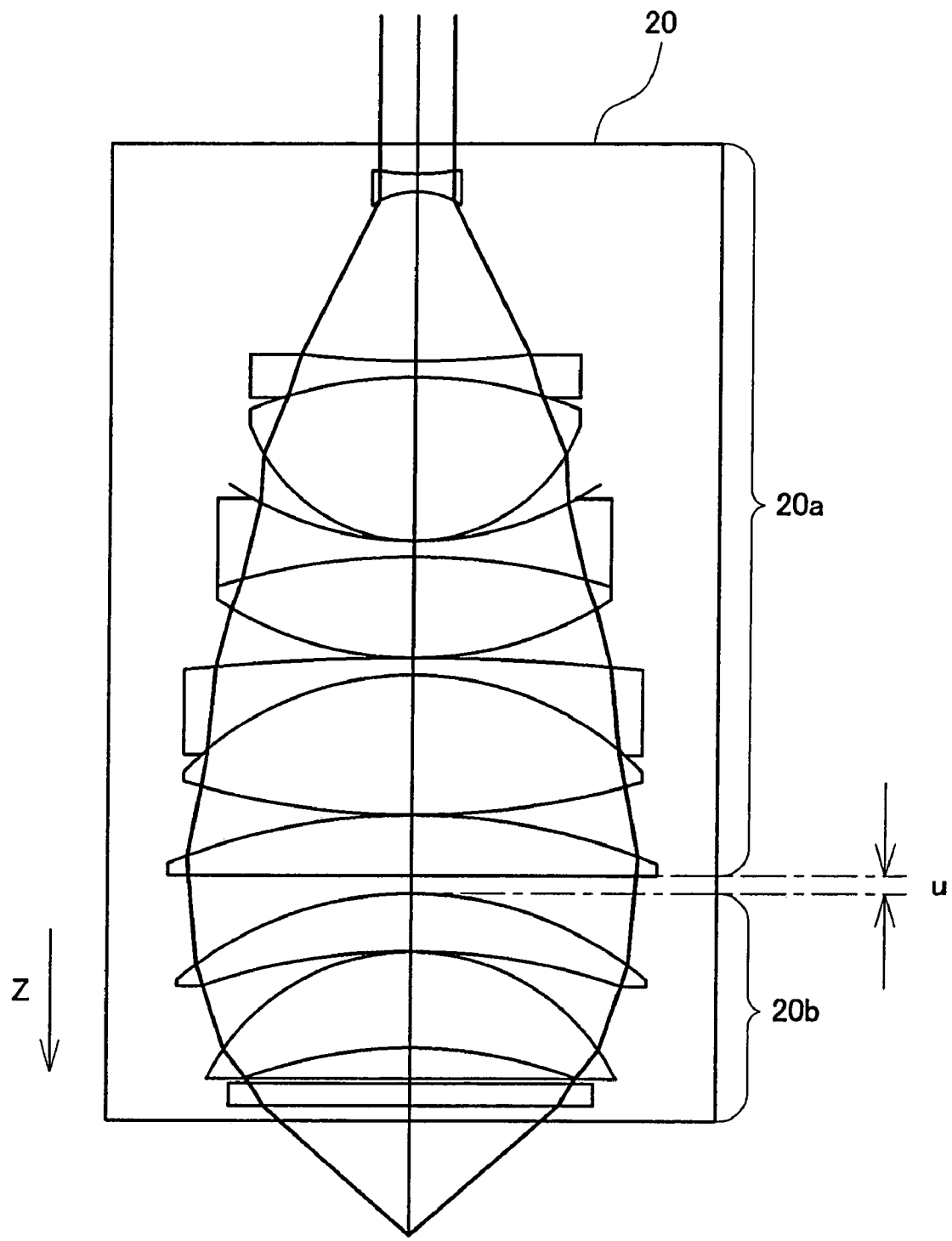
FIG. 2 is a side sectional view showing a configuration of an objective lens in the inspection apparatus shown in FIG. 1.

In the present embodiment, as shown in the side sectional view of FIG. 2, the objective lens 20 is composed of two lens units, first lens unit 20a and second lens unit 20b. These lens units 20a, 20b are located on the upper side and on the lower side, respectively, along the optical axis of the objective lens 20. The objective lens 20 is so configured that a spacing u between the lens units 20a and 20b can be varied by rotating a correction ring 21 (cf. FIG. 1) provided in its peripheral part. The correction ring 21 is controlled in driving by correction ring driver 40. This permits the correction ring 21 and correction ring driver 40 to function as an aberration correction means for effecting aberration correction in observation by changing the spacing u between the lens units 20a, 20b in the objective lens 20.

In the configuration as described above, the focusing means comprised of the Z stage 15b, and the aberration correction means comprised of the correction ring 21 and correction ring driver 40 constitute an objective lens driving means for driving the objective lens 20 to effect the focusing and aberration correction for the semiconductor device S. FIG. 2 is depicted without illustration of a specific structure and driving mechanism of the objective lens 20 including the correction ring 21. It is also possible to drive the stage 18 carrying the semiconductor device S, in order to achieve the focusing for the semiconductor device S.

In the inspection apparatus shown in FIG. 1, an inspection part 12, 16 is provided for the semiconductor device S. In the inspection of semiconductor device S, the inspection part 16 performs control of a state of the semiconductor device S and others according to need. There are different methods of controlling the state of the semiconductor device S by the inspection part 16, depending upon specific inspection methods applied to the semiconductor device S; for example, applicable methods include a method of supplying a voltage to a predetermined portion of a circuit pattern formed in the semiconductor device S, a method of irradiating a laser beam as a probe beam to the semiconductor device S, and so on.

In the present embodiment, SIL 3 is further disposed in this observation part A. This SIL 3 is a lens used for magnifying the image of the semiconductor device S. The SIL 3 is arranged movable relative to the image acquisition part 1 and optical system 2 and relative to the semiconductor device S mounted on the stage 18. Specifically, the SIL 3 is arranged to be movable between an insertion position at which the SIL 3 is placed so as to include the optical axis from the semiconductor device S to the objective lens 20 and be kept in contact with the semiconductor device S, and a standby position off the optical axis.

A solid immersion lens driver (SIL driver) 30 is provided for the SIL 3. The SIL driver 30 is a driving means for driving the SIL 3 to move it between the aforementioned insertion position and standby position. The SIL driver 30 finely moves the location of SIL 3 to adjust the insertion position of SIL 3 relative to the objective lens 20 of the optical system 2. In FIG. 1, the SIL 3 is illustrated in a state in which it is placed at the insertion position between the objective lens 20 and the semiconductor device S.

Here the SIL is usually a lens of hemispherical shape with the focal point at the center of sphere effecting n-fold multiplication of the numerical aperture NA and magnification, or a lens of hyperhemispherical shape with the focal point at a position R/n below the center of sphere, effecting $n^2$-fold multiplication of the numerical aperture NA and magnification (e.g., cf. Japanese Patent Application Laid-Open No. 2002-189000).

Figure 3:
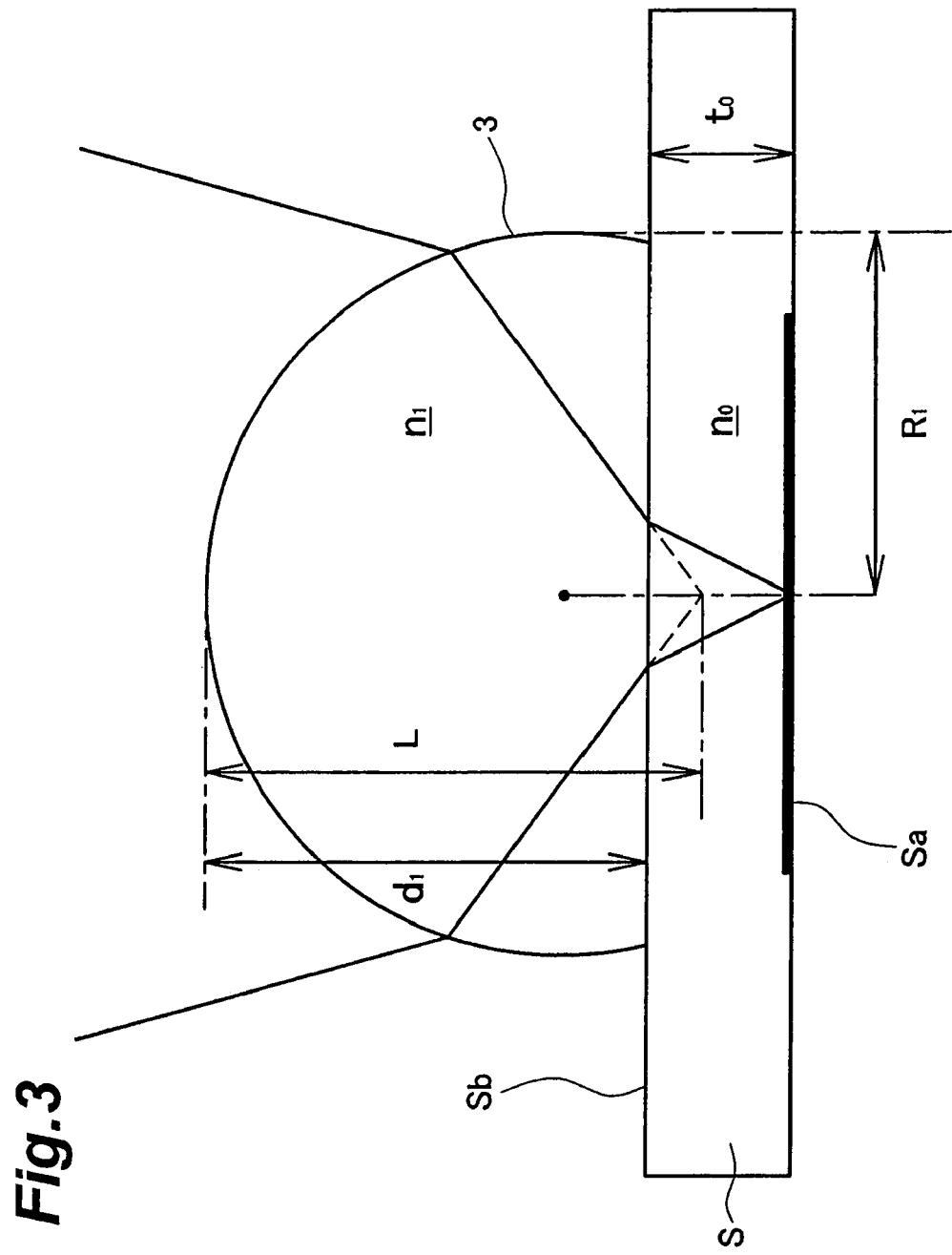
FIG. 3 is a side view showing a semiconductor device observation method with an SIL in the inspection apparatus shown in FIG. 1.

FIG. 3 is a side view showing an observation method of the semiconductor device using the SIL in the inspection apparatus shown in FIG. 1. In the present inspection apparatus, as described above, the semiconductor device S is placed on the stage 18 so that the device surface Sa thereof is down (on the stage 18 side) and the back surface Sb up (on the objective lens 20 side). Relative to this semiconductor device S, the SIL 3 at the insertion position is placed so that its planar or convex lens surface is kept in close contact with the back surface Sb. Specific examples of the SIL include such known lenses as plano-convex lenses and bi-convex lenses (e.g., reference should be made to Japanese Patent Application Laid-Open No. H5-157701 and U.S. Pat. No. 6,594,086).

Where the semiconductor device S is observed from the back side Sb through the substrate by use of the objective lens 20 and SIL 3, the optical parameters in the semiconductor device S include the refractive index $n_0$ and the thickness $t_0$ of the substrate. The optical parameters in the SIL 3 include the refractive index $n_1$, thickness $d_1$, and curvature radius $R_1$ of the spherical lens surface. In FIG. 3, solid lines indicate optical paths traveling from the objective lens 20 side through the SIL 3 and the substrate and focused on the device surface Sa. In addition, dashed lines indicate optical paths on the assumption that the refractive index $n_0$ of the substrate of the semiconductor device S would be equal to that $n_1$ of SIL 3.

In the same drawing L represents a depth of measurement from the spherical surface of the solid immersion lens, SIL 3 in the case of the optical paths indicated by the dashed lines, i.e., a distance between the focal point determined from the shape of the lens surface of SIL 3 and the apex of SIL 3 (hereinafter referred to as a measurement depth). This measurement depth L is determined by $L=d_1+t_0 \times (n_1/n_0)$ so as to set the focal point on the device surface Sa in actual observation. A specific lens shape of the SIL 3 (e.g., setting of thickness $d_1$ to curvature radius $R_1$) can be optionally set according to need. In general, as to the thickness $t_0$ of the substrate (sample), where the observation is carried out at the observation plane set inside the sample and through part of the sample, the thickness of the sample up to the observation plane can be set as the thickness $t_0$.

For the observation part A for carrying out the observation and others for inspection of the semiconductor device S, there are provided the control part B and analysis part C.

The control part B has an observation controller 51, a stage controller 52, an SIL controller 53, and an objective lens controller 54. The observation controller 51 controls operations of the image acquisition part 1 and inspection part 16, thereby controlling execution of observation of the semiconductor device S carried out in the observation part A, setting of observation conditions, and so on.

The stage controller 52 controls the operation of XY stage 15a, thereby controlling setting of the observation position of the semiconductor device S by the image acquisition part 1 and optical system 2 as an inspection position in the present inspection apparatus, or positioning thereof. The SIL controller 53 controls the operation of SIL driver 30, thereby controlling movement of the SIL 3 between the insertion position and the standby position, or adjustment of the insertion position of SIL 3, or the like.

The objective lens controller 54 controls the operation of the Z stage 15b, thereby controlling the focusing to change the distance between the substrate of the semiconductor device S and the objective lens 20. Furthermore, this controller 54 controls the operations of the correction ring driver 40 and the correction ring 21, thereby controlling the aberration correction to change the spacing u between the lens units 20a, 20b in the objective lens 20.

The analysis part C has an image analyzer 61 and instructor 62. The image analyzer 61 performs a required analysis process and others for the image acquired by the image acquisition part 1. The instructor 62 gives necessary instructions for the control part B, with reference to input contents from an operator, analysis contents by the image analyzer 61, and so on. A display unit 63 is coupled to the analysis part C. An image, data, or the like acquired or analyzed by the analysis part C is displayed on the display unit 63 as occasion may demand.

In this configuration, the control part B serves as a controlling means for controlling the objective lens driving means including the Z stage 15b, correction ring driver 40, and correction ring 21, and the solid immersion lens driving means including the SIL driver 30, to control the observation conditions in observation of the device surface Sa of the semiconductor device S. In the present embodiment, particularly, corresponding to the configuration wherein the SIL 3 is movable between the insertion position and the standby position, the control part B including the SIL controller 53 and the objective lens controller 54 has two control modes, a normal mode (first mode) and a solid immersion lens mode (SIL mode or second mode).

In the normal mode, the SIL controller 53 makes the SIL driver 30 place the SIL 3 at the standby position off the optical axis. The objective lens controller 54 controls the Z stage 15b, correction ring driver 40, and correction ring 21 to perform the focusing and aberration correction in observation conditions, under a first correction condition set based on the refractive index $n_0$ and thickness $t_0$ of the substrate of the semiconductor device S. Then the observation of the semiconductor device S from the back side Sb is carried out through the optical system 2 including the objective lens 20. The objective lens controller 54 is provided with a first focusing table and a first aberration correction table corresponding to the first correction condition.

In the SIL mode, the SIL controller 53 makes the SIL driver 30 place the SIL 3 at the insertion position including the optical axis. The objective lens controller 54 controls the Z stage 15b, correction ring driver 40, and correction ring 21 to perform the focusing and aberration correction in observation conditions, under a second correction condition set based on the refractive index $n_0$ and thickness $t_0$ of the substrate of the semiconductor device S, and the refractive index $n_1$, thickness $d_1$, and curvature radius $R_1$ of SIL 3. Then the observation of the semiconductor device S from the back side Sb is carried out through the optical system 2 including the objective lens 20, and through the SIL 3. The objective lens controller 54 is provided with a second focusing table and a second aberration correction table corresponding to this second correction condition.

Figure 4:
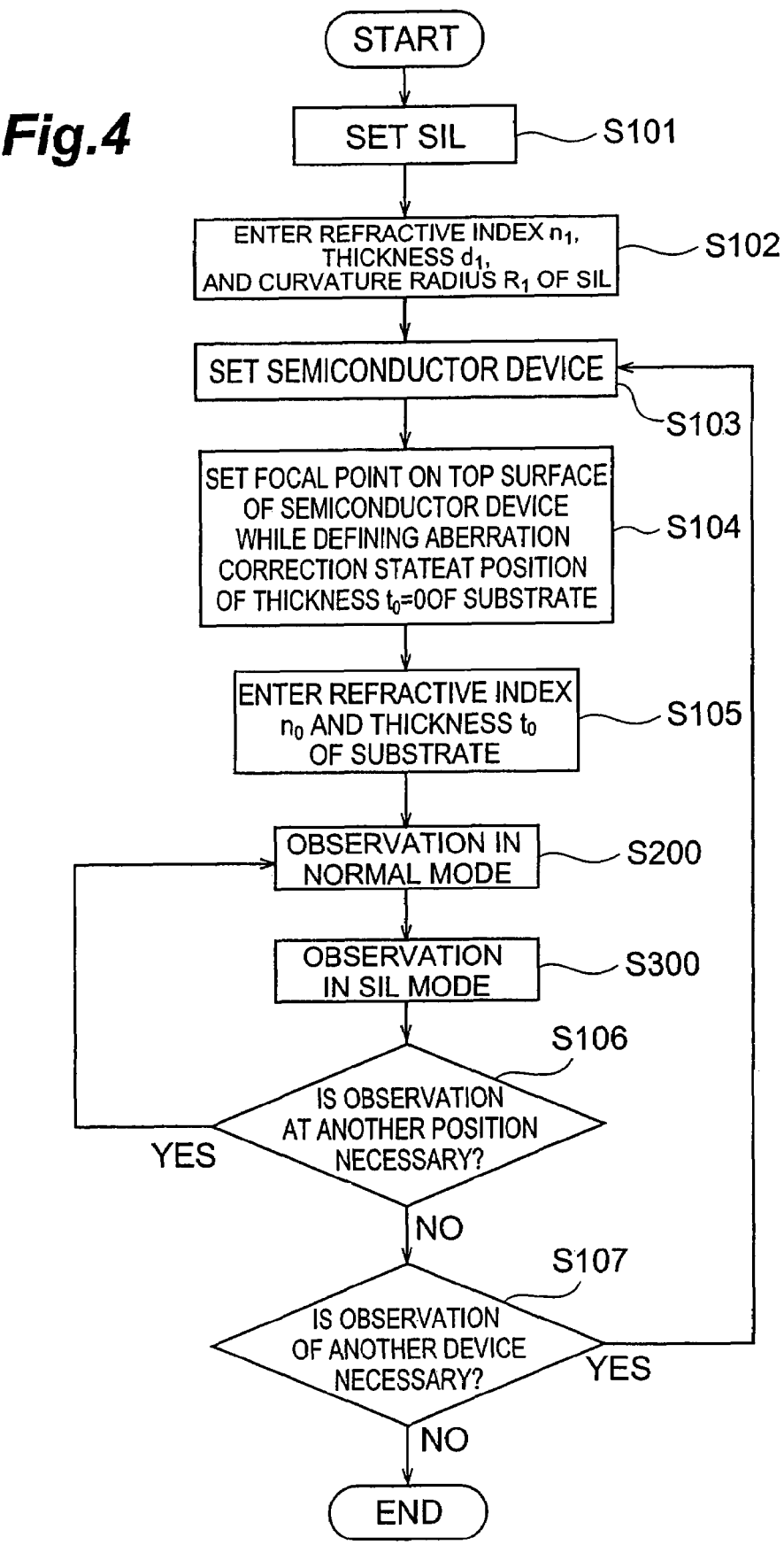
FIG. 4 is a flowchart showing an example of a semiconductor inspection method using the inspection apparatus shown in FIG. 1.
Figure 5:
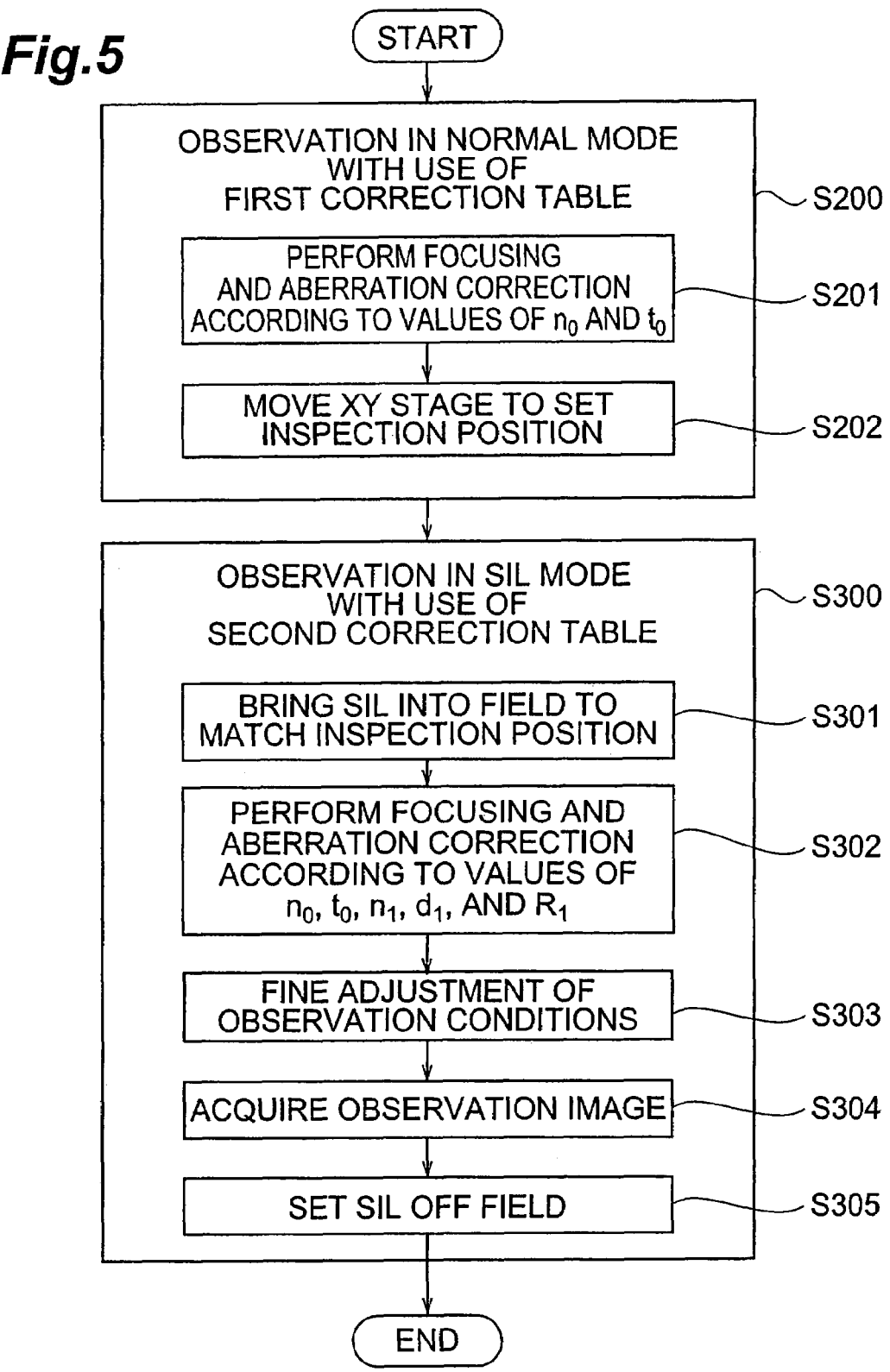
FIG. 5 is a flowchart showing observation in a normal mode and observation in an SIL mode in the inspection method shown in FIG. 4.
Figure 6:
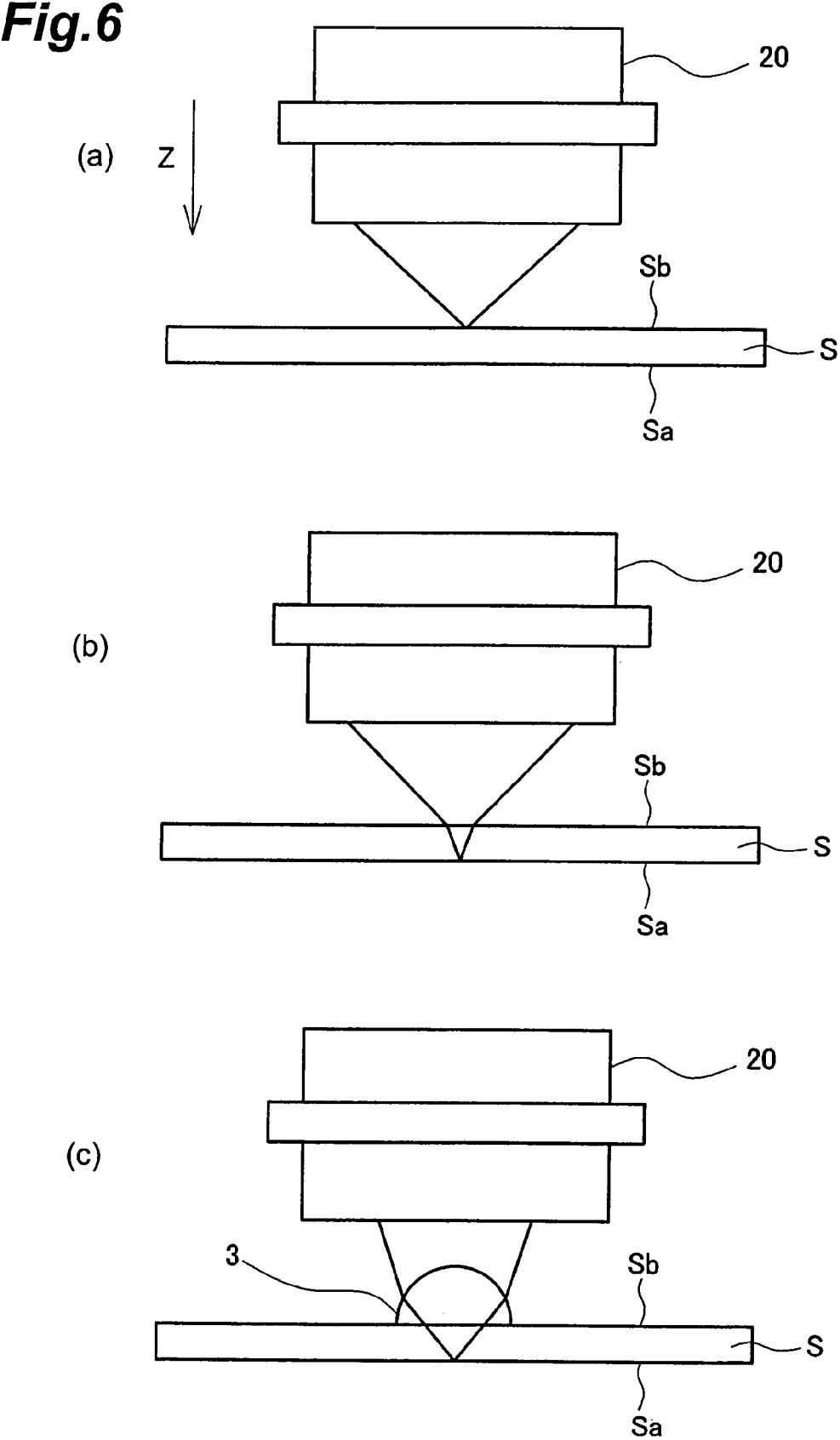
FIG. 6 is a figure including schematic diagrams showing (a) a default state, (b) a normal mode, and (c) an SIL mode in the observation of the semiconductor device.

Next, a semiconductor inspection method, which is a sample observation method according to the present invention, will be described. FIG. 4 is a flowchart showing an example of the semiconductor inspection method using the inspection apparatus shown in FIG. 1. FIG. 5 is a flowchart specifically showing observation methods by observation in the normal mode and observation in the SIL mode in the inspection method shown in FIG. 4. FIG. 6 is a figure including schematic diagrams showing (a) the default state, (b) the normal mode, and (c) the SIL mode in observation of a semiconductor device.

The first step is to select an SIL 3 having optical parameters suitable for observation of the semiconductor device S as an inspected object and to set the SIL 3 on the SIL driver 30 (step S101). Then the optical parameters of the refractive index $n_1$, thickness $d_1$, and curvature radius $R_1$ of the selected SIL 3 are entered through an input device provided in the analysis part C (S102). The semiconductor device S as an inspected object is set with its back side Sb up on the stage 18 (S103). Then the focal point of observation is matched with the back side Sb of the semiconductor device S thus set. This results in setting the focus and aberration so as to locate the focal point on the back side Sb being the top surface of the semiconductor device S, as shown in FIG. 6(a) (S104). This state, i.e., the thickness of substrate $t_0=0$ is the default state (origin set state) in observation of the semiconductor device S. In this state the SIL 3 is positioned at the standby position off the optical axis.

Next, the optical parameters of the refractive index $n_0$ and thickness $t_0$ of the substrate of the semiconductor device S being a sample of an observed object are entered (S105).

Subsequently, the semiconductor device S is observed in the normal mode with use of the objective lens 20 (S200). Specifically, as shown in the flowchart of FIG. 5, the movement amount $\Delta Z$ of the objective lens 20 and the spacing u between lens units 20a, 20b are adjusted using the first focusing table and the first aberration correction table according to the refractive index $n_0$ and the thickness $t_0$ of the substrate. This results in executing the focusing and aberration correction so as to match the focal point with the device surface Sa set at the observation plane of the semiconductor device S and through the substrate from the back side Sb, as shown in FIG. 6(b) (S201, first correction step).

After completion of the setting of the observation conditions, an observation for inspection of the semiconductor device S is carried out (S202, first image observation step). At this step, a normal image of a circuit pattern provided in the device surface Sa of the semiconductor device S is observed through the optical system 2 containing the objective lens 20, by the image acquisition part 1. The stage controller 52 drives the XY stage 15a to move the image acquisition part 1 and optical system 2 in the X-Y plane. Then a portion to be observed in the semiconductor device S is set at the center of the field of view and is specified as an inspection position (observation position).

Subsequently, an observation is carried out in the SIL mode using the SIL 3 in addition to the objective lens 20 (S300). Specifically, the SIL controller 53 drives the SIL driver 30 to move the SIL 3 from the standby position to the insertion position. Then the SIL 3 is brought into the field so as to match the inspection position, in a state in which the SIL 3 is in close contact with the back side Sb of the semiconductor device S (S301). In this state, the movement amount $\Delta Z$ of the objective lens 20, and the spacing u between lens units 20a, 20b are adjusted using the second focusing table and the second aberration correction table according to the refractive index $n_0$ and thickness $t_0$ of the substrate, and the refractive index $n_1$, thickness $d_1$, and curvature radius $R_1$ of the SIL 3. This results in executing the focusing and aberration correction so as to match the focal point with the device surface Sa of the semiconductor device S through the SIL 3 and the substrate, as shown in FIG. 6(c) (S302, second correction step). Fine adjustment is carried out as to the observation conditions such as the focal point, aberration, and the location of the SIL 3 as occasion may demand (S303).

After completion of the setting of the observation conditions, the observation of the semiconductor device S is carried out (S304, second image observation step). At this step, an enlarged image of the semiconductor device S is observed through the optical system 2 containing the objective lens 20, and through the SIL 3 by the image acquisition part 1 to inspect a circuit pattern at the inspection position. After completion of the necessary observation and inspection for the set inspection position, the SIL 3 is moved out of the field to the standby position (S305).

Then, whether it is necessary to observe another position is determined for the semiconductor device S set on the stage 18, as shown in the flowchart of FIG. 4 (S106). If necessary, the observation in the normal mode (S200) and the observation in the SIL mode (S300) are repeatedly carried out. If there is no need for observation of another position, it is determined whether it is necessary to observe another semiconductor device (S107). If necessary, the processes including the step of setting the semiconductor device S (S103) and the steps thereafter are repeatedly carried out. If there is no need for observation of another semiconductor device, the inspection of semiconductor device is terminated.

The effects of the semiconductor inspection apparatus and semiconductor inspection method in the present embodiment will be described below.

In the semiconductor inspection apparatus shown in FIG. 1 and in the semiconductor inspection method shown in FIGS. 4 and 5, the inspection of the semiconductor device S from the back side Sb through the substrate is carried out so as to implement the inspection with a switchover between the normal mode of carrying out the observation with the SIL 3 at the standby position and under the observation conditions taking account of the optical parameters $n_0$, $t_0$ of the substrate and the SIL mode of carrying out the observation with the SIL 3 at the insertion position and under the observation conditions taking account of the optical parameters $n_0$, $t_0$ of the substrate and the optical parameters $n_1$, $d_1$, $R_1$ of the SIL 3. This makes it feasible to properly execute the focusing and aberration correction in each of the present and absent states of SIL 3 and to suitably acquire each of the normal image and the enlarged image of the semiconductor device S. Accordingly, it becomes feasible to readily carry out the inspection such as the analysis of microstructure of the semiconductor device. S.

The above embodiment employs the Z stage 15b to adjust the spacing between the substrate of the semiconductor device S and the objective lens 20, as the focusing means for the objective lens 20. The above embodiment also adopts the lens configuration consisting of the lens units 20a, 20b and the correction ring 21 and the correction ring driver 40 for adjustment of the spacing between the lens units, as the aberration correction means for the objective lens 20. This configuration permits us to suitably adjust the focus and aberration in observation of the semiconductor device S. It is also a matter of course that any configuration other than these may be used. For example, as to the focusing for the semiconductor device S, it is also possible to adopt the configuration of driving the stage 18 carrying the semiconductor device S in the Z-axis direction as described above.

The focusing and aberration correction are executed by the specific methods using the focusing tables and aberration correction tables prepared corresponding to the respective correction conditions in the control part B. This implements easy and sure correction for the observation conditions for the semiconductor device S. However, the focusing and aberration correction can also be implemented by use of any other method than the above methods using the focusing tables and aberration correction tables. For example, a potential configuration is such that computational expressions necessary for focusing and aberration correction are prepared and conditions for focusing and aberration correction are calculated using the computational expressions.

In the configuration shown in FIG. 1, specifically, the focusing tables are preferably prepared based on Z-directional driving distances (focus movement amounts) ΔZ of the objective lens 20 by the Z stage 15b. The aberration correction tables are preferably prepared based on spacings u between lens units 20a, 20b in the objective lens 20 or based on amounts of rotation of the correction ring 21 corresponding to spacings u.

These correction tables may be arranged as follows: tables are preliminarily prepared in the number necessary for combinations of optical parameters of envisioned substrates and SILs and a table to be used is selected according to input parameters. Alternatively, a correction table may be created at a point of time of entry of parameters. The entry of the optical parameters of SIL can be implemented by individually entering values of parameters, or by any other method, for example, by a configuration of preparing a set of parameters corresponding to each model number of SIL, by a configuration of providing each SIL with a storage medium such as an IC chip storing values of parameters, and retrieving the data at a time of use, and so on.

Listed below are principal materials to be used for the semiconductor substrate and SIL, and refractive indices n thereof.

Si: 3.5
GaP: 3.1
GaAs: 3.4
Glass: 1.45-2
Plastics: 1.45-2

The material of SIL is preferably selected as one with a refractive index close to that of the substrate material such as Si or GaP in the semiconductor device as an inspected object. The above embodiment described the semiconductor inspection apparatus and inspection method for the semiconductor device as a sample of an observed object, and in general, where samples are a variety of devices such as the semiconductor devices, the target devices do not have to be limited to those using a semiconductor substrate, but observed objects may also be integrated circuits using a substrate of glass, plastic, or the like, such as polysilicon thin-film transistors. For example, a device is fabricated on a glass substrate in the case of a liquid crystal device, and a device is fabricated on a plastic substrate in the case of an organic EL device or the like.

Where the SIL used is one made of Si, it presents an advantage of no aberration at the interface between the substrate and the SIL if the substrate is an Si substrate. However, attention is needed in that the transmittance is low for light of wavelengths of not more than 1.1 μM and the light is absorbed by the SIL even if the substrate is made thin.

Where the SIL used is one made of GaP, it presents an advantage of also transmitting light with wavelengths ranging from the visible to infrared region, in addition to the wavelength region transmitted by Si. In this case, if the Si substrate has a thickness small enough, the observation can be performed in such a wavelength region. For example, where the Si substrate has the thickness as thin as about 30 μm and where a laser beam with the wavelength of not more than 1 μm is used in acquisition of an image by LSM (described later), it is feasible to implement achievement of high resolution of observation. On the other hand, attention is needed in that the GaP SIL gives rise to geometric aberration like spherical aberration due to the index difference at the interface between the substrate and the SIL in the case of the Si substrate. When the substrate is thin enough as described above, the effect of geometric aberration can be ignored.

The semiconductor inspection method described above will be further described with specific data.

First, the correction for the observation conditions in the normal mode will be described. In the observation of the device surface Sa of the semiconductor device S with the objective lens 20 (cf. FIG. 6(b)), the geometric aberration I appearing on the back side Sb of the substrate is given by Eq (1) below.

$$I = (n_0^2 - 1) t_0 N A^2 / (2 n_0^3) \tag{1}$$

In this Eq (1), NA represents the numerical aperture of the objective lens 20.

Figure 7:
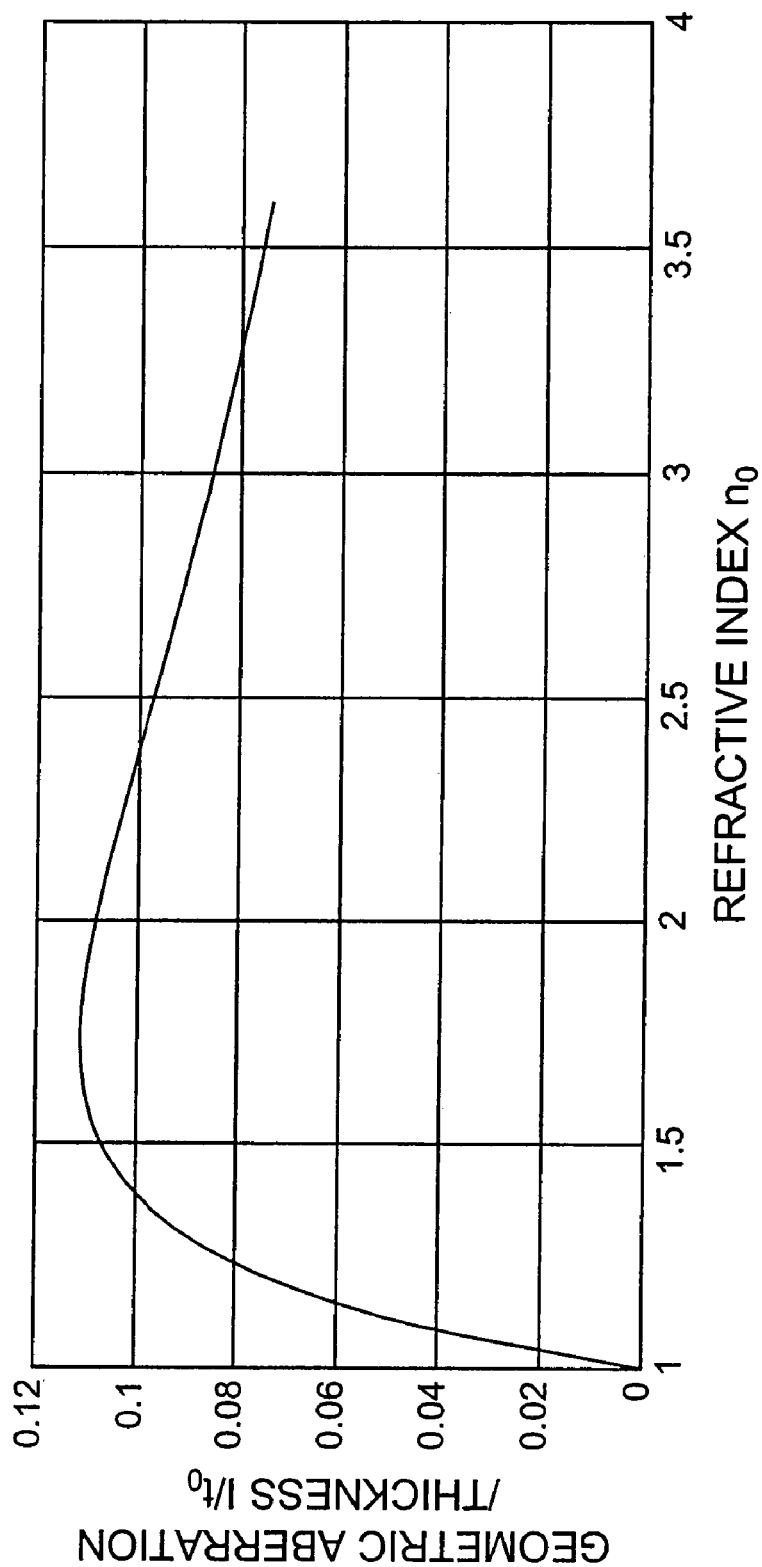
FIG. 7 is a graph showing an example of correlation between refractive index of substrate, and geometric aberration.

FIG. 7 is a graph showing an example of correlation between refractive index of substrate and geometric aberration. In this graph, the horizontal axis represents the refractive index $n_0$ of the substrate (sample) as an observed object, and the vertical axis (geometric aberration/thickness of substrate) $I/t_0$. In this graph, the numerical aperture of the objective lens 20 is assumed to be NA=0.76. In the correction for the observation conditions in the normal mode, the focusing table and aberration correction table are prepared based on the optical characteristics such as the geometric aberration I determined in this way.

Figure 8:
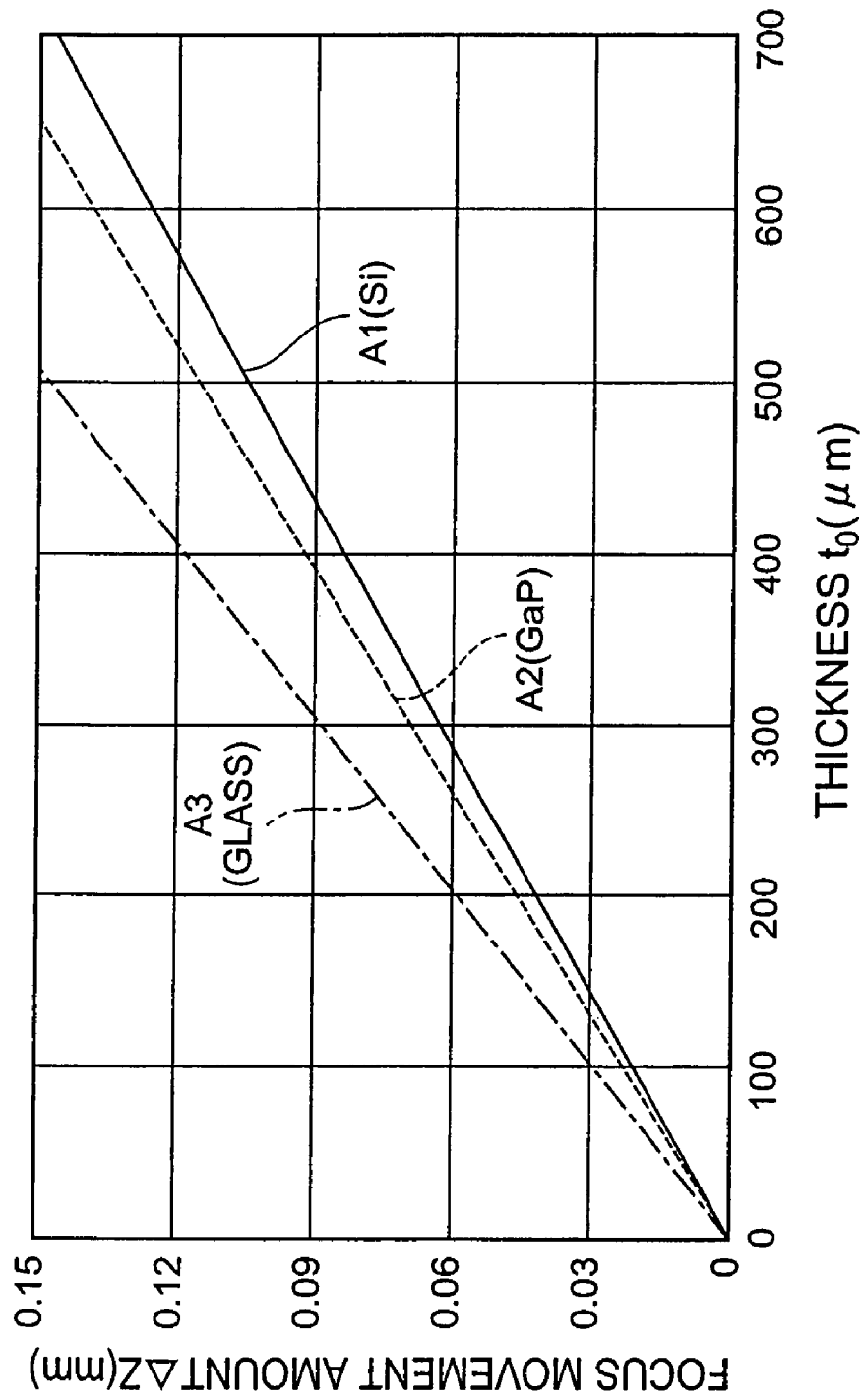
FIG. 8 is a graph showing an example of correlation between thickness of substrate, and focus movement amount.

FIG. 8 is a graph showing an example of correlation between thickness of substrate and focus movement amount of movement of the objective lens. In this graph, the horizontal axis represents the thickness $t_0$ (μm) of the substrate, and the vertical axis the focus movement amount ΔZ (mm). Graph A1 indicates a correlation in the case of the substrate material of Si ($n_0$=3.5), graph A2 that in the case of the substrate material of GaP ($n_0$=3.1), and graph A3 that in the case of the substrate material of glass ($n_0$=1.5). As apparent from Eq (1), if NA and $n_0$ are constant, the geometric aberration I is proportional to the thickness $t_0$ of the substrate. In the example shown in FIG. 8, therefore, the focus movement amount ΔZ for focusing can be calculated by a proportional expression to the thickness $t_0$ or the geometric aberration I.

Figure 9:
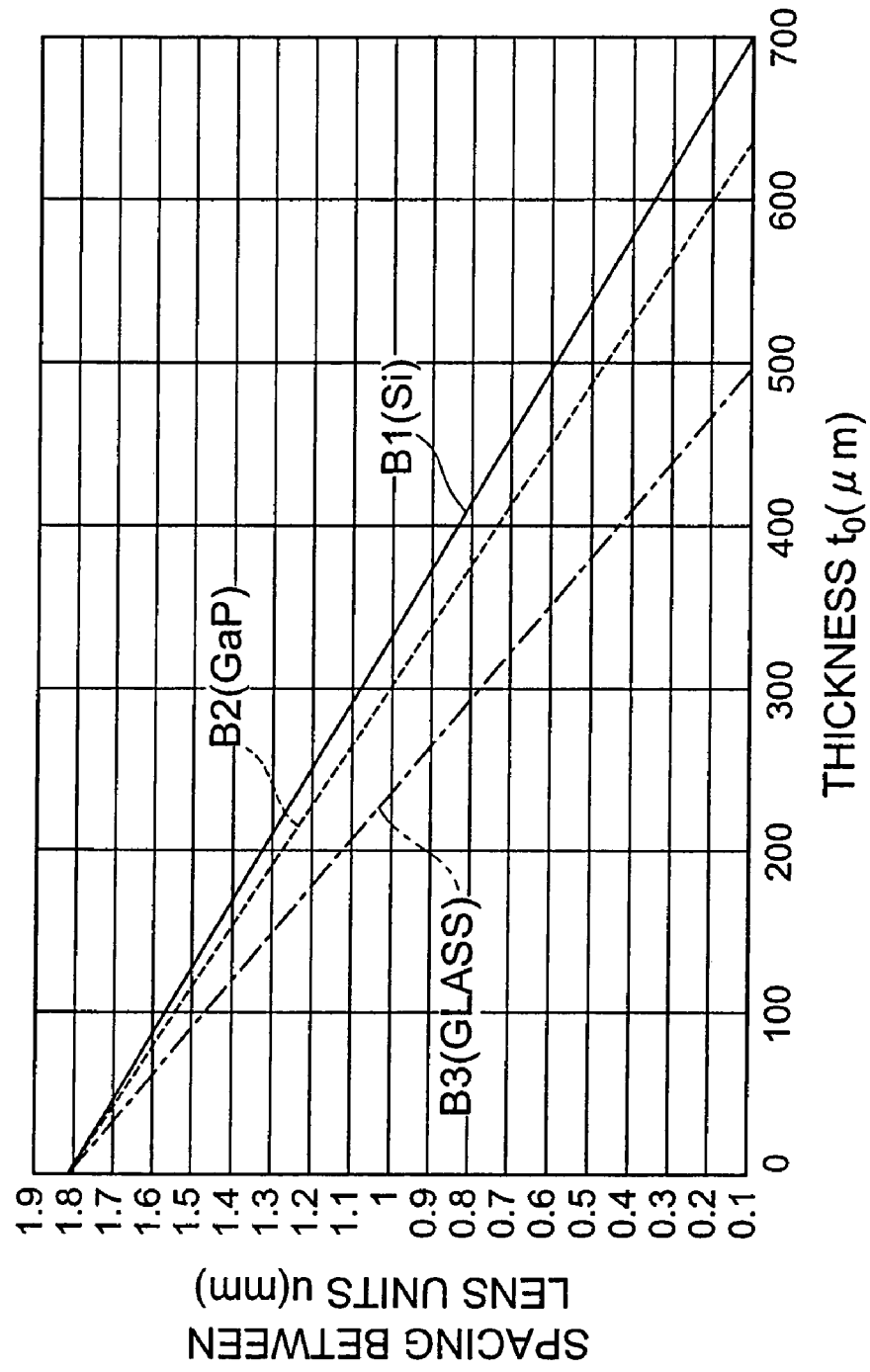
FIG. 9 is a graph showing an example of correlation between thickness of substrate and spacing between lens units in the objective lens.

FIG. 9 is a graph showing an example of correlation between thickness of substrate and spacing between lens units in the objective lens. In this graph, the horizontal axis represents the thickness $t_0$ (μm) of the substrate, and the vertical axis the spacing u (mm) between lens units 20a, 20b set in the objective lens 20. Graph B1 indicates a correlation in the case of the substrate material of Si, graph B2 that in the case of the substrate material of GaP, and graph B3 that in the case of the substrate material of glass. In the example shown in FIG. 9, the spacing u between lens units for aberration correction can be calculated by a linear expression to the thickness $t_0$ or the geometric aberration I. In FIGS. 8 and 9, specific correlation equations including coefficient values and others are determined by a lens configuration of each objective lens 20 or the like. A function system including the order of the correlation equations and others can be optionally determined out of appropriate systems.

Next, the correction for the observation conditions in the SIL mode will be described. In the observation of the device surface Sa with the SIL 3 in addition to the objective lens 20 (cf. FIG. 6(c)), the geometric aberration I amounts to the sum I=I1+I2 of the geometric aberration I1 appearing at the lens spherical surface of SIL 3 and the geometric aberration I2 appearing at the interface between SIL 3 and the substrate. The geometric aberration I1 appearing at the lens spherical surface of SIL 3 is given by Eq (2) below, supposing $R_1$=1 mm and $n_1$=3.5 for simplicity.

$$I1 = 6.25(L-1)^2 \times (3.5L - 4.5)L \tag{2}$$

In this Eq (2), L represents the measurement depth of SIL 3 shown in FIG. 3.

The geometric aberration I2 appearing at the interface between SIL 3 and the substrate is given by Eq (3) below.

$$I2 = n_1(n_0^2 - n_1^2)t_0 NA^2/(2n_0^3) \quad (3)$$

In the correction for the observation conditions in the SIL mode, the focusing table and aberration correction table are prepared based on the optical characteristics such as the geometric aberrations 11, 12 determined in this way.

Figure 10:
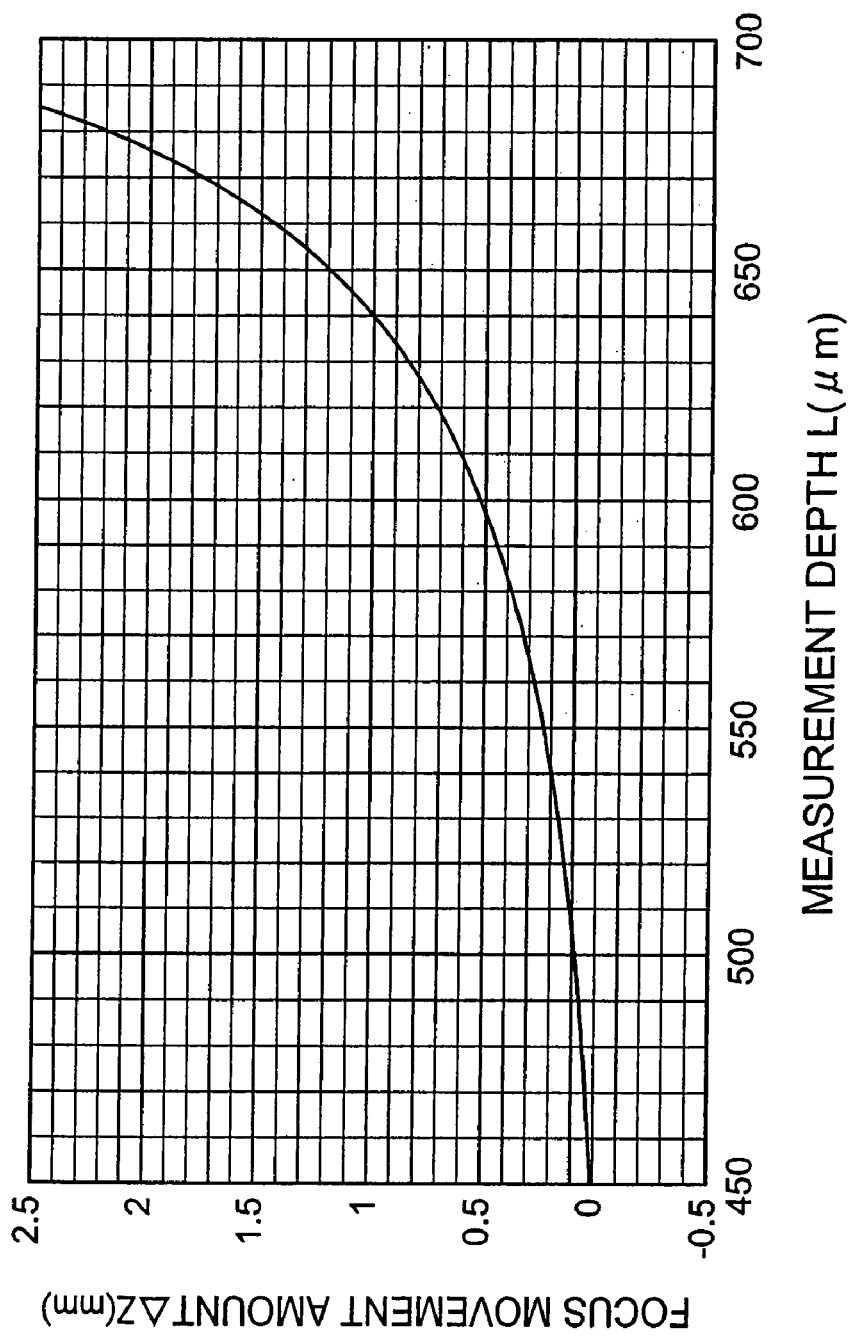
FIG. 10 is a graph showing an example of correlation between depth of measurement and focus movement amount.

FIG. 10 is a graph showing an example of correlation between measurement depth and focus movement amount. In this graph, the horizontal axis represents the measurement depth L (μm), and the vertical axis the focus movement amount ΔZ (mm). In this graph, the optical parameters of the substrate are set as $n_0=3.5$ and to =100 μm, and the optical parameters of the SIL 3 as $n_1=3.1$ and $R_1=0.5$ mm. The thickness $d_1$ of SIL 3 varies with the measurement depth L according to the aforementioned equation of $L=d_1+t_0 \times (n_1/n_0)$. The focus movement amount ΔZ for focusing is calculated by the correlation as shown in this FIG. 10.

Figure 11:
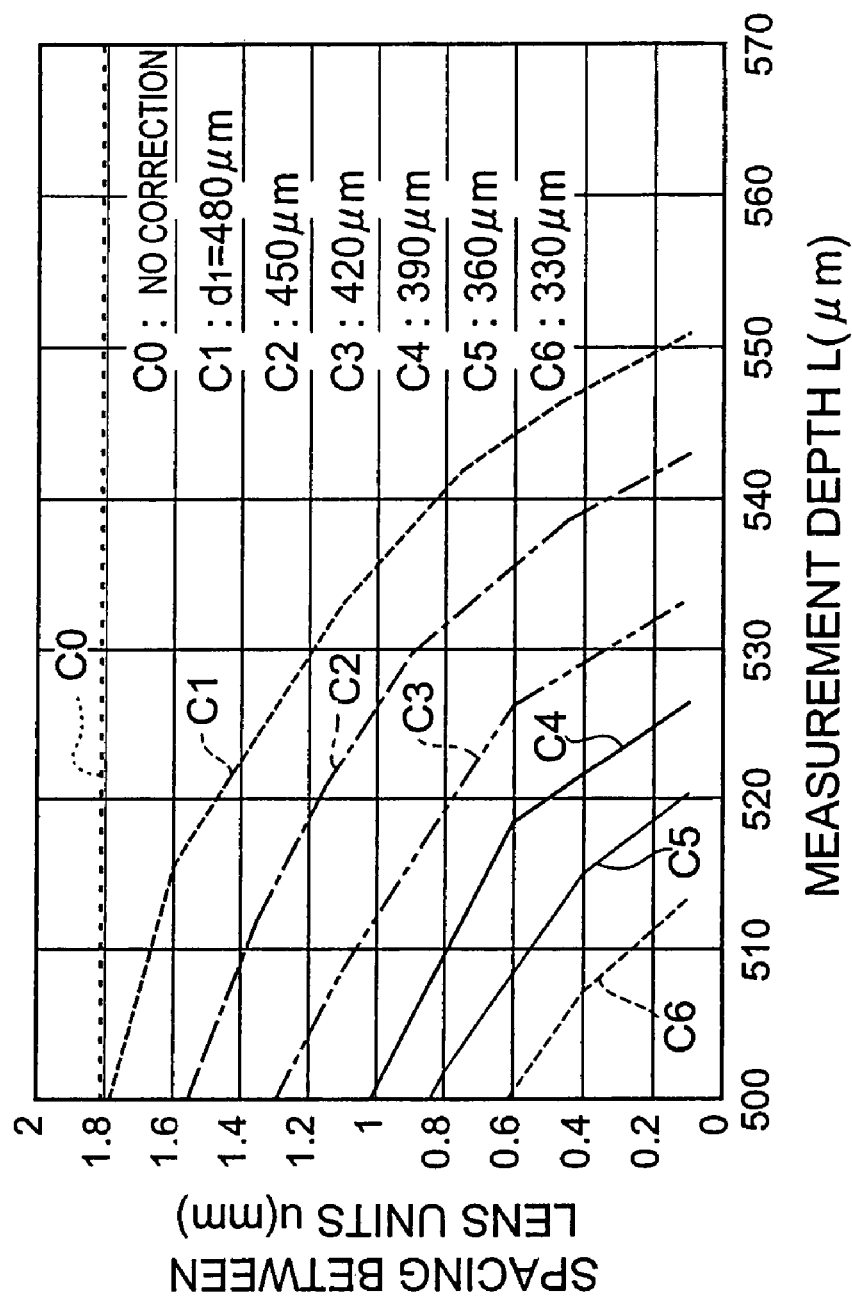
FIG. 11 is a graph showing an example of correlation between depth of measurement and spacing between lens units in the objective lens.

FIG. 11 is a graph showing an example of correlation between measurement depth and spacing between lens units in the objective lens. In this graph, the horizontal axis represents the measurement depth L (am), and the vertical axis the spacing u (mm) between lens units 20a, 20b. This graph shows corrected states where the optical parameter of the substrate is $n_0=3.5$, the optical parameters of the SIL 3 are $n_1=3.1$ and $R_1=0.5$ mm, and attained NA is 2.2. Graph C0 indicates a state without correction, graph C1 a corrected state at the thickness $d_1=480$ μm of SIL 3, C2 that at $d_1=450$ μm, C3 that at $d_1=420$ μm, C4 that at $d_1=390$ μm, C5 that at $d_1=360$ μm, and C6 that at $d_1=330$ μm. The thickness $t_0$ of the substrate varies with the measurement depth L according to the aforementioned equation of L.

Figure 12:
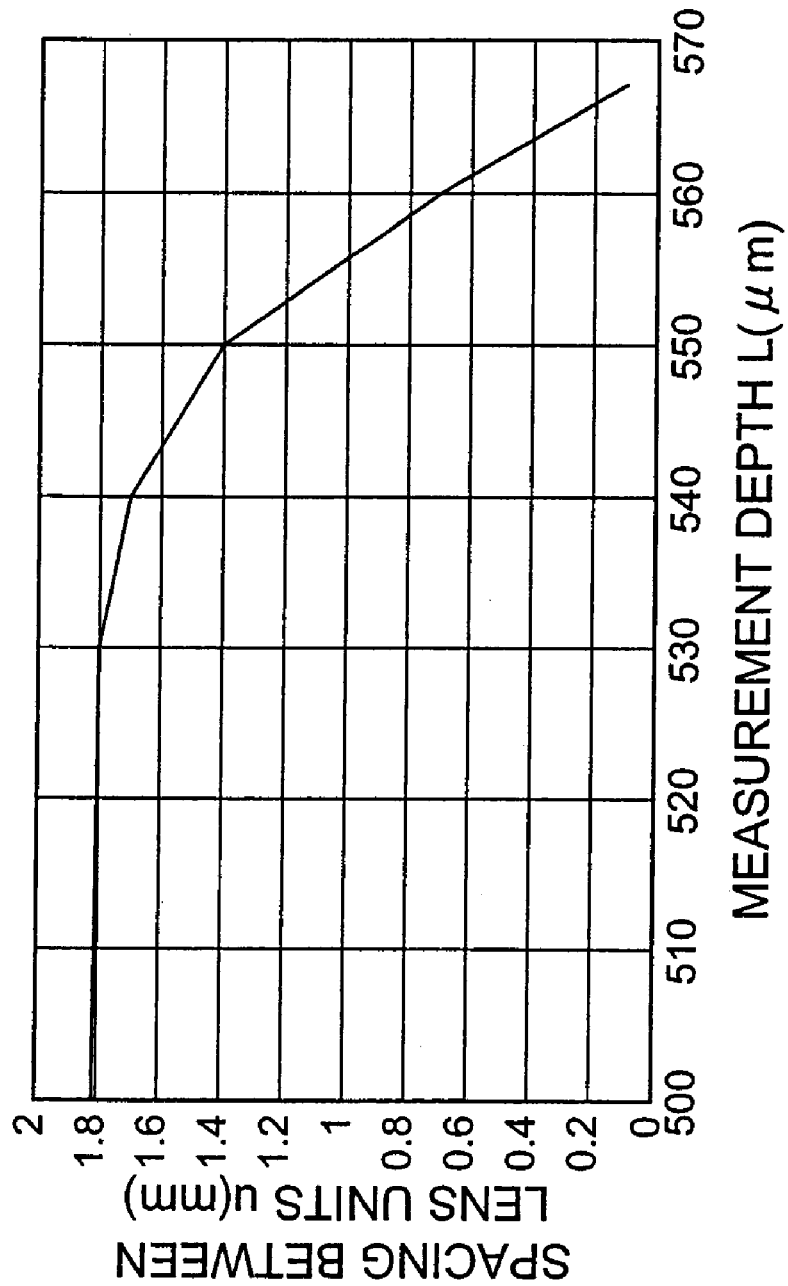
FIG. 12 is a graph showing another example of correlation between depth of measurement and spacing between lens units in the objective lens.

FIG. 12 is a graph showing another example of correlation between measurement depth and spacing between lens units in the objective lens. This graph shows a corrected state where the optical parameter of the substrate is $n_0=3.5$, the optical parameters of SIL 3 are $n_1=3.5$ and $R_1=0.5$ mm, and attained NA is 2.5. In this case, since the substrate and SIL 3 have the same refractive index, the spacing u between lens units is not dependent upon the thickness $d_1$ of SIL 3, but the thickness $t_0$ of the substrate and the thickness $d_1$ of SIL 3 vary in arbitrary combination with the measurement depth L. The spacing u between lens units for aberration correction is calculated by these correlations as shown in FIGS. 11 and 12.

The semiconductor inspection apparatus and inspection method according to the present invention will be further described below.

Figure 13:
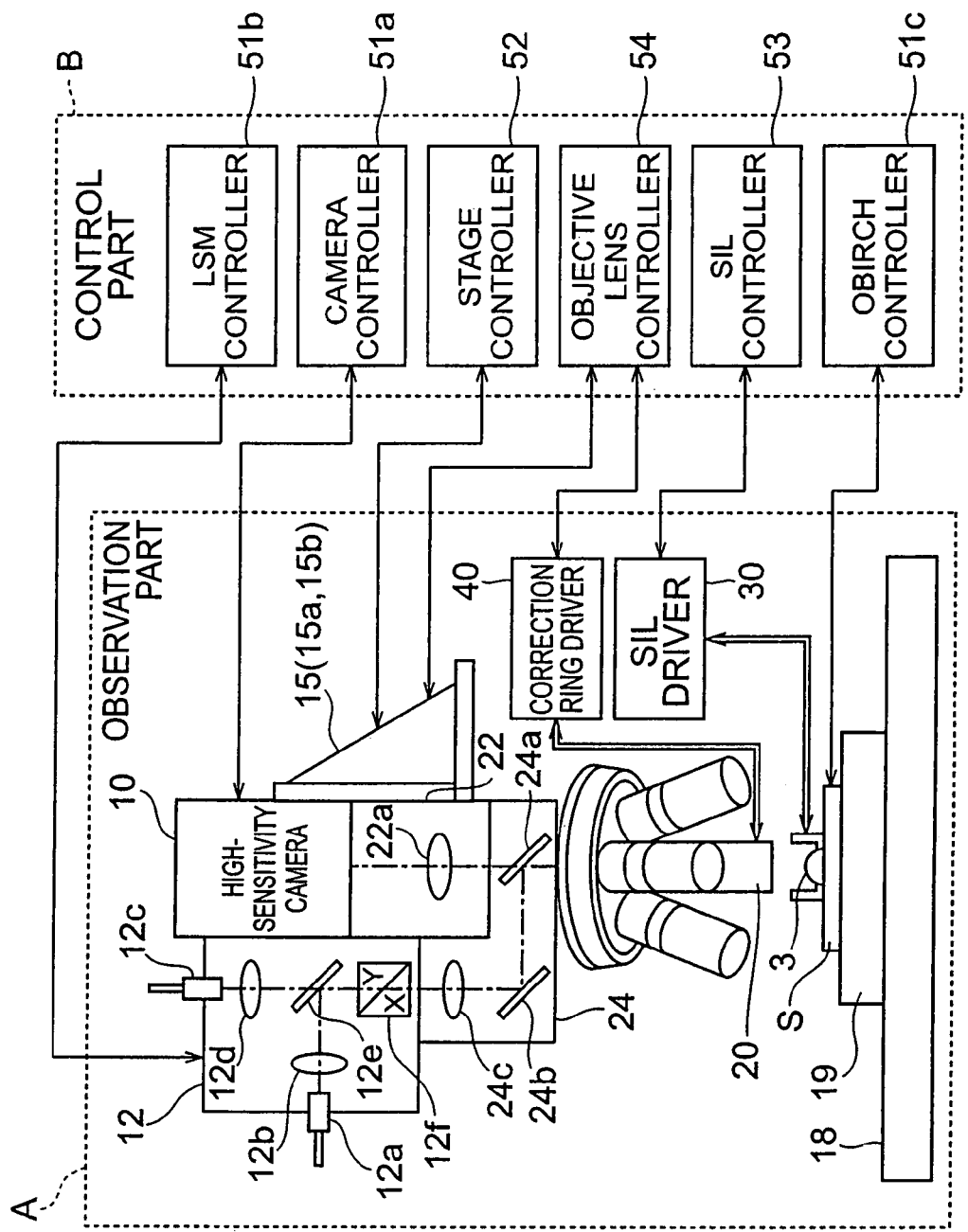
FIG. 13 is a configuration diagram showing another embodiment of the semiconductor inspection apparatus.
Figure 14:
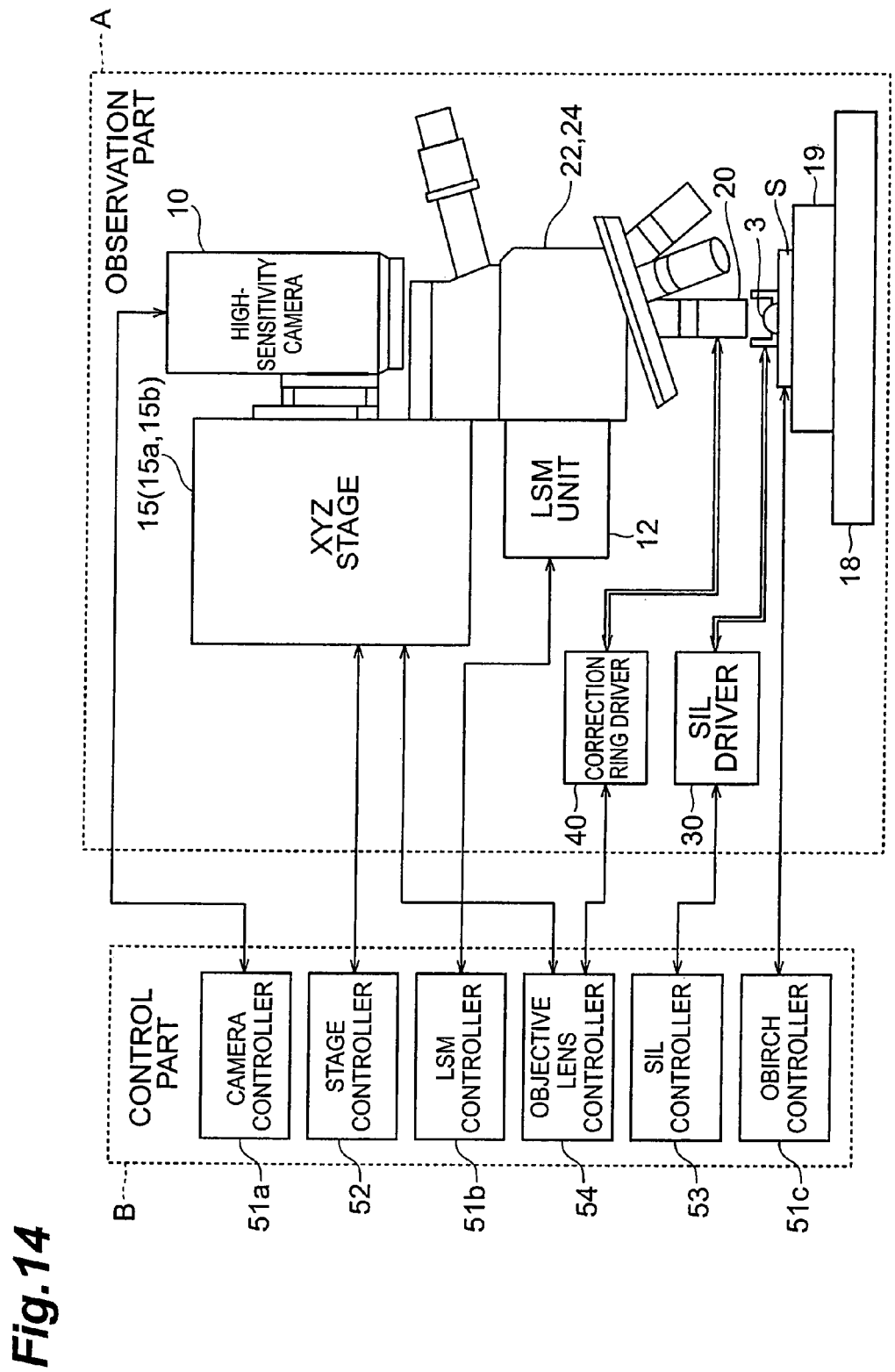
FIG. 14 is a configuration diagram showing a side view of the semiconductor inspection apparatus shown in FIG. 13.

FIG. 13 is a configuration diagram showing another embodiment of the semiconductor inspection apparatus according to the present invention. FIG. 14 is a configuration diagram showing a side view of the semiconductor inspection apparatus shown in FIG. 13. The present embodiment is an example showing a specific configuration of the semiconductor inspection apparatus shown in FIG. 1.

The semiconductor inspection apparatus in the present embodiment is provided with an observation part A, a control part B, and an analysis part C. Here the analysis part C is omitted from the illustration. A semiconductor device S as an inspected object is mounted on a stage 18 provided in the observation part A. Furthermore, in the present embodiment, the apparatus is equipped with a test fixture 19 for applying an electric signal necessary for inspection or the like to the semiconductor device S. The semiconductor device S is placed with its back side facing the objective lens 20.

The observation part A has a high-sensitivity camera 10 set in a black box (not shown), a laser scan optic (LSM: Laser Scanning Microscope) unit 12, optical systems 22, 24, an XYZ stage 15, an SIL 3, an SIL driver 30, and a correction ring driver 40.

Among these components, the camera 10 and LSM unit 12 correspond to the image acquisition part 1 in the configuration shown in FIG. 1. The optical systems 22, 24 correspond to the optical system 2. An objective lens 20 is located on the semiconductor device S side of the optical systems 22, 24. In the present embodiment, as shown in FIGS. 13 and 14, a plurality of objective lenses 20 having their respective magnifications different from each other are arranged to be switchable from one to another. An objective lens 20 is provided with two lens units 20a, 20b and a correction ring 21 as shown in FIG. 2 and is configured to be able to correct aberration by the correction ring driver 40. The test fixture 19 corresponds to the inspection part 16. The LSM unit 12 also has the function of the inspection part 16 in addition to the function of the image acquisition part 1.

The optical system 22 is a camera optical system for guiding light from the semiconductor device S incident through the objective lens 20, to the camera 10. The camera optical system 22 has an imaging lens 22a for focusing an image magnified at a predetermined magnification by an objective lens 20, on a light receiving surface inside the camera 10. A beam splitter 24a of the optical system 24 is interposed between objective lens 20 and imaging lens 22a. The high-sensitivity camera 10 can be, for example, a cooled CCD camera or the like.

In this configuration, the light from the semiconductor device S is guided through the optical system including the objective lens 20 and the camera optical system 22 to the camera 10. Then the camera 10 picks up an image such as a pattern image of the semiconductor device S. In another configuration, the camera can also picks up an emission image of the semiconductor device S. In this case, light emitted from the semiconductor device S in a voltage applied state by the test fixture 19 is guided through the optical system to the camera 10. Then the camera 10 picks up the emission image of the semiconductor device S to be used as an abnormality observation image. Specific examples of the emission from the semiconductor device S include one due to an abnormal portion based on a defect of the semiconductor device, transient emission with switching operation of a transistor in the semiconductor device, and so on. Furthermore, the acquired image may be an exothermic image based on a defect of device.

The LSM unit 12 has a laser beam introduction optical fiber 12a for irradiating an infrared laser beam, a collimator lens 12b for collimating the laser beam irradiated from the optical fiber 12a, into a parallel beam, a beam splitter 12e for reflecting the laser beam collimated into the parallel beam by the lens 12b, to change the optical path, and an XY scanner 12f for moving the laser beam reflected by the beam splitter 12e, in the XY directions to emit the laser beam toward the semiconductor device S.

The LSM unit 12 also has a condenser lens 12d for condensing light having been injected through the XY scanner 12f from the semiconductor device S side and having passed through the beam splitter 12e, and a detection optical fiber 12c for detecting the light condensed by the condenser lens 12d.

The optical system 24 is an LSM unit optical system for guiding light between the semiconductor device S and objective lens 20 and, the XY scanner 12f of the LSM unit 12. The LSM unit optical system 24 has a beam splitter 24a for reflecting part of light having been injected from the semiconductor device S through the objective lens 20, a mirror 24b for changing the optical path of the light reflected by the beam splitter 24a, to the optical path toward the LSM unit 12, and a lens 24c for condensing the light reflected by the mirror 24b.

In this configuration, the infrared laser beam emitted from a laser light source (not shown) and guided through the laser beam introduction optical fiber 12a travels via the lens 12b, beam splitter 12e, XY scanner 12f, optical system 24, and objective lens 20 onto the semiconductor device S and then enters the interior of the semiconductor device S.

Reflectively scattered light from the semi conductor device S with incidence of the incident light reflects a circuit pattern provided in the device surface of the semiconductor device S. The reflected light from the semiconductor device S travels through the optical path opposite to the incident light to reach the beam splitter 12e, and then passes through the beam splitter 12e. The light through the beam splitter 12e then travels through the lens 12d to enter the detection optical fiber 12c, and is detected by a photodetector coupled to the detection optical fiber 12c.

The intensity of the light detected through the detection optical fiber 12c by the photodetector is the intensity reflecting the circuit pattern provided in the semiconductor device S, as described above. Accordingly, while the infrared laser beam scans the semiconductor device S on the X-Y plane by the XY scanner 12f, a sharp image of the circuit pattern of the semiconductor device S or the like can be picked up.

The observation part A is further provided with the SIL 3. The SIL 3 is arranged movable between the aforementioned insertion position and standby position, relative to the high-sensitivity camera 10, LSM unit 12, optical systems 22, 24, and objective lens 20 and relative to the semiconductor device S mounted on the stage 18. The SIL driver 30 is provided for the SIL 3. The SIL driver 30 is comprised of an SIL moving device (SIL manipulator) to which an SIL holder for supporting the SIL 3 is coupled, and is an XYZ driving mechanism for moving the SIL 3 in the X, Y, and Z directions.

The control part B and analysis part C are provided for the observation part A for carrying out the observation and others for inspection of the semiconductor device S. In FIGS. 13 and 14, the analysis part C is omitted from the illustration.

The control part B has a camera controller 51a, an LSM controller 51b, an OBIRCH controller 51c, a stage controller 52, an SIL controller 53, and an objective lens controller 54. Among these, the stage controller 52, SIL controller 53, and objective lens controller 54 are as those described with FIG. 1, including the controls of focusing and aberration correction in the two control modes. The camera controller 51a, LSM controller 51b, and OBIRCH controller 51c correspond to the observation controller 51 in the configuration shown in FIG. 1.

The camera controller 51a and the LSM controller 51b control the operations of the high-sensitivity camera 10 and the LSM unit 12, respectively, thereby controlling the acquisition of an image of semiconductor device S carried out in the observation part A. The OBIRCH controller 51c is provided for acquiring an OBIRCH (Optical Beam Induced Resistance Change) image used in inspection of the semiconductor device S, and extracts a current change in the semiconductor device S appearing during a scan with the laser beam.

The analysis part C, as shown in FIG. 1, has an image analyzer 61 and an instructor 62, and is constructed, for example, of a computer or the like. Image information from the camera controller 51a and from the LSM controller 51b is entered through an image capture board provided in the computer of analysis part C.

A semiconductor inspection method with the semiconductor inspection apparatus shown in FIGS. 13 and 14 will be schematically described (cf. FIGS. 4 and 5). First, an observation of the semiconductor device S is carried out under the observation conditions after completion of the focusing and aberration correction in the first correction condition, in the normal mode in which the SIL 3 is located at the standby position (S200). Specifically, the semiconductor device S is scanned by the LSM unit 12 to acquire a pattern image thereof. An abnormality observation image used in detection of an abnormal portion in the semiconductor device S is also acquired. Specific examples of this abnormality observation image include an OBIRCH image acquired by the OBIRCH controller 51c, an emission image acquired by the camera 10, and so on. These pattern image and abnormality observation image are superimposed on each other, are displayed on the display device 63, etc. as occasion may demand. The acquired images are used to check an abnormal portion in the semiconductor device S, an abnormal portion detected is set as an inspection position, and the XYZ stage 15 and others are set so that the inspection position is located at the center of the field.

Then an observation of the semiconductor device S is carried out under the observation conditions after completion of the focusing and aberration correction in the second correction condition, in the SIL mode in which the SIL 3 is located at the insertion position corresponding to the inspection position of the semiconductor device S (S300). At this step, an enlarged pattern image, and an image such as an OBIRCH image or an emission image are acquired through the SIL 3 placed on the semiconductor device S and through the objective lens 20 and others. Superposition of the images, display thereof on the display device 63, etc. are carried out as occasion may demand. In acquisition of an emission image, the stage and others are properly moved so as to match the amount of chromatic aberration caused by the SIL 3, and the magnification is adjusted by software to implement superposition of images.

Figure 15:
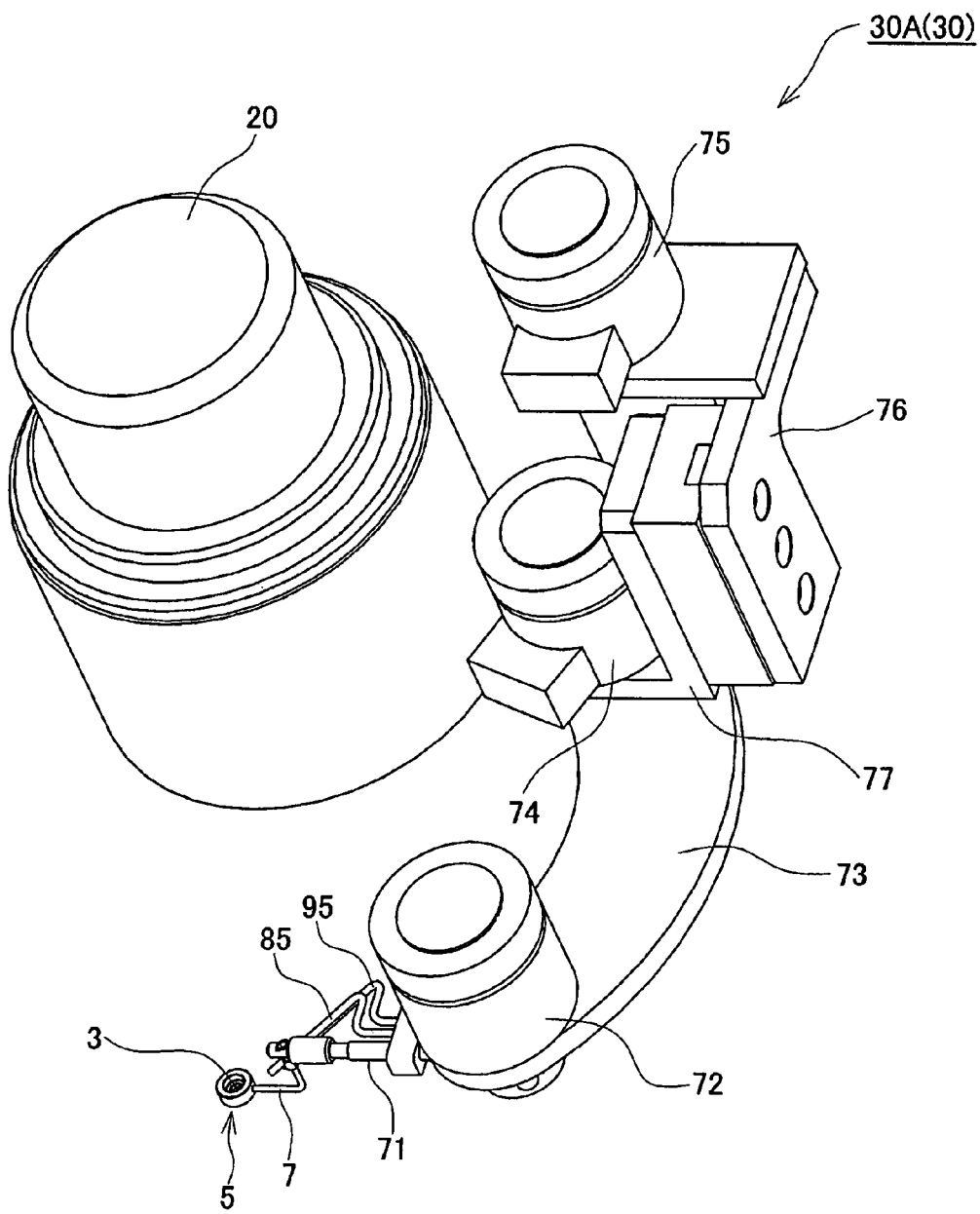
FIG. 15 is a perspective view from above an embodiment of an SIL manipulator and objective lens.

We will now explain a specific example of the solid immersion lens moving device (SIL moving device) used as the SIL driver 30 in the semiconductor inspection apparatus shown in FIGS. 13 and 14. FIG. 15 is a perspective view from above an SIL manipulator as an SIL moving device, and the objective lens.

The SIL 3 is supported by SIL holder 5. The SIL manipulator 30A (SIL driver 30) shown in FIG. 15 is an SIL moving device for driving the SIL 3 in the supported state by the SIL holder 5 in the three-dimensional directions to move the SIL 3 between the insertion position where the SIL 3 includes the optical axis to the objective lens 20 and is kept in close contact with the semiconductor device S, and the standby position off the optical axis. The SIL manipulator 30A in the present configuration example is further arranged to be also movable to a replacement position for replacement of the SIL 3 supported on the SIL holder 5.

Specifically, the SIL manipulator 30A has a first arm member 71 equipped with the SIL holder 5, a first arm member rotation source 72 for rotating the first arm member 71 in the X-Y plane (horizontal plane), a second arm member 73 for holding the first arm member rotation source 72, and a second arm member rotation source 74 for rotating the second arm member 73 in the X-Y plane. Furthermore, the SIL manipulator 30A has a Z-directional movement source 75 for moving the second arm member rotation source 74 in the Z direction perpendicular to the X-Y plane, this Z-directional movement source 75 is placed on the base end side, and the moving first arm member 71 is located on the terminal end side.

The Z-directional movement source 75 is comprised of a Z-axis motor or the like for moving a moving shaft in the Z direction, for example, by a feed screw or the like, and is mounted through a support portion 76 on the microscope part on the main body side of the inspection apparatus. This support portion 76 is detachably attached to the main body of the apparatus, for example, by screwing or the like, so as to achieve convenience in observation without the SIL manipulator 30A, in observation with another SIL moving device, and so on. The second arm member rotation source 74 is coupled through a support portion 77 to the moving shaft of the Z-directional movement source 75. This second arm member rotation source 74 is comprised, for example, of a motor with an output shaft being a rotational shaft to rotate in forward and backward directions (which can be arranged to rotate within a predetermined range), and is moved in the Z direction with driving of the Z-directional movement source 75.

One end of the second arm member 73 is coupled to the rotational shaft of the second arm member rotation source 74. This second arm member 73 is constructed in such curved shape that the second arm member 73 can readily recede from the field of the observation position of the semiconductor device S (the field of objective lens 20), as shown in FIG. 15. The first arm member rotation source 72 is fixed to the other end of this second arm member 73. This first arm member rotation source 72 is comprised, for example, of a motor with an output shaft being a rotational shaft to rotate in forward and backward directions (which can be arranged to rotate within a predetermined range).

As described above, the rotational shaft of the first arm member rotation source 72 is so located as not to be coaxial with the rotational shaft of the second arm member rotation source 74. With driving of the second arm member rotation source 74, the first arm member rotation source 72 is rotated together with the second arm member 73 in the X-Y plane and about a fulcrum at the rotational shaft of the second arm member rotation source 74. The other end of the aforementioned first arm member 71 is coupled to the rotational shaft of the first arm member rotation source 72. This first arm member 71 is rotated in the X-Y plane and about a fulcrum at the rotational shaft of the first arm member rotation source 72, with driving of the first arm member rotation source 72.

Figure 16:
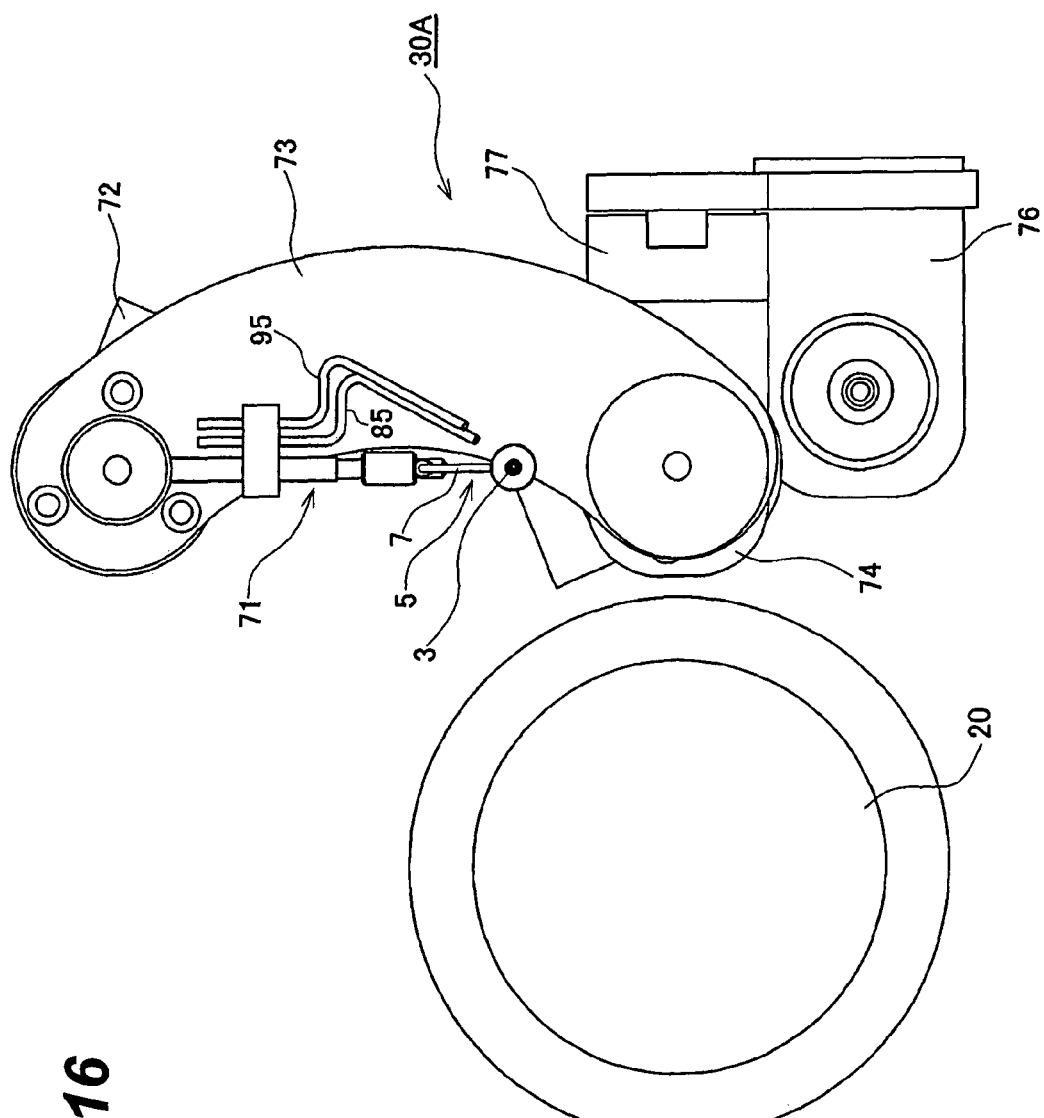
FIG. 16 is a bottom view showing the SIL manipulator and objective lens in a state in which the SIL is located at a standby position.
Figure 17:
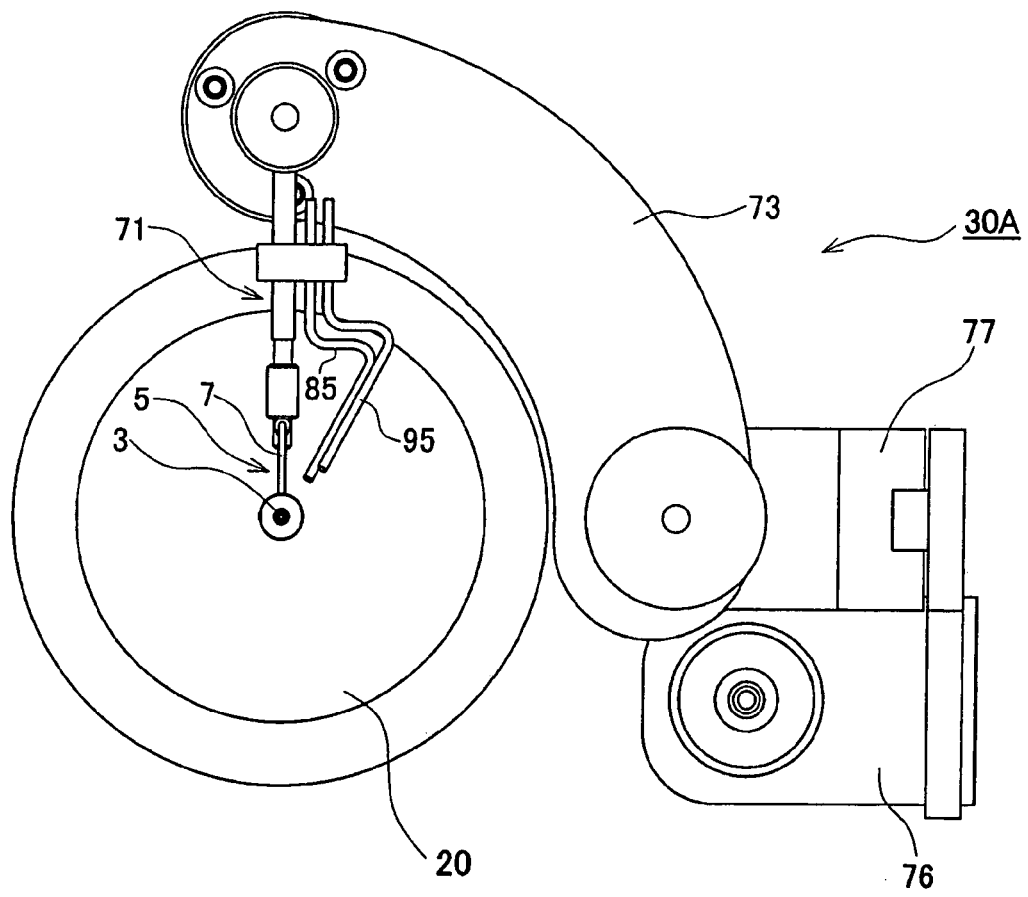
FIG. 17 is a bottom view showing the SIL manipulator and objective lens in a state in which the SIL is located at an insertion position.
Figure 18:
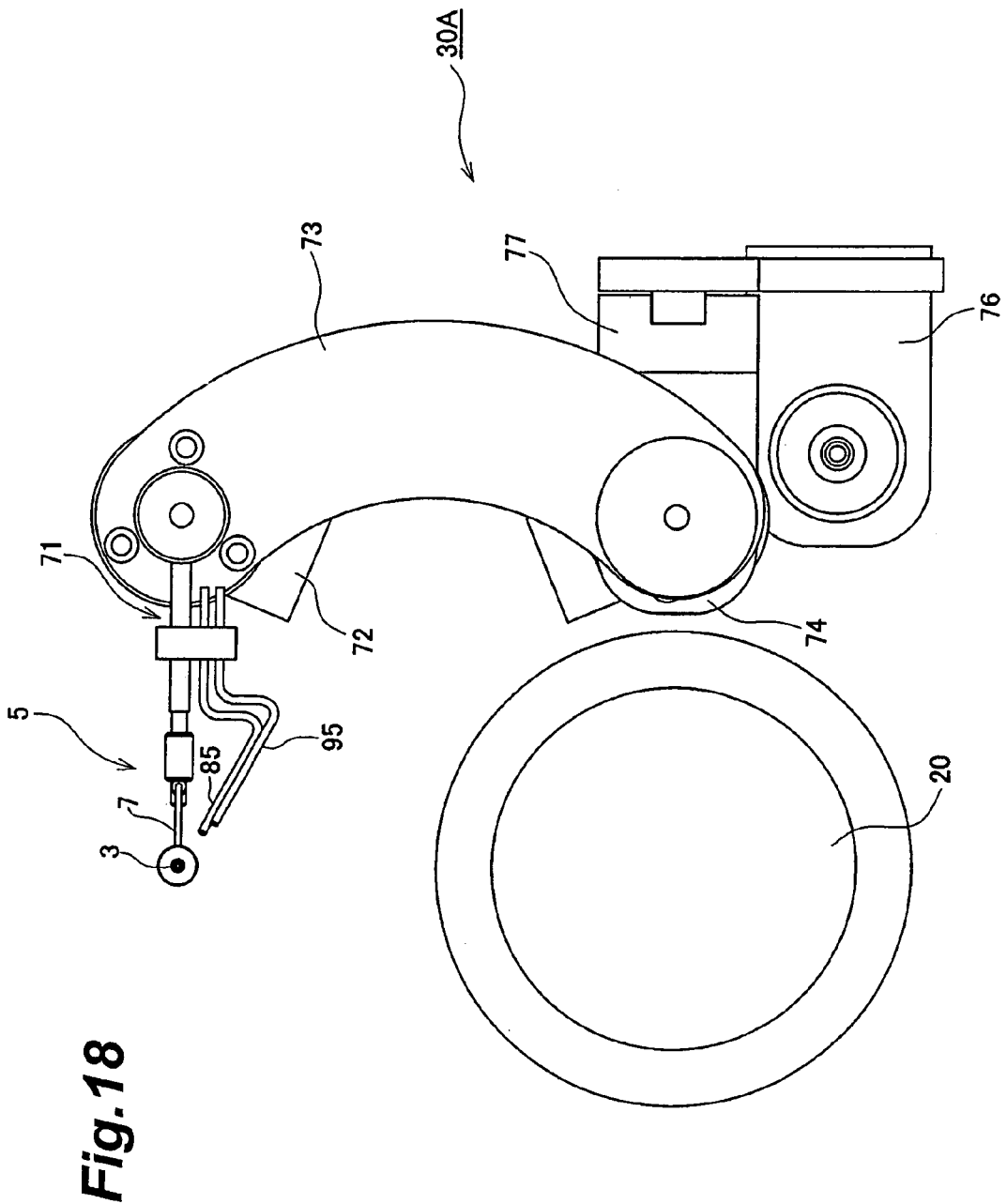
FIG. 18 is a bottom view showing the SIL manipulator and objective lens in a state in which the SIL is located at a replacement position.

In the above configuration, with driving of the first arm member rotation source 72 and the second arm member rotation source 74, the SIL 3 supported on the SIL holder 5 coupled to one end of the first arm member 71 is moved in a resultant direction of combination of their respective rotations in the X-Y plane. The SIL 3 is moved in the Z direction by driving of the Z-directional movement source 75. As a consequence, the SIL 3 is freely moved to any desired position in the three-dimensional directions. FIGS. 16 to 18 are bottom views each showing the SIL manipulator 30A and the objective lens 20, wherein FIG. 16 shows a state in which the SIL 3 is located at the standby position, FIG. 17 a state in which the SIL 3 is located at the insertion position, and FIG. 18 a state in which the SIL 3 is located at the replacement position.

The SIL manipulator 30A shown in FIG. 15 is provided with an optical coupling material supply pipe 85 for supplying an optical contact liquid to the SIL 3, and a gas supply pipe 95 for supplying a drying gas. These are used on the occasion of placing the SIL 3 at the insertion position and optically contacting the SIL 3 to the semiconductor device S.

Figure 19:
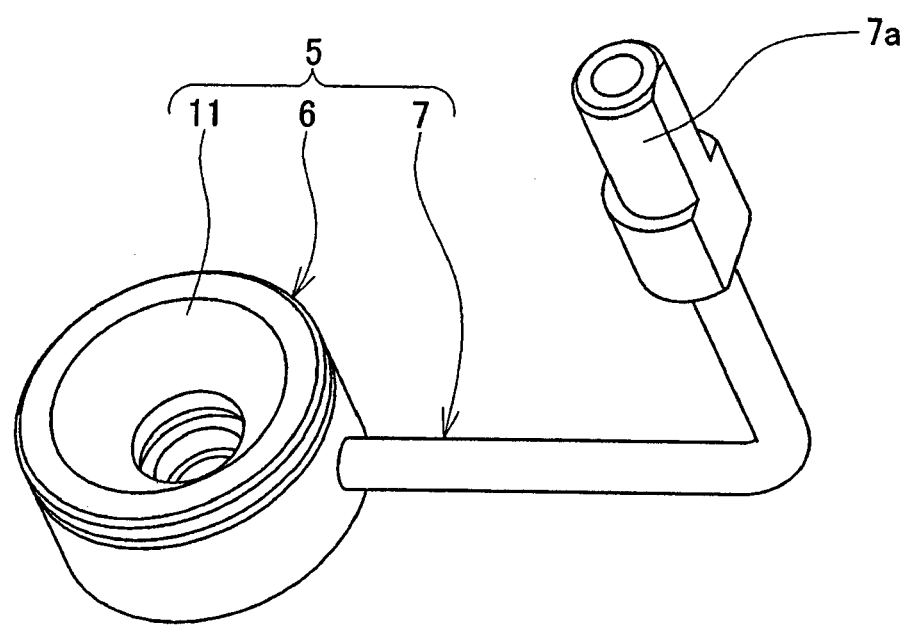
FIG. 19 is a perspective view showing a configuration of an SIL holder.

The SIL holder 5 for supporting the SIL 3 will be described. FIG. 19 is a perspective view showing a configuration of the SIL holder in the SIL manipulator shown in FIG. 15. FIG. 20 is a figure including vertical sectional views showing (a) a state of the SIL holder at the standby position and (b) a state of the SIL holder at the insertion position, respectively.

The SIL holder 5, as shown in FIG. 19, is provided with a holder 6 of nearly cylindrical shape for supporting the SIL 3, and an arm 7 for holding this holder 6. Since this SIL holder 5 can get into touch with the optical contact liquid, it is made of a material highly resistant to corrosion, for example, one of metals such as stainless steel, aluminum, etc., or a resin easy to be molded according to the lens shape, for example, acrylic resin, PET, polyethylene, polycarbonate, and so on.

The holder 6, as shown in FIGS. 20(a) and 20(b), is provided with a first holder 8 for holding the SIL 3, and a second holder 9 for supporting this first holder 8. These first holder 8 and second holder 9 are constructed in such nearly cylindrical shape as not to interfere with the optical path to the semiconductor device S.

The first holder 8 has an annular flange 8a projecting outward from the peripheral surface in the upper part thereof, and also has an annular flange 8b projecting inward in the bottom surface thereof. Then the SIL 3 is fixed and held on the first holder 8, for example, with an adhesive or the like in a state in which the bottom surface of the SIL 3 projects downward through an aperture formed in the inner circumference of the annular flange 8b. The second holder 9 has an annular flange 9a projecting inward in the bottom surface thereof. The annular flange 8a of the first holder 8 is mounted on the annular flange 9a of the second holder 9 in a state in which the bottom part of the first holder 8 projects downward through an aperture 9b formed in the inner circumference of the annular flange 9a, and the first holder 8 and SIL 3 are supported in the direction of weight on the second holder 9.

Since the dimensions are set in the relation of A<C<B herein where A represents the outside diameter of the lower part of the first holder 8, B the outside diameter of the annular flange 8a of the first holder 8, and C the inside diameter of the aperture 9b of the second holder 9, the first holder 8 is free relative to the second holder 9 and the first holder 8 is prevented from dropping off downward from the second holder 9.

The second holder 9 is provided with a cap 11 for retaining the SIL 3, which is mounted, for example, by fitting, meshing, or the like in an aperture 9c in the upper part thereof. This cap 11 is constructed in nearly cylindrical shape as the first holder 8 and the second holder 9 are, and dimensions are set in the relation of D<B where D represents the inside diameter of the cap 11. Accordingly, this cap 11 does not interfere with the optical path to the semiconductor device S, and prevents the first holder 8 holding the SIL 3 from dropping off, e.g., from jumping out through the aperture 9c in the upper part of the second holder 9, thereby preventing loss of the SIL.

The arm 7 is constructed by bending a round bar in nearly L-shape to extend outward from the second holder 9, one end thereof projects upward, and the other end is fixed to the side part of the second holder 9. At one end of this arm 7, an antirotation portion 7a, which contains a flat surface in part of a side face of a pipe, is fixed, for example, by fitting or the like so as to serve as a portion for preventing rotation of the arm 7 and holder 6. The arm 7 herein is constructed in nearly L-shape to extend upward at one end thereof, but it may also be constructed to extend within the X-Y plane. The arm 7 forming this SIL holder 5 is detachably coupled to one end of the first arm member 71 in the SIL manipulator 30A, as shown in FIG. 15.

In the SIL holder 5 and SIL manipulator 30A in the above configuration, the arm members 71, 73 are retracted in the state at the standby position shown in FIG. 16, so that the SIL 3 and arm members 71, 73 are outside the field of the objective lens 20. At this time, the first holder 8 holding the SIL 3 is in a state in which the annular flange 8a thereof is mounted on the annular flange 9a of the second holder 9 and in which the first holder 8 and SIL 3 are supported in the direction of weight on the second holder 9, as shown in FIG. 20(a).

When the SIL 3 is moved from this standby position to the insertion position, the arm members 71, 73 are first rotated to move the SIL 3 at the standby position to the position including the optical axis between the semiconductor device S and the objective lens 20, as shown in FIG. 17. At this time, since the second arm member 73 is constructed in curved shape, the second arm member 73 is readily located away from the field, without interfering with the field of the objective lens 20.

After the SIL 3 is brought into the field in this way, the Z-directional movement source 75 of the SIL manipulator 30A is driven to lower the SIL 3. When the SIL 3 is located near the observation position, the optical contact liquid is supplied through the optical coupling material supply pipe 85 and the SIL 3 is mounted on the observation position to be placed at the contact position (insertion position). When the SIL 3 is mounted at the insertion position on the semiconductor device S, the SIL 3 and first holder 8 supported in the direction of weight by the second holder 9 go into a lifted state by the semiconductor device S, as shown in FIG. 20(b). Furthermore, fine adjustment or the like for the position of the SIL 3 or the like is carried out in this state. An optical coupling material to be suitably used on this occasion can be an index matching fluid such as an index matching oil, or an optical contact liquid containing amphipathic molecules.

Since the SIL 3 and first holder 8 are free relative to the second holder 9 in the lifted state by the semiconductor device S, only the weight of the SIL 3 and first holder 8 acts at the observation position of the semiconductor device S. This prevents an excessive pressure from being applied to the semiconductor device, and the SIL 3 closely fits the semiconductor device at the observation position. Furthermore, the gas is supplied through the gas supply pipe 95 to dry the optical contact liquid, whereby the SIL 3 can be quickly and surely adhered to the semiconductor device S at the observation position.

For replacing the SIL 3 with another, the first arm member rotation source 72 of the SIL manipulator 30A is driven to rotate the first arm member 71, thereby moving the SIL 3 from the standby position to the replacement position shown in FIG. 18 and largely projecting the coupling part from near the position below the second arm member 73 to the outside. Then the SIL holder 5 with the arm 7 is replaced with another. This facilitates attachment and detachment of the arm 7 of the SIL holder 5 to and from the first arm member 71, and allows the SIL holder 5 together with the arm 7 to be replaced with another, whereby the lens replacement can be readily carried out without need for directly handling the small SIL 3.

The microscopes and sample observation methods according to the present invention are not limited to the above-described embodiments and configuration examples, but can be modified in various ways. For example, as to the specific configurations of the image acquisition part 1, optical system 2, inspection part 16, etc. in the above-stated semiconductor inspection apparatus and as to the specific inspection methods and others for inspection of the semiconductor device S, FIG. 13 and FIG. 14 show just an example of the configurations, but it is also possible to adopt a variety of configurations and inspection methods except for those. Where only the observation is carried out for various devices such as semiconductor devices, the apparatus may be constructed as a device observation apparatus without the inspection part 16. The image acquisition part 1 may also be excluded if not necessary, e.g., where the operator directly observes the image. The SIL driver 30 for driving the SIL 3 can also be implemented by a variety of mechanisms other than the SIL manipulator 30A shown in FIG. 15. It is also noted that the use of the above optical coupling material for achieving the optical contact between the SIL and the substrate is just an example, and another applicable method is to press the SIL against the substrate to achieve evanescent coupling.

The above embodiments described the semiconductor inspection apparatus and semiconductor inspection methods for the semiconductor device as an observed object, but the present invention can also be applied to cases where an observed object except for the semiconductor devices is used as a sample, as a microscope and a sample observation method used for observation of the sample at the predetermined observation plane and through the sample. This permits us to readily carry out the observation of the microstructure of the sample or the like in the observation of the sample. Specific examples of the sample in this case include, for example, various devices such as the aforementioned semiconductor devices and liquid crystal devices, or bio-related samples using a slide or the like.

The entry of the optical parameters of SIL for the correction tables can be implemented by individually entering values of parameters, or by any other method, for example, by a configuration of preparing a set of parameters corresponding to each model number of SIL, by a configuration of providing each SIL with a storage medium such as an IC chip storing values of parameters, and retrieving the data at a time of use, and so on, as described above.

For example, the entry of the optical parameters of SIL can be implemented by a configuration of providing the SIL, SIL holder, or arm with a storage medium of a semiconductor device, magnetic device, or the like, storing values of parameters such as a model number, serial number, curvature radius, thickness, and refractive index. Specific examples of the method for retrieving the parameter data in this configuration include a method of receiving the data by radio wave, a method of receiving the data via electric contact through the arm and SIL manipulator, and the like. Alternatively, a configuration of providing the SIL holder with a bar code, and reading the parameter data by image recognition of the bar code can be used.

In addition, a configuration of providing the SIL holder with a mark for recognizing the individual SIL with the naked eye or by using the image can be used. Specific examples of the method for retrieving the parameter data by using the above-mentioned mark include a method of reading the data by using a number or color of lines, points, color of the holder itself, serial number, or the like. In this case, it is possible to use a method of recognizing ID of the SIL by the mark, specifying the serial number, and retrieving the parameter data such as a curvature radius, thickness, and refractive index registered in the software. The above parameter data corresponding to the SIL serial number can be provided by a flexible disk or the like, and registered beforehand in the software.

Further, in the microscope of the above configuration, the SIL is driven by the solid immersion lens driving means, however, the microscope can be configured without the solid immersion lens driving means, if it is unnecessary. In this case, the controlling means for controlling the objective lens driving means may be configured to have at least the SIL mode, as the control mode, in which the focusing and aberration correction are carried out under the correction condition set based on a refractive index $n_0$ of the sample and a thickness $t_0$ of the sample up to the observation plane, and a refractive index $n_1$, a thickness $d_1$, and a radius of curvature $R_1$ of the solid immersion lens.

In the above embodiments, the focusing and aberration correction are carried out respectively in the normal mode and the SIL mode. However, as for the normal mode only with the objective lens, the focusing may be carried out without the aberration correction in the normal mode. In this case, if the correction tables are used in the normal mode, the controlling means may be configured to comprise only the focusing table for the normal mode, and without the aberration correction table.

As to the optical system 2 including the objective lens 20, it is possible to adopt a variety of configurations in addition to the above configurations. For example, the optical system 2 may be configured to have, as the objective lens 20, a first objective lens for observing a normal image of the sample in the normal mode, and a second objective lens for observing an enlarged image of the sample with the SIL 3 in the SIL mode.

A specific example of such a configuration is that, in the case that a plurality of objective lenses 20 are arranged to be switchable by using a revolver as shown in FIG. 13, one of these objective lenses is used as the objective lens for the normal mode, and another objective lens to which the SIL 3 is attached is used as the objective lens for the SIL mode. In this configuration, the revolver for switching the objective lenses functions as the solid immersion lens driving means. Further, in the above case, an objective lens without a correction ring (cf. FIGS. 1 and 2) can be used as the objective lens for the normal mode, if the aberration correction is unnecessary.

An example of a sample observation method in the case of using the different objective lenses in the normal mode and the SIL mode will be described. First, a treatment with a washing liquid and contact liquid is carried out for improving the close contact characteristics of the sample surface, and then, the pattern image of the normal image of the sample is observed by using the normal objective lens. In addition, the abnormality observation image (for example the optical image due to the defect) is observed. Subsequently, a portion to be observed is set at the center, and the pattern image and the abnormality observation image are similarly observed with the normal objective lens with a higher magnification. Further, the magnification of the objective lens is raised up to about x20, and the observation position is set at the center.

Next, the optical system is moved slightly away from the sample, the objective lens is switched into the objective lens to which the SIL is attached, and then, the optical system is slowly moved to the sample side. When the front end of the SIL comes in contact with the sample, a contact sensor is brought into ON state, and SIL is moved from the ON position to the actual focus position. Here, a distance from the ON position to the actual focus position is previously set.

Further, a fine adjustment of the focusing condition is carried out with observing the pattern image of the sample by using the SIL-attached objective lens, and then, the pattern image and the abnormality observation image of the enlarged images of the sample are observed. Here, in the case that the observation of the normal image is again carried out, the optical system is moved away from the sample, the objective lens is switched into the normal objective lens, and then the optical system is moved to the focus position.

The microscope described above is configured as a microscope for observing a sample at a predetermined observation plane, comprising: (1) an optical system comprising an objective lens and adapted to guide an image of the sample; (2) objective lens driving means for driving the objective lens to achieve focusing and aberration correction for the sample; (3) a solid immersion lens arranged at a position including an optical axis from the sample to the optical system; and (4) controlling means for controlling the objective lens driving means, wherein (5) the controlling means has a solid immersion lens mode, as a control mode, in which the focusing and aberration correction are carried out under a correction condition set based on a refractive index $n_0$ of the sample and a thickness $t_0$ of the sample up to the observation plane, and a refractive index $n_1$, a thickness $d_1$, and a radius of curvature $R_1$ of the solid immersion lens.

The sample observation method described above is configured as a sample observation method of observing a sample at a predetermined observation plane and through an optical system comprising an objective lens, the sample observation method comprising: (a) a correction step of placing a solid immersion lens at an insertion position including an optical axis from the sample to the optical system and carrying out focusing and aberration correction under a correction condition set based on a refractive index $n_0$ of the sample and a thickness $t_0$ of the sample up to the observation plane, and a refractive index $n_1$, a thickness $d_1$, and a radius of curvature $R_1$ of the solid immersion lens; and (b) an enlarged image observation step of observing an enlarged image of the sample in a state after completion of the focusing and aberration correction in the correction step.

Here, the microscope may be configured to comprise solid immersion lens driving means for driving the solid immersion lens to move the solid immersion lens between an insertion position including an optical axis from the sample to the optical system and a standby position off the optical axis. Using the solid immersion lens driving means makes it feasible to readily acquire the normal image/the enlarged image in the absence/in the presence of the solid immersion lens, respectively. Further, the sample observation method may be configured to comprise a normal image observation step of observing a normal image of the sample in a state of placing the solid immersion lens at a standby position off the optical axis.

Further, the optical system may be configured to have, as the objective lens, a first objective lens for observing a normal image of the sample, and a second objective lens for observing an enlarged image of the sample with the solid immersion lens. In the configuration with the different objective lenses for the observations in the absence/in the presence of the solid immersion lens, a revolver for switching the objective lenses functions as the above solid immersion lens driving means.

In addition, it is preferable that, in the microscope, the controlling means has two control modes, a normal mode in which the focusing is carried out by changing a distance between the sample and the objective lens, and the solid immersion lens mode. Further, the microscope is preferably configured so that in the normal mode, the focusing is carried out under a normal correction condition set based on the refractive index $n_0$ of the sample and the thickness $t_0$ of the sample up to the observation plane. Similarly, it is preferable that the sample observation method comprises a normal correction step of placing the solid immersion lens at the standby position off the optical axis from the sample to the objective lens and carrying out focusing by changing a distance between the sample and the objective lens. Further, the sample observation method is preferably configured so that in the normal correction step, the focusing is carried out under a normal correction condition set based on the refractive index $n_0$ of the sample and the thickness $t_0$ of the sample up to the observation plane. In the normal mode, the aberration correction may be carried out in addition to the focusing if necessary, as in the solid immersion lens mode.

The microscope and sample observation method described above are configured to perform the observation of the sample on the basis of a switchover between the first mode (normal mode) of carrying out the observation under the observation condition set in view of the optical parameters of the sample in the absence of the solid immersion lens, and the second mode (solid immersion lens mode) of carrying out the observation under the observation condition set in view of the optical parameters of the sample and the solid immersion lens in the presence of the solid immersion lens. This makes it feasible to suitably acquire the normal image/the enlarged image in the absence/in the presence of the solid immersion lens, respectively, and thus to readily perform the observation of the microstructure of the sample and the like.

Concerning the focusing for the sample, the microscope is preferably configured so that the objective lens driving means comprises focusing means for changing a distance between the sample and the objective lens to carry out the focusing. Likewise, the sample observation method is preferably configured so that in the correction step, the focusing is carried out by changing a distance between the sample and the objective lens.

Concerning the aberration correction, the microscope is preferably configured so that the objective lens comprises a first lens unit and a second lens unit arranged along the optical axis, and so that the objective lens driving means comprises aberration correcting means for changing a spacing between the first lens unit and the second lens unit to carry out the aberration correction. Similarly, the sample observation method is preferably configured so that in the correction step, the aberration correction is carried out by changing a spacing between a first lens unit and a second lens unit arranged along the optical axis in the objective lens.

As a specific correction method, the microscope is preferably configured so that the controlling means comprises a focusing table and an aberration correction table corresponding to the correction condition in the solid immersion lens mode. Similarly, the sample observation method is preferably configured so that the correction step is arranged to use a focusing table and an aberration correction table corresponding to the correction condition.

In the configuration that the switching of the observations in the absence/in the presence of the solid immersion lens is carried out, the microscope is preferably configured so that the controlling means comprises a focusing table (first focusing table) corresponding to the normal correction condition (first correction condition) in the normal mode (first mode), and a focusing table (second focusing table) and an aberration correction table (second aberration correction table) corresponding to the correction condition (second correction condition) in the solid immersion lens mode (second mode). In this case, if the aberration correction in the normal mode is necessary, it is preferable that the controlling means further comprises an aberration correction table (first aberration correction table) corresponding to the correction condition in the normal mode.

Similarly, the sample observation method is preferably configured so that the normal correction step (first correction step) is arranged to use a focusing table (first focusing table) corresponding to the normal correction condition (first correction condition), and the correction step (second correction step) is arranged to use a focusing table (second focusing table) and an aberration correction table (second aberration correction table) corresponding to the correction condition (second correction condition). In this case, if the aberration correction in the normal correction step is necessary, it is preferable that the normal correction step is further arranged to use an aberration correction table (first aberration correction table) corresponding to the correction condition.

By using the focusing tables and aberration correction tables in this manner, it becomes feasible to readily and surely perform the focusing and aberration correction.

The microscope is preferably configured so that the solid immersion lens driving means is a solid immersion lens moving device comprising: a first arm member to which a solid immersion lens holder for supporting the solid immersion lens is coupled; a first arm member rotation source for rotating the first arm member in a horizontal plane substantially parallel to the sample; a second arm member for holding the first arm member rotation source; and a second arm member rotation source for rotating the second arm member in the horizontal plane and around a rotational axis at a position not coaxial with a rotational axis of the first arm member rotation source.

Using this solid immersion lens moving device, the solid immersion lens can be suitably moved between the insertion position and the standby position, relative to the sample, such as a semiconductor device, and to the objective lens. In this case, further, the solid immersion lens moving device preferably comprises a vertical movement source for moving the second arm member rotation source in a vertical direction perpendicular to the horizontal plane.

Alternatively, as described later, the microscope is preferably configured so that the microscope comprises a solid immersion lens holder including a base part to be attached to the objective lens, and a lens holding part provided with the base part, extending in a direction of the optical axis of the objective lens, and holding the solid immersion lens at an end portion thereof, wherein the lens holding part holds the solid immersion lens so that light emerging from the solid immersion lens to the base part side travels through a region outside the lens holding part and toward the base part, and wherein the base part has a light passing portion which transmits the light emerging from the solid immersion lens to the base part side, toward the objective lens.

In this case, it is preferable that the lens holding part has: a holding member extending in the direction of the optical axis and receiving the solid immersion lens; and a lens cover provided at an end portion of the holding member and having an opening for exposing a bottom surface of the solid immersion lens to the outside, wherein the lens holding part houses the solid immersion lens between the holding member and the lens cover.

The microscope and sample observation method according to the present invention can be applied as a microscope and a sample observation method capable of readily observing a sample necessary for an analysis of microstructure of a semiconductor device or the like. Namely, the present invention provides the microscope and sample observation method capable of readily performing the observation of microstructure of a sample or the like, by carrying out the observation of the sample at the predetermined observation plane and through the sample, by using the solid immersion lens mode of carrying out the observation in consideration of the optical parameters of the sample and solid immersion lens with the solid immersion lens at the insertion position including the optical axis from the sample to the objective lens.

Next, the solid immersion lens holder according to the present invention will be described below. Here, it should be noted that the solid immersion lens holder described below can be suitably applied to the above-described microscope and the sample observation method.

A solid immersion lens (SIL) is known as a lens for enlarging an image of an observation object. This solid immersion lens is a lens of a hemispherical shape or a superhemispherical shape called a Weierstrass sphere, and microscopic lens in the size of about 1 mm-5 mm. When this solid immersion lens is set in close contact with a surface of the observation object, the numerical aperture (NA) and magnification both are increased, so as to enable observation with a high spatial resolution.

One of the known techniques for securely keeping this solid immersion lens in close contact with the observation object is, for example, the one described in Document 1: U.S. Pat. No. 6,621,275. In the semiconductor inspection system described in Document 1, the solid immersion lens is mounted through a solid immersion lens holder in front of an objective lens (i.e., on the observation object side). The solid immersion lens holder has a chamber with a valve at an end portion thereof, and houses the solid immersion lens in the chamber. The pressure inside the chamber is regulated through this valve to move the solid immersion lens in the direction of the optical axis thereof to achieve optical coupling between the observation object and the solid immersion lens.

The outer shape of this solid immersion lens holder is a tapered shape the inner diameter of which decreases from the objective lens side toward the solid immersion lens side, and a light beam from the solid immersion lens passes the interior of the solid immersion lens holder to enter the objective lens.

However, if the solid immersion lens is held by the solid immersion lens holder of the tapered shape with the solid immersion lens at the top as in the semiconductor inspection system described in Document 1, there will arise a problem as described below, where an IC (semiconductor device) as an observation object is housed in a socket or where a mold IC package having an IC molded with resin is inspected.

Namely, for example, in the case of an example in which an IC in a mold IC package (sample) is observed, the IC as a semiconductor device is buried in a plastic mold and, for observing the IC, the mold part is removed to expose the back surface of the IC. In this case, the IC as an observation object is located on a bottom surface of a recess. For this reason, where the solid immersion lens holder is of the tapered shape, there can occur contact (interference) between the side wall of the recess and the outer peripheral surface of the solid immersion lens holder in the vicinity of the peripheral part of the IC. This results in posing a problem that the region near the peripheral part of the IC cannot be observed.

Therefore, an object of the present invention is to provide a solid immersion lens holder permitting observation up to a region closer to the peripheral part of the observation object even in the case where the observation object is placed in a recess of a sample.

In order to solve the above problem, a solid immersion lens holder according to the present invention is a solid immersion lens holder comprising: a base part to be attached to an objective lens; and a lens holding part provided with the base part, extending in a direction of an optical axis of the objective lens, and holding a solid immersion lens at an end portion thereof, wherein the lens holding part holds the solid immersion lens so that light emerging from the solid immersion lens to the base part side travels through a region outside the lens holding part and toward the base part, and wherein the base part has a light passing portion which transmits the light emerging from the solid immersion lens to the base part side, toward the objective lens.

In this case, the light passing portion is formed in the base part and thus the light beam from the solid immersion lens can be securely guided into the objective lens. For this reason, the observation object can be observed even in a state in which the solid immersion lens is held by the lens holding part. Since the solid immersion lens is held by the lens holding part extending in the direction of the optical axis of the objective lens, for example, during observation of the observation object located on a bottom surface of a recess, the lens holding part is prevented from coming into contact with the side wall of the recess even if the solid immersion lens is moved to the vicinity of the peripheral part of the observation object. As a result, it becomes feasible to observe the peripheral part of the observation object.

In a preferred configuration of the above-described solid immersion lens holder, the lens holding part has: a holding member extending in the direction of the optical axis and receiving the solid immersion lens; and a lens cover provided at an end portion of the holding member and having an opening for exposing a bottom surface of the solid immersion lens to the outside; the lens holding part houses the solid immersion lens between the holding member and the lens cover. The bottom surface of the solid immersion lens means a surface to be brought into contact with the observation object.

In this configuration, the solid immersion lens is housed between a lens receiver of the holding member, and the lens cover, whereby the solid immersion lens is prevented from slipping off the lens holding part.

In the above-described solid immersion lens holder, preferably, the holding member has a plurality of lens receivers for receiving the solid immersion lens. This permits the solid immersion lens to be held in a stabler state. Since the solid immersion lens is received by the plurality of lens receivers, it is feasible to allow the light to propagate from the solid immersion lens to the base part side, between the lens receivers.

In the above-described solid immersion lens holder, preferably, the plurality of lens receivers are radially arranged with respect to a center line of the holding member. In this configuration, the plurality of lens receivers are arranged apart in the circumferential direction, and thus partially receive the surface of the solid immersion lens on the holding member side. For this reason, the light can be made to securely emerge from the solid immersion lens to the base part side even in a state in which the solid immersion lens is received by the lens receivers.

In a further preferred configuration, the plurality of lens receivers are arranged apart from each other with respect to the center line of the holding member. This enables the light even along the center line of the holding member to enter the objective lens, and it is thus feasible to effectively use the light emerging from the solid immersion lens to the base part side.

In the above-described solid immersion lens holder, preferably, the lens holding part has a clearance with respect to the solid immersion lens. This permits the solid immersion lens to follow the surface shape of the observation object, and it results in bringing the solid immersion lens into closer contact with the observation object.

Furthermore, the light passing portion of the above-described solid immersion lens holder can be an aperture. In this case, preferably, an end of the lens holding part on the base part side is located in the aperture, and the base part has a connecting part for connecting the lens holding part to the base part. In this configuration, the lens holding part and the base part are securely coupled to each other by the connecting part even if the lens holding part is located in the aperture.

The lens holding part of the above-described solid immersion lens holder is preferably provided integrally with the base part. In this case, it becomes easy to produce the solid immersion lens holder.

Furthermore, the light passing portion of the above-described solid immersion lens holder may have a light passing member.

In another configuration, the above-described solid immersion lens holder preferably further comprises a diaphragm provided in the base part and arranged to limit a beam passing the light passing portion. In this case, the observation object can be observed through the use of a beam in a desired size. Since the diaphragm permits us, for example, to change the size of the beam emerging from the objective lens and entering the solid immersion lens, it becomes feasible to regulate the numerical aperture (NA) of the beam entering the observation object, and, as a result, it becomes feasible to observe the observation object with a desired NA.

Preferably, the above-described solid immersion lens holder is configured so as to protect the observation object to be observed through the solid immersion lens, in accordance with a stress exerted on the solid immersion lens.

It is necessary to keep the solid immersion lens in close contact with the observation object during observation of the observation object through the solid immersion lens, but if the solid immersion lens is pressed against the observation object with too high pressure, the observation object can be damaged. When the solid immersion lens is pressed against the observation object, the solid immersion lens receives a reaction force, and it results in exerting a stress on the lens holding part holding the solid immersion lens. For this reason, by protecting the observation object in accordance with the stress exerted on the lens holding part, it is feasible to observe the observation object through the use of the solid immersion lens held by the solid immersion lens holder, without damage to the observation object.

In a further preferred configuration, the above-described solid immersion lens holder further comprises a stress detection sensor for detecting a stress exerted on the solid immersion lens.

In this case, the stress detection sensor detects the stress exerted on the lens holding part, and it is thus feasible to keep the solid immersion lens in close contact with the observation object, without damage to the observation object.

Another solid immersion lens holder according to the present invention is a solid immersion lens holder for holding a solid immersion lens to be used in observation of an observation object placed in a recess of a sample, the solid immersion lens holder being attached to an objective lens, holding the solid immersion lens so as to avoid contact with a side wall of the recess during observation of a peripheral part of the observation object, and transmitting light emerging from the solid immersion lens to the objective lens side, toward the objective lens.

Since this configuration permits the light emerging from the solid immersion lens to the objective lens side to be transmitted while the solid immersion lens holder holds the solid immersion lens, it is feasible to observe the observation object. Since the solid immersion lens holder holds the solid immersion lens so as to avoid contact with the side wall of the recess during the observation of the peripheral part of the observation object, it is feasible to securely observe the peripheral part of the observation object located in the recess.

The solid immersion lens holder according to the present invention permits us to observe a region closer to the peripheral edge of the observation object even in the case where the observation object is located inside the recess.

The preferred embodiments of the solid immersion lens holder according to the present invention will be described below with reference to the drawings. The same elements will be denoted by the same reference symbols in each of drawings, without redundant description.

First Embodiment

Figure 21:
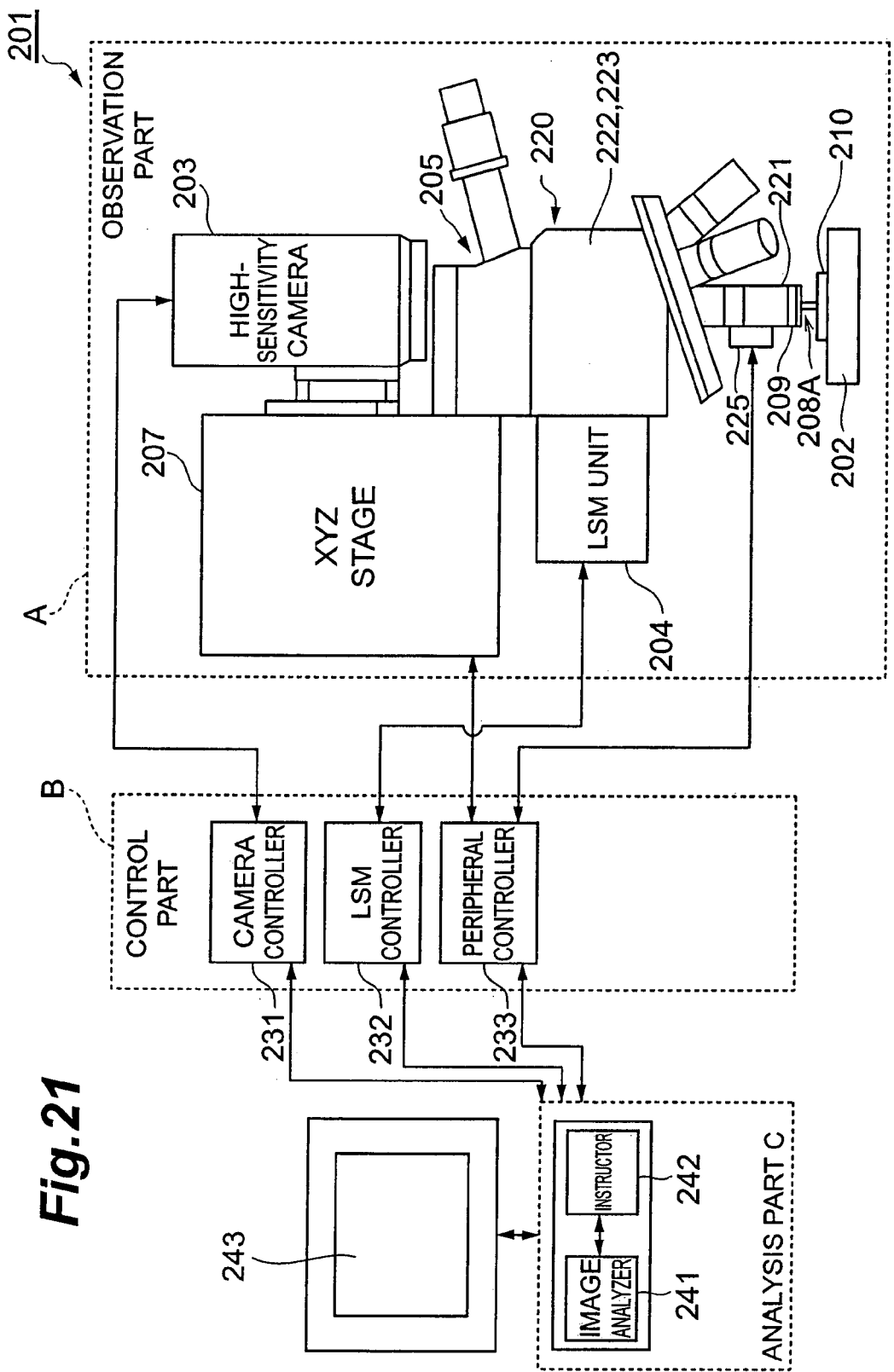
FIG. 21 is a configuration diagram of a semiconductor inspection apparatus to which an embodiment of the solid immersion lens holder is applied.
Figure 22:
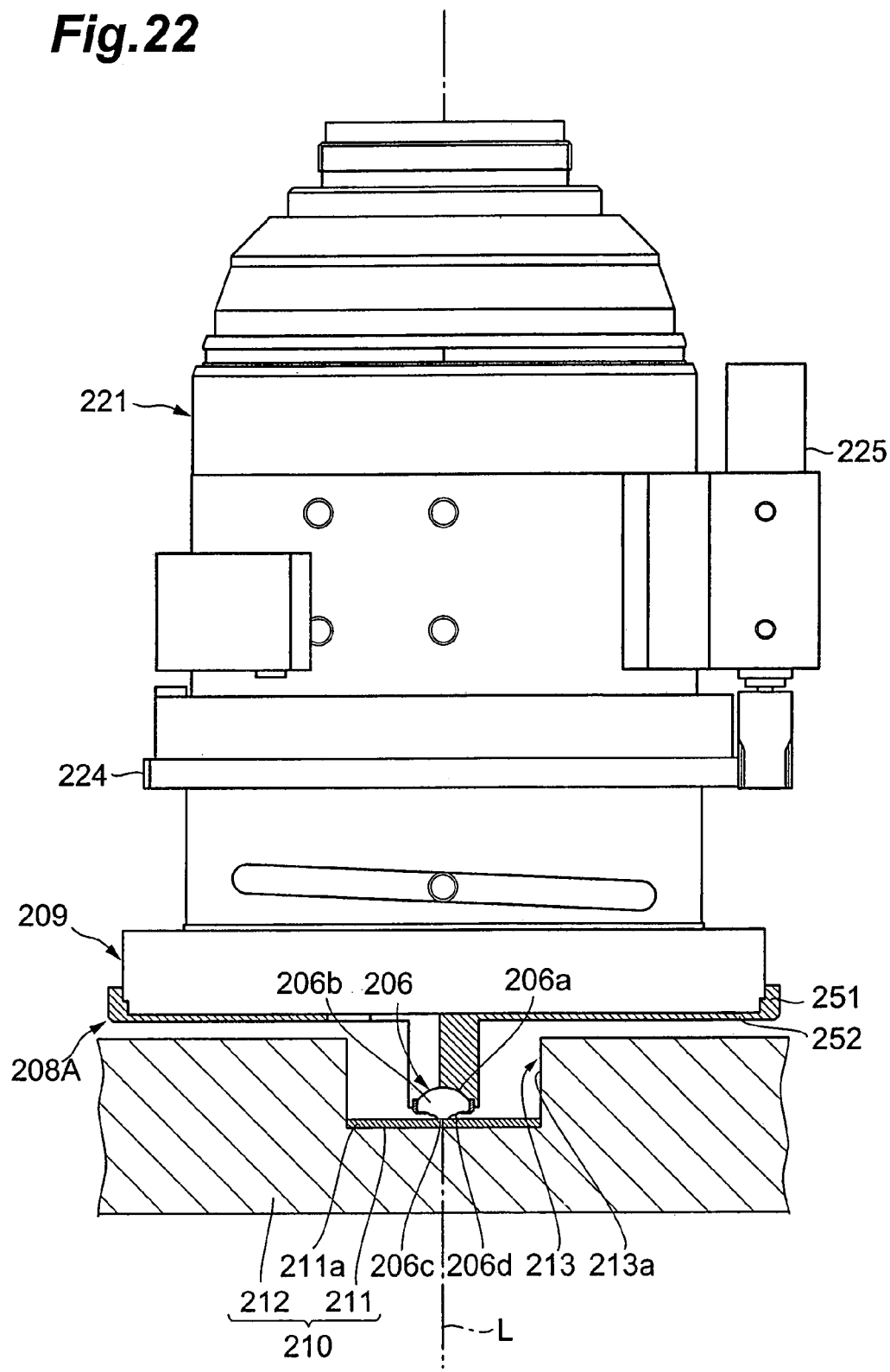
FIG. 22 is a configuration diagram showing a configuration of the solid immersion lens holder.
Figure 23:
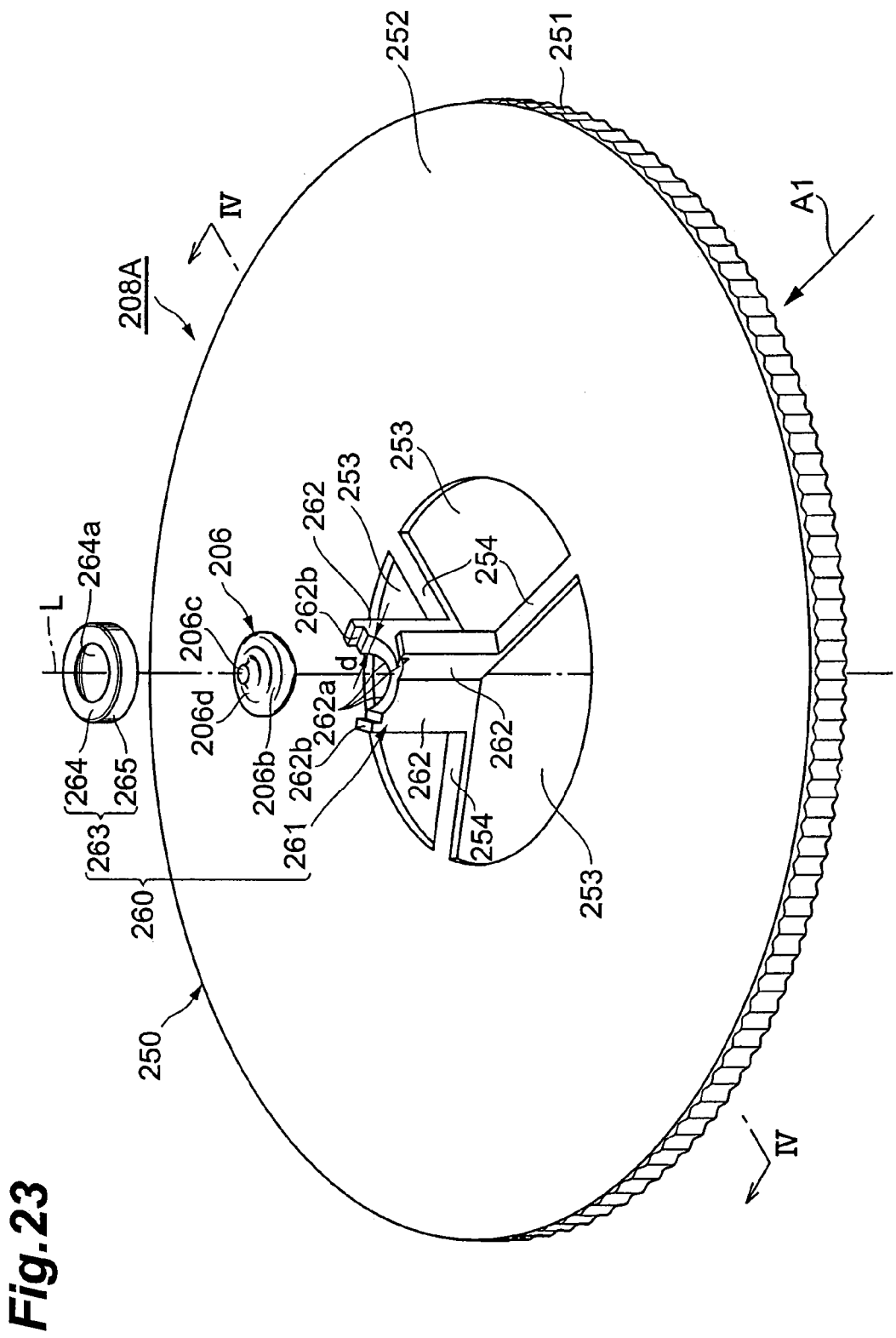
FIG. 23 is an exploded perspective view of the solid immersion lens holder shown in FIG. 22.

FIG. 21 is a configuration diagram showing a semiconductor inspection apparatus provided with the solid immersion lens holder according to the first embodiment of the present invention. FIG. 22 is a configuration diagram showing a configuration of the solid immersion lens holder. FIG. 23 is an exploded perspective view of the solid immersion lens holder. FIG. 24(a) is a sectional view along line IV-IV in FIG. 23, and FIG. 24(b) an enlarged view of an end portion of a lens holding part in the solid immersion lens holder shown in FIG. 24(a). FIG. 22 shows a state in observation of a sample while the solid immersion lens holder is mounted on an objective lens. FIGS. 23, 24(a), and 24(b) show a state in which the solid immersion lens holder holds a solid immersion lens. FIG. 24(b) shows a state in which the solid immersion lens is pressed against an observation object.

As shown in FIGS. 21 and 22, the semiconductor inspection apparatus 201 is, for example, a inspection device that inspects as an observation object a semiconductor device 211 (cf. FIG. 22) in a mold semiconductor device being a sample 210 and that is arranged to acquire an image of the semiconductor device 211 and to inspect internal information thereof.

The "mold semiconductor device" is a device in which the semiconductor device 211 is hermetically sealed as molded with resin 212. The "internal information" includes a circuit pattern of the semiconductor device and very weak emission from the semiconductor device. Examples of this very weak emission include emission from an abnormal part based on a defect of the semiconductor device, transient emission with a switching operation of a transistor in the semiconductor device, and so on. Furthermore, the very weak emission also includes heat generated based on a defect of the semiconductor device.

The sample 210 is mounted on a stage 202 in an observation part A and with the back surface of the semiconductor device 211 facing up, in a state in which the resin 212 is cut away so as to expose the back surface of the semiconductor device 211 buried in the resin 212. Since the back surface of the semiconductor device 211 is exposed by cutting the sample 210 in part away in this manner, the semiconductor device 211 is located on a bottom surface of recess 213 resulting from the cutting of the resin 212. Then the inspection apparatus 201, in the present embodiment, inspects the illustrated lower surface of the semiconductor device 211 (an integrated circuit formed on a front surface of a substrate of semiconductor device 211, or the like).

The semiconductor inspection apparatus 201 is provided with an observation part A for observation of semiconductor device 211, a control part B for control on operations of respective parts in the observation part A, and an analysis part C for processing, instructions, etc. necessary for inspection of semiconductor device 211.

The observation part. A is provided with a high-sensitivity camera 203 and a laser scan optic (LSM: Laser Scanning Microscope) unit 204 as image acquiring means for acquiring an image from the semiconductor device 211, an optical system 220 including objective lens 221 of microscope 205 disposed between the high-sensitivity camera 203 and LSM unit 204, and the semiconductor device 211, a solid immersion lens 206 (cf. FIG. 22) for acquiring an enlarged observation image of semiconductor device 211, and an XYZ stage 207 for moving these members each in X-Y-Z directions orthogonal to each other.

The optical system 220 is provided with an optical system 222 for the camera and an optical system 223 for the LSM unit, in addition to objective lens 221. There are a plurality of objective lenses 221 with different magnifications provided so as to be switchable. The objective lens 221 has a correction ring 224 to permit an observer to adjust the correction ring 224 so as to securely achieve focus on a location desired to observe. The camera optical system 222 guides light from the semiconductor device 211 through the objective lens 221, to the high-sensitivity camera 203, and the high-sensitivity camera 203 acquires an image of a circuit pattern or the like of the semiconductor device 211.

On the other hand, the LSM unit optical system 223 reflects an infrared laser beam from the LSM unit 204 toward the objective lens 221 by a beam splitter (not shown) to guide the beam to the semiconductor device 211, and guides the reflected laser beam traveling from the semiconductor device 211 toward the high-sensitivity camera 203 through the objective lens 221, to the LSM unit 204.

This LSM unit 204 emits the infrared laser beam toward the semiconductor device 211 while scanning it in the X-Y directions, and detects the reflected light from the semiconductor device 211 by a photodetector (not shown). The intensity of this detected light is one reflecting the circuit pattern of the semiconductor device 211. Therefore, the LSM unit 204 acquires an image of the circuit pattern of the semiconductor device 211 or the like by the X-Y scan on the semiconductor device 211 with the infrared laser beam.

The XYZ stage 207 is a mechanism for moving the high-sensitivity camera 203, LSM unit 204, optical system 220, solid immersion lens 206, etc. in each of the X-Y directions (horizontal directions; directions parallel to the semiconductor device 211 as an observation object) and the Z-direction (vertical direction) orthogonal to them, according to need.

As shown in FIG. 22, the solid immersion lens 206 is a microscopic lens of hemispherical shape and has a hemispherical part 206b having an upper surface 206a being an input/output surface for light to the outside (e.g., the objective lens of the microscope) and formed in the spherical shape. The solid immersion lens 206 has a convex part 206d that is protruded in the opposite direction to the upper surface 206a side and in the central region of the solid immersion lens 206 and that has a bottom surface 206c formed in planar shape. This bottom surface 206c is a mount surface onto the semiconductor device 211. The solid immersion lens 206 is arranged so that the bottom surface 206c is brought into close contact with an observation position (on the illustrated upper surface) for observation to acquire an enlarged observation image of the front surface (illustrated lower surface) of the semiconductor device 211 being the back side. Specifically, the solid immersion lens used in the semiconductor inspection apparatus is made of a high-index material having a refractive index substantially equal to or close to the refractive index of the substrate material of the semiconductor device. Typical examples of the material include Si, GaP, GaAs, and so on.

The microscopic optical element as described above is kept in optically close contact with the surface of the substrate of the semiconductor device, whereby the semiconductor substrate itself is used as a part of the solid immersion lens. In a back surface analysis of the semiconductor device with the solid immersion lens, when the focus of the objective lens is matched with the integrated circuit formed on the front surface of the semiconductor substrate, the effect of the solid immersion lens enables a beam with a high NA to pass in the substrate, and the apparatus is expected to achieve a high resolution.

The lens shape of the solid immersion lens 206 as described above is determined depending upon conditions for elimination of aberration. In the case of the solid immersion lens 206 having the hemispherical shape, the focus thereof is at the center of the sphere. In this case, the numerical aperture (NA) and magnification both are multiplied by n. The shape of the solid immersion lens 206 does not have to be limited to the hemispherical shape, but may be, for example, the Weierstrass shape.

The solid immersion lens holder 208A is one suitably holding the solid immersion lens 206 relative to the objective lens 221 and is attached through an objective lens socket 209 to the objective lens 221. This solid immersion lens holder 208A will be described later in detail. The objective lens socket 209 is provided at the end portion of the objective lens 221 and is used for mounting the solid immersion lens holder 208A on the objective lens 221. In a state in which the solid immersion lens holder 208A is mounted on the objective lens 221, the objective lens socket 209 is arranged to pass light inside thereof so as to permit observation of the semiconductor device 211.

The control part B is provided with a camera controller 231, a laser scan (LSM) controller 232, and a peripheral controller 233. The camera controller 231 and LSM controller 232 control respective operations of the high-sensitivity camera 203 and the LSM unit 204, thereby controlling execution of observation of the semiconductor device 211 (acquisition of an image), setting of observation conditions, etc. performed in the observation part A.

The peripheral controller 233 controls the operation of the XYZ stage 207, thereby controlling movement, positioning, focusing, etc. of the high-sensitivity camera 203, LSM unit 204, optical system 220, etc. to positions corresponding to the observation position of the semiconductor device 211. In addition, the peripheral controller 233 drives a motor 225 for adjustment of the correction ring attached to the objective lens 221, so as to adjust the correction ring 224.

The analysis part C is provided with an image analyzer 241 and an instructor 242 and is constructed of a computer. The image analyzer 241 executes analysis processes and others necessary for image information from the camera controller 231 and from the LSM controller 232, and the instructor 242 refers to an entry entered by an operator, analysis contents by the image analyzer 241, etc. to give necessary instructions about execution of inspection of the semiconductor device 211 in the observation part A, through the control part B. An image, data, or the like acquired or analyzed by the analysis part C is displayed on a display unit 243 connected to the analysis part C, according to need.

Next, the solid immersion lens holder 208A, which is the feature of the present embodiment, will be detailed in particular. In the description below, the side of objective lens 221 relative to the solid immersion lens 206 will be referred to as the upper side and the side of sample 210 as the lower side, for simplification of description.

Figure 24:
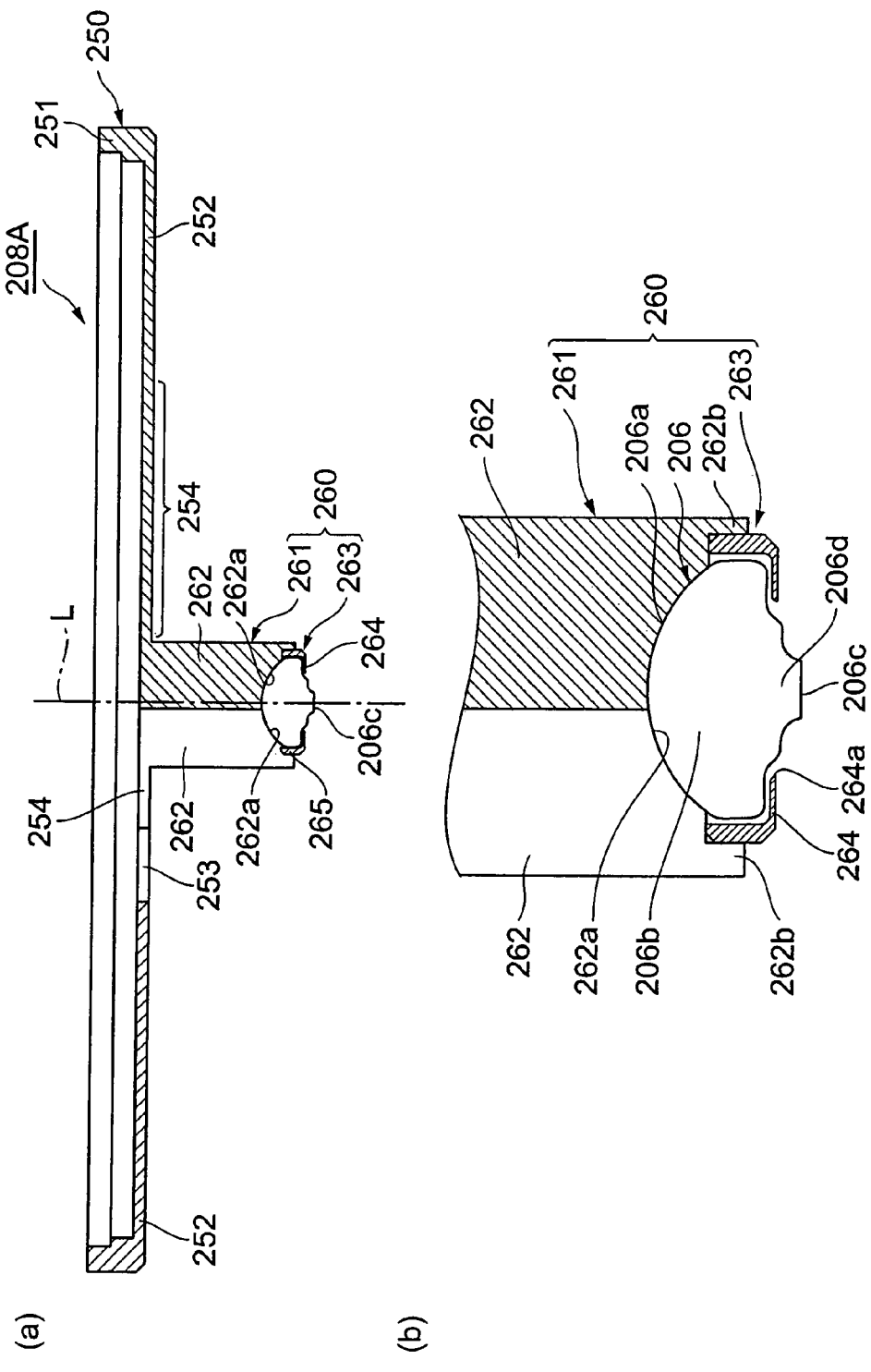
FIG. 24 is a sectional view along line IV-IV in FIG. 23.

As shown in FIGS. 23 and 24, the solid immersion lens holder 208A is constructed so that a lens holding part 260 extends from a center of a base part 250 of disk shape and in a direction substantially perpendicular to the base part 250, and the outer shape thereof is of substantially. T-shape, when viewed from a direction of arrow A1 in FIG. 23.

The base part 250 has a peripheral wall 251 for screwing with the objective lens socket 209 (cf. FIG. 22) and the base part 250 is engaged with the objective lens socket 209 to mount the solid immersion lens holder 208A so that the center of the base part 250 is located on the optical axis L of the objective lens 221. This results in permitting the position of the solid immersion lens 206 held by the solid immersion lens holder 208A to be adjusted through driving of the XYZ stage 207. The outer surface of the peripheral wall 251 is knurled so as to facilitate mounting of the base part 250 on the objective lens socket 209.

A bottom plate 252 of the base part 250 has three apertures 253, 253, 253 as light passing portions for letting a light beam pass. Each aperture 253 passes the light from the LSM unit 204 toward the solid immersion lens 206 and passes the light reflected by the semiconductor device 211 and emerging from the solid immersion lens 206, toward the objective lens 221.

Each aperture 253 is approximately sector-shaped and the apertures 253 are arranged concentrically with each other with respect to the center of the base part 250 and at equal intervals in the circumferential direction. This results in forming three connecting parts 254, 254, 254 for connecting the lens holding part 260 to the bottom plate 252, at equal intervals between adjacent apertures 253, 253. In other words, the base part 250 has the connecting parts 254, 254, 254 traversing a circular aperture formed concentrically with the center of the bottom plate 252 and connecting the bottom plate 252 to the lens holding part 260. The three connecting parts 254, 254, 254 radially extend from the center of the base part 250.

The lens holding part 260 has a holding member 261 extending from the intersecting part among the connecting parts 254, 254, 254 and in a direction substantially perpendicular to the base part 250. The holding member 261 is comprised of three holding pieces 262, 262, 262 located on the respective connecting parts 254, 254, 254 and serving as lens receivers for receiving the solid immersion lens 206.

The holding pieces 262, 262, 262 are radially arranged with respect to the center line of the holding member 261 (more specifically, in the Y-shape) and each holding piece 262 has a tapered shape the width d of which decreases toward the center line of the holding member 261 (in other words, toward the inside). This can achieve more reduction in the quantity of light blocked by the holding piece 262 among the light entering or leaving the upper surface 206a of the solid immersion lens 206. The length of the holding piece 262 in the direction of the optical axis L is longer than the depth of the recess 213 of the sample 210 (the length in the direction of the optical axis L). This permits the apparatus to observe the semiconductor device 211 located on the lower surface of the recess 213 of the sample 210, in a state in which the solid immersion lens holder 208A holds the solid immersion lens 206.

The holding pieces 262, 262, 262 and the base part 250 are integrally formed, for example, with a resin so that the center line of the holding member 261 passes the center of the base part 250. This matches the optical axis L of the objective lens 221 with the center line of the holding member 261. For this reason, the center line of the holding member 261 will also be denoted by symbol L in the description hereinafter.

The holding pieces 262, 262, 262 have their respective lens receiving surfaces 262a, 262a, 262a formed at the end portion thereof (i.e., at the end on the opposite side to the base part 250) and having a curvature equal to that of the upper surface 206a of the solid immersion lens 206, and the holding member 261 receives the solid immersion lens 206 by the three lens receiving surfaces 262a. This permits the holding member 261 to stably receive the solid immersion lens 206. In addition, a claw 262b for fixing a lens cover 263 of cylindrical shape is formed at the end portion of each holding piece 262, 262, 262.

The lens cover 263 has a bottom plate 264, and the peripheral part of the bottom plate 264 is provided with a peripheral wall 265 to be engaged with the claws 262b. The inner diameter of the peripheral wall 265 is larger than the outer diameter of the solid immersion lens 206. The bottom plate 264 has an opening 264a for letting the bottom surface 206c of the solid immersion lens 206 project to the outside (toward the sample 210), and the diameter of this opening 264a (cf. FIG. 24(b)) is larger than the outer diameter of the bottom surface 206c part in the solid immersion lens 206.

In this configuration, after the solid immersion lens 206 is placed between the lens receiving surfaces 262a and the lens cover 263, the lens cover 263 is fixed to the holding member 261 with an adhesive or the like, whereby the solid immersion lens 206 is housed in a state in which the bottom surface 206c projects out of the opening 264a, between the lens receiving surfaces 262a and the lens cover 263. This prevents the solid immersion lens 206 from slipping off the lens holding part 260.

In a state in which the lens cover 263 is fixed to the holding member 261, the space for housing of the solid immersion lens 206 created by the bottom plate 264 and the three lens receiving surfaces 262a is larger than the hemispherical part 206b of the solid immersion lens 206. Therefore, the lens holding part 260 has a play relative to the solid immersion lens 206 and, in other words, has a clearance (space).

For this reason, during observation of the semiconductor device 211, the solid immersion lens 206 can swing so that the solid immersion lens 206 follows the surface shape of the semiconductor device 211; for example, the semiconductor device 211 can be observed even in a case where the semiconductor device 211 is inclined relative to the optical axis L. Furthermore, the degree of close contact is improved between the solid immersion lens 206 and the semiconductor device 211. In addition, even if the solid immersion lens 206 swings in this manner, the position of observation with the solid immersion lens 206 agrees with the center of the sphere, so as not to affect the observation.

The following will describe an example of a method of acquiring an image of the semiconductor device 211 with the semiconductor inspection apparatus 201.

First, a position for observation of the semiconductor device 211 with the solid immersion lens 206 is specified using an objective lens 221 without the solid immersion lens 206, out of the plurality of objective lenses 221 in the microscope 205. This operation of specifying the observation position is carried out by driving the XYZ stage 207 through the peripheral controller 233 by the instructor 242.

After the specifying operation of the observation position, the objective lens is switched to an objective lens 221 with the solid immersion lens holder 208A and observation is carried out therewith. On this occasion, the instructor 242 adjusts the correction ring 224 to an appropriate position by driving the correction ring adjustment motor 225 through the peripheral controller 233 in accordance with the characteristics of the solid immersion lens 206 held by the solid immersion lens holder 208A (the thickness of the solid immersion lens 206, the refractive index thereof, etc.), the thickness of the substrate of the semiconductor device 211, the material of the substrate, and so on.

The instructor 242 drives the XYZ stage 207 through the peripheral controller 233 in accordance with the characteristics of the solid immersion lens 206 and others to press the solid immersion lens 206 against the semiconductor device 211 to achieve close contact. The instructor 242 also drives the XYZ stage 207 through the peripheral controller 233 to bring the objective lens 221 in focus. When the solid immersion lens 206 is in close contact with the semiconductor device 211 in this manner, the solid immersion lens 206 is pushed toward the lens receiving surface 262a side by the semiconductor device 211, and thus the upper surface 206a comes into contact with the lens receiving surfaces 262a (cf. FIG. 24(b)).

In the in-focus state of the objective lens 221, the instructor 242 then executes observation of the semiconductor device 211 by use of the LSM unit 204, high-sensitivity camera 203, etc. through the LSM controller 232 and the camera controller 231.

In this observation, the infrared laser beam outputted from the LSM unit 204 is outputted through the objective lens 221 and toward the sample 210. The light outputted from the objective lens 221 passes through the apertures 253 of the base part 250, enters the solid immersion lens 206 from the upper surface 206a thereof, and is outputted toward the semiconductor device 211. Then light (reflected light) reflected from the semiconductor device 211 under irradiation with the infrared laser beam is again incident to the solid immersion lens 206 and is outputted from the upper surface 206a of the solid immersion lens 206. More specifically, the reflected light from the semiconductor device 211 is outputted from the portions of the upper surface 206a not contacting the lens receiving surfaces 262a.

The reflected light emerging from this solid immersion lens 206 propagates through a region outside the lens holding part 260 (including the space between adjacent holding pieces 262) toward the base part 250. Then the light travels through the apertures 253 of the base part 250 to enter the objective lens 221. The reflected light entering the objective lens 221 is guided to the high-sensitivity camera 203 by the camera optical system 222, and the high-sensitivity camera 203 acquires an image of the circuit pattern of the semiconductor device 211 or the like. In this semiconductor inspection apparatus 201, the solid immersion lens 206 can be replaced by changing the solid immersion lens holder 208A with another. In this case, the lens replacement is easy because there is no need for directly handling the small solid immersion lens 206.

Since the whole solid immersion lens holder 208A is changed with another during the lens replacement as described above, it is preferable to form a notch or the like as a mark for discriminating the solid immersion lens 206 held by the lens holding part 260, in the holding pieces 262 of the holding member 261. This permits the operator to readily know the characteristics of the solid immersion lens 206 (refractive index, thickness, etc.) held by the solid immersion lens holder 208A, by only a look at the solid immersion lens holder 208A. Other marks for discriminating the solid immersion lens 206 can be, for example, different colors for the lens holding part 260.

For inspecting the semiconductor device 211 of the sample 210 with use of the semiconductor inspection apparatus 201, as described above, it is important for the lens holding part 260 of the solid immersion lens holder 208A to extend in the direction of the optical axis L of the objective lens 221 (in the direction approximately perpendicular to the base part 250) and for the solid immersion lens holder 208A to have the approximately T-shape.

Namely, since the lens holding part 260 extends in the direction of the optical axis L of the objective lens 221, the lens holding part 260 is approximately parallel to the side wall 213a of the recess 213 (cf. FIG. 22). For this reason, the lens holding part 260 is unlikely to interfere (in other words, contact) with the side wall 213a of the recess 213 even if the solid immersion lens 206 is moved to near the peripheral part of the semiconductor device 211 provided on the lower surface of the recess 213. As a result, the observation can be conducted while the solid immersion lens 206 is located closer to the peripheral part 211a of the semiconductor device 211 positioned in the recess 213. In order to allow the lens holding part 260 to be located closer to the vicinity of the side wall 213a of the recess 213, the outside diameter of the lens holding part 260 is preferably slightly larger than the outside diameter of the solid immersion lens 206.

In the solid immersion lens holder 208A, since the upper surface 206a of the solid immersion lens 206 is partly received by the three holding pieces 262 radially arranged with respect to the center line L of the holding member 261, light can be securely inputted or outputted from the portions out of contact with the holding pieces 262 in the upper surface 206a of the solid immersion lens 206 even if the lens holding part 260 extending in the direction of the optical axis L holds the solid immersion lens 206.

Since the base part 250 has the apertures 253, the light (infrared laser beam) from the LSM unit 204 can be guided well into the solid immersion lens 206 and the light from the solid immersion lens 206 can also be guided well into the objective lens 221 even if the solid immersion lens holder 208A is mounted on the objective lens 221.

Furthermore, since the solid immersion lens holder 208A is mounted on the objective lens 221, the position of the solid immersion lens 206 can be adjusted by moving the objective lens 221 by the XYZ stage 207. For observing the semiconductor device 211, the objective lens 221 is moved in the direction of the optical axis L of the objective lens 221, whereby the solid immersion lens 206 is brought into close contact with the semiconductor device 211. Therefore, for example, even in a case where the solid immersion lens holder 208A is applied to an inverted microscope, as well as the erecting microscope 205 as shown in FIG. 21, the solid immersion lens 206 can be securely kept in close contact with the semiconductor device 211.

Second Embodiment

Figure 25:
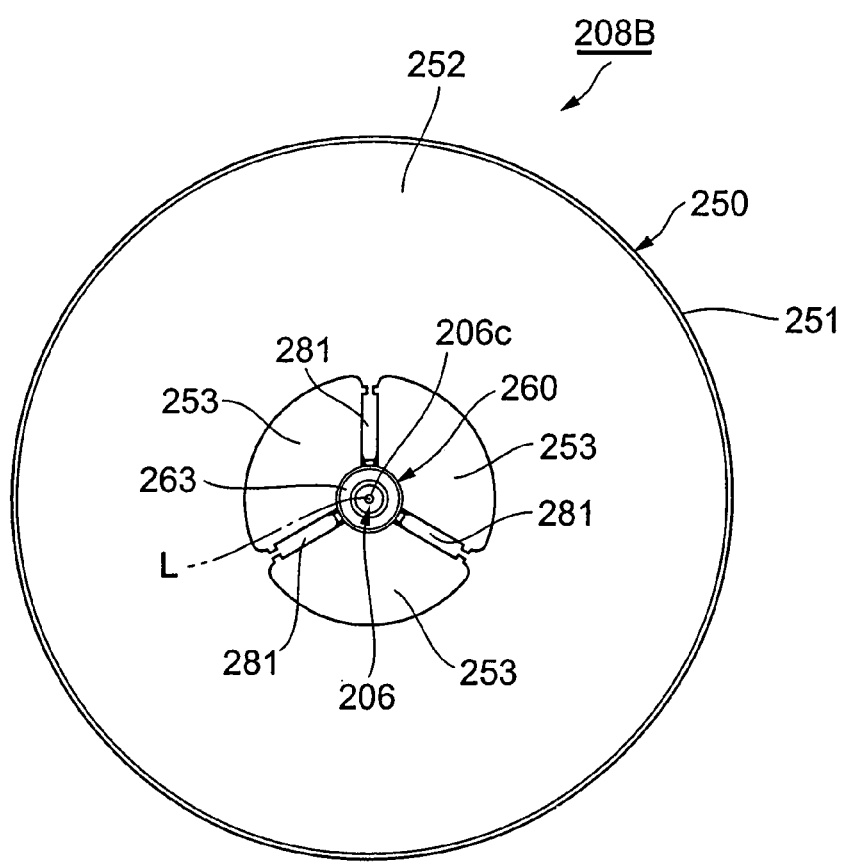
FIG. 25 is a bottom view of the solid immersion lens holder according to the second embodiment.

FIG. 25 is a bottom view of solid immersion lens holder 208B according to the second embodiment. FIG. 25 shows a state in which the solid immersion lens holder 208B holds a solid immersion lens 206.

The configuration of the solid immersion lens holder 208B is different from the configuration of the solid immersion lens holder 208A shown in FIG. 23, in that the width of connecting parts 281, 281, 281 is narrowed in part in the extending direction of each connecting part 281 (i.e., in the radial directions of the base part 250). The solid immersion lens holder 208B will be described with focus on this point.

Since the width of the connecting parts 281 is narrowed in part, the connecting parts 281 will be broken if a predetermined stress is exerted through the solid immersion lens 206 or the like on the holding member 261.

Since the solid immersion lens 206 has to be brought into close contact with the semiconductor device 211 in order to observe the semiconductor device 211 through the solid immersion lens 206, the solid immersion lens 206 is pressed against the semiconductor device 211. In this case, for example, if the solid immersion lens 206 is pushed too hard, the semiconductor device 211 might be damaged. This is also the case in the operation of moving the solid immersion lens 206 for scan on the semiconductor device 211.

In contrast to it, the width of the connecting parts 281 is narrowed in part in the configuration of the solid immersion lens holder 208B, and when the solid immersion lens 206 is pushed against the semiconductor device 211, the connecting parts 281, 281, 281 break before damage to the semiconductor device 211, so as to result in first breaking the solid immersion lens holder 208B.

Describing it in more detail, when the solid immersion lens 206 is pressed against the semiconductor device 211, the solid immersion lens 206 receives a force as reaction from the semiconductor device 211. As a result, a stress is exerted on the holding member 261 in contact with the upper surface 206a of the solid immersion lens 206, whereupon the stress is applied to the connecting parts 281 provided integrally with the holding member 261. The connecting parts 281 break when the stress exceeds a predetermined value. For this reason, the semiconductor device 211 is prevented from receiving a load over a certain level during inspection of the semiconductor device 211, whereby the semiconductor device 211 is prevented from being damaged.

Namely, the solid immersion lens holder 208B has the configuration for protecting the semiconductor device 211 as an observation object in accordance with the stress exerted on the lens holding part 260 during observation, based on the width of the connecting parts 281 narrowed in part. The width of the narrowed portions in the connecting parts 281 can be determined so that the connecting parts 281 can break before damage to the semiconductor device 211 in accordance with the stress exerted on the connecting parts 281.

The effect of the configuration wherein the holding member 261 extends in the direction of the optical axis L of the objective lens 221 is much the same as in the case of the first embodiment. Namely, since the lens holding part 260 is unlikely to contact the side wall 213a of the recess 213 (cf. FIG. 22), it becomes feasible to move the lens holding part 260 up to the vicinity of the side wall 213a of recess 213. As a result, the peripheral part 21a of the semiconductor device 211 can be observed.

The present embodiment adopted the configuration wherein the width of the connecting parts 281 was narrowed, but it is also possible to adopt, for example, a configuration wherein the thickness of connecting parts 281 (the length in the direction perpendicular to the bottom plate 252) is decreased in part.

Third Embodiment

Figure 26:
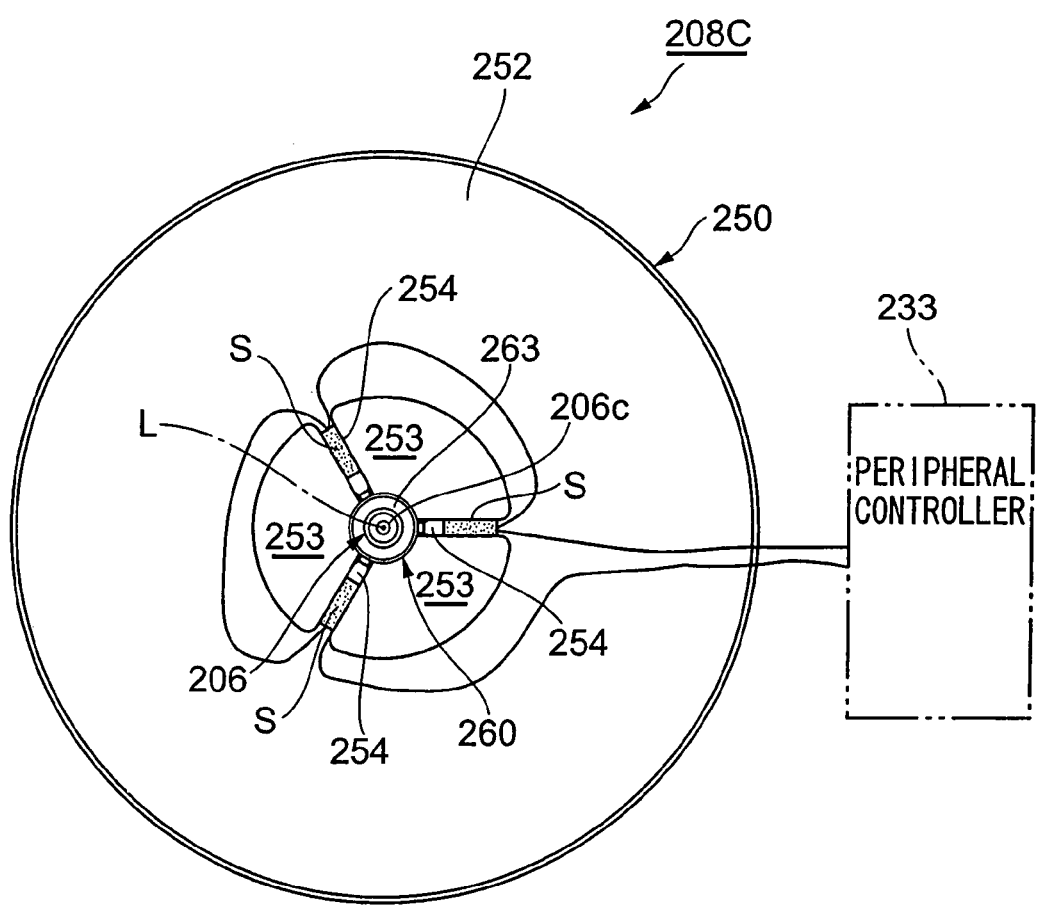
FIG. 26 is a bottom view of the solid immersion lens holder according to the third embodiment.

FIG. 26 is a bottom view of solid immersion lens holder 208C according to the third embodiment. FIG. 26 shows a state in which the solid immersion lens holder 208C holds a solid immersion lens 206.

The configuration of the solid immersion lens holder 208C is different from the configuration of the solid immersion lens holder 208A shown in FIG. 23, in that the solid immersion lens holder 208C has three stress detection sensors S, S, S. The solid immersion lens holder 208C will be described with focus on this point.

A stress detection sensor S is stuck onto each connecting part 254 and detects the stress exerted through the lens holding part 260 on the connecting part 254 during observation of the semiconductor device 211, as described in the second embodiment. The stress detection sensors S can be, for example, strain gages.

The stress detection sensors S are electrically connected through the peripheral controller 233 to the instructor 242 (cf. FIG. 21), and the instructor 242 terminates the inspection with the semiconductor inspection apparatus 201 when the stress detected by the stress detection sensors S exceeds a predetermined stress. More specifically, the instructor 242 suspends the operation of the XYZ stage 207 by the peripheral controller 233 to terminate the adjustment of the observation position, focusing, and so on.

This can suspend such operations as position adjustment of the solid immersion lens 206 before damage to the semiconductor device 211 due to pushing of the solid immersion lens 206 or the like, whereby the semiconductor device 211 can be protected, as in the case of the second embodiment. Namely, the solid immersion lens holder 208C has the configuration for protecting the semiconductor device 211 as an observation object, thanks to the possession of the stress detection sensors S.

The effect of the configuration wherein the lens holding part 260 extends in the direction of the optical axis L of the objective lens 221 is much the same as in the case of the first embodiment. There are no particular restrictions on the setting locations of the stress detection sensors S as long as they can detect the stress exerted on the lens holding part 260.

Fourth Embodiment

Figure 27:
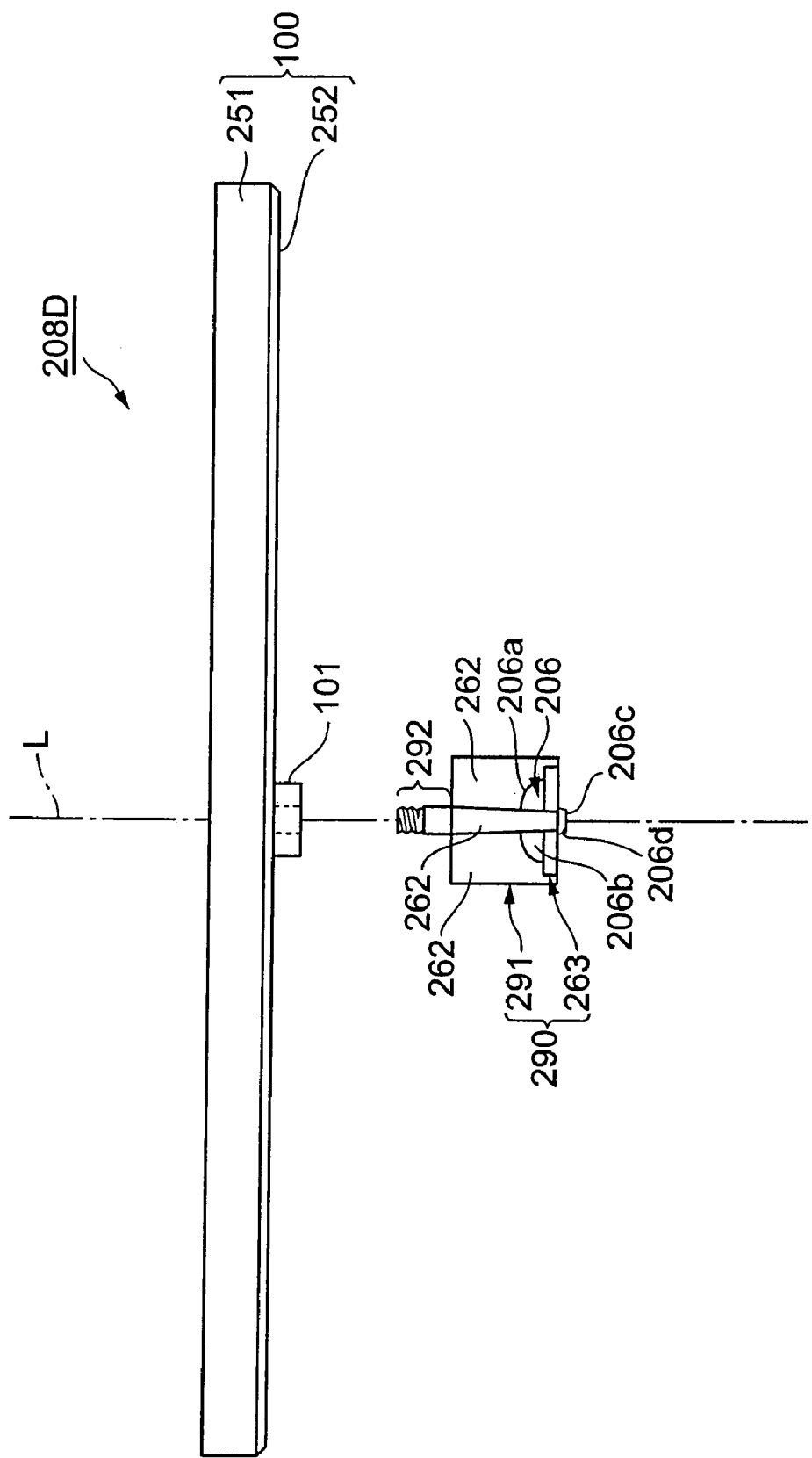
FIG. 27 is an exploded side view of the solid immersion lens holder according to the fourth embodiment.

FIG. 27 is an exploded side view of solid immersion lens holder 208D according to the fourth embodiment. FIG. 27 shows a state in which the solid immersion lens holder 208D holds a solid immersion lens 206.

The configuration of solid immersion lens holder 208D is mainly different from the configuration of the solid immersion lens holder 208A shown in FIG. 23, in that the lens holding part 290 is detachably attached through the bottom plate 252 of the base part 100 to the base part 100. The solid immersion lens holder 208D will be described with focus on this point.

The holding member 291 forming the lens holding part 290 has a projection 292 on the bottom plate 252 side of the base part 100. The bottom plate 252 has a boss 101 to engage with the projection 292, at the intersection among the three connecting parts 254, 254, 254 (cf. FIG. 23). In the solid immersion lens holder 208D, therefore, the lens holding part 290 can be connected to the base part 100 through engagement of the projection 292 with the boss 101.

In this configuration the lens holding part 290 can be attached to and detached from the base part 100, whereby the solid immersion lens 206 can be readily changed in a state in which the base part 100 is mounted through the objective lens socket 209 on the objective lens 221.

The holding member 291 extends in the direction of the optical axis L as the holding member 261 shown in FIG. 23 does, and the effect of the configuration wherein the holding member 291 extends in the direction of the optical axis L is much the same as in the case of the first embodiment; it is feasible to observe the object up to a region closer to the peripheral part 211a of the semiconductor device 211.

Fifth Embodiment

Figure 28:
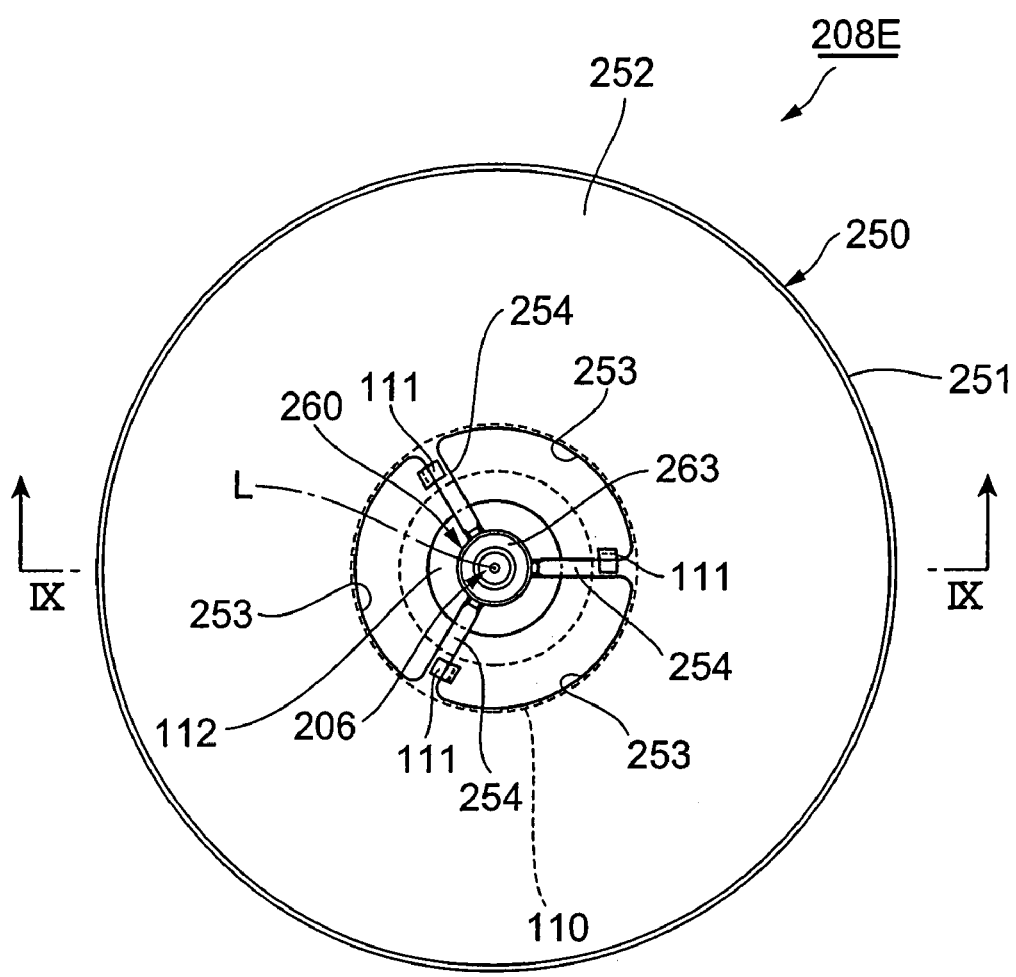
FIG. 28 is a bottom view of the solid immersion lens holder according to the fifth embodiment.
Figure 29:
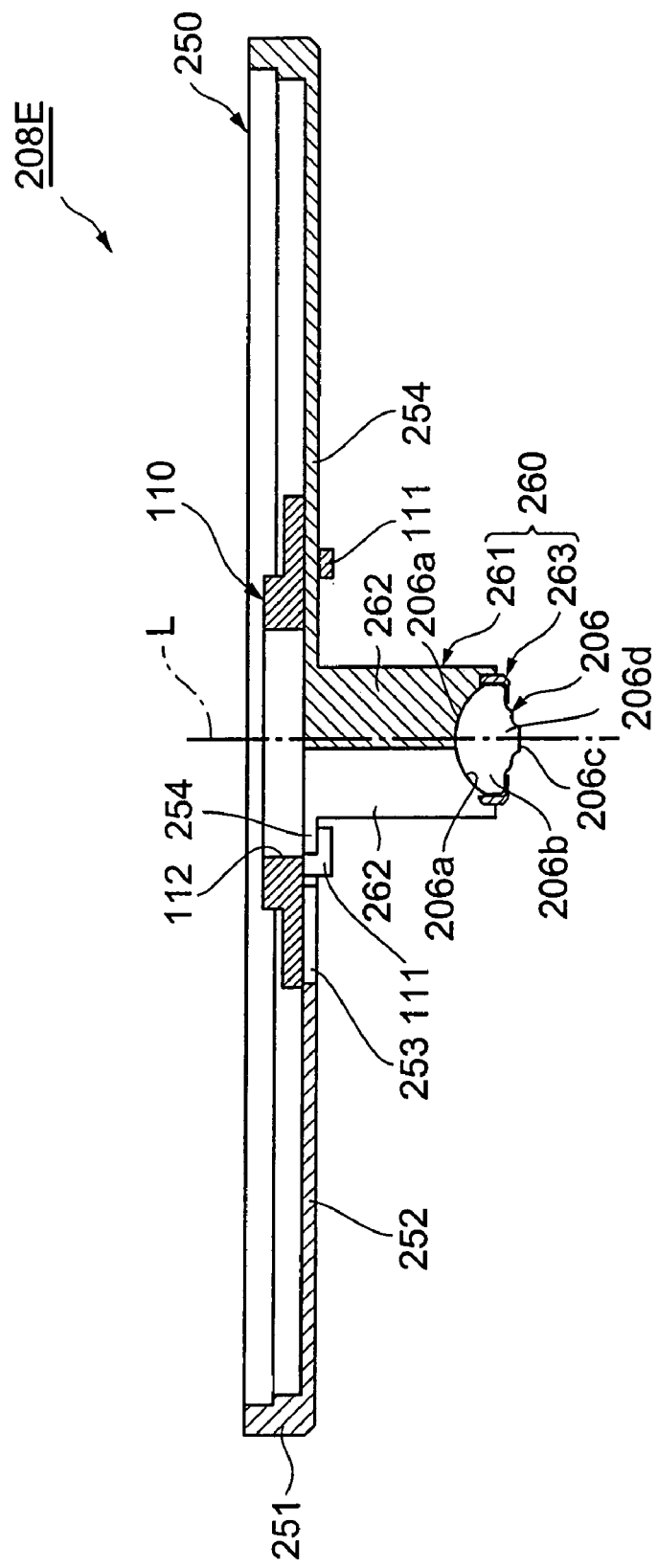
FIG. 29 is a sectional view along line IX-IX in FIG. 28.

FIG. 28 is a bottom view of solid immersion lens holder 208E according to the fifth embodiment. FIG. 29 is a sectional view along line IX-IX in FIG. 28. FIGS. 28 and 29 show a state in which the solid immersion lens holder 208E holds a solid immersion lens 206.

The configuration of the solid immersion lens holder 208E is different from the configuration of the solid immersion lens holder 208A shown in FIG. 23, in that the solid immersion lens holder 208E has a diaphragm 110 for limiting a light beam passing the base part 250. The solid immersion lens holder 208E will be described with focus on this point.

The outer shape of the diaphragm 110 is of a disk shape and is attached to the base part 250 by engaging three hooks 111, 111, 111 of approximately L-shape provided on the bottom surface of the diaphragm 110 (the surface on the base part 250 side), with corresponding connecting parts 254, 254, 254. The diaphragm 110 is arranged concentrically with the center of the base part 250 and is located on the upper surface side of the bottom plate 252. The diaphragm 110 restricts the beam passing through the apertures 253 of the base part 250, by a circular aperture 112 formed in the central region thereof.

Since the diaphragm 110 is attached to the base part 250 by engaging the hooks 111 with the connecting parts 254 as described above, it is attachable to and detachable from the base part 250. For this reason, by preparing a plurality of diaphragms 110 with different sizes of aperture 112, it is feasible to adjust the size of the beam passing the base part 250. By adjusting the size of the aperture 112 of the diaphragm 110 in this manner, the NA of the beam incident to the semiconductor device 211 can be varied, so that the semiconductor device 211 can be observed with any desired NA.

In the semiconductor device, for example, where a plurality of layers with different refractive indices are stacked between the surface in contact with the solid immersion lens 206 and the observation position through the solid immersion lens 206, total reflection can occur between layers, depending upon the NA of the beam incident to the semiconductor device, and the light can fail to adequately arrive at the desired observation position. In addition, the totally reflected light can pass through the solid immersion lens 206 and objective lens 221 to enter the high-sensitivity camera 203, so as to degrade the image.

In contrast to it, the present embodiment is configured to adjust the NA of the beam incident to the semiconductor device 211 by the diaphragm 110 as described above, whereby the light can securely arrive at the desired observation position, without occurrence of total reflection between layers. In this case, the totally reflected light between layers is prevented from again entering the objective lens 221 through the solid immersion lens 206, whereby the semiconductor device 211 can be observed as a sharper image. It is also possible to provide a liquid crystal diaphragm instead of the diaphragm 110.

The effect of the configuration wherein the lens holding part 260 extends in the direction of the optical axis L is much the same as in the case of the first embodiment, and it is feasible to observe the object up to a region closer to the peripheral part 211a of the semiconductor device 211.

Sixth Embodiment

Figure 30:
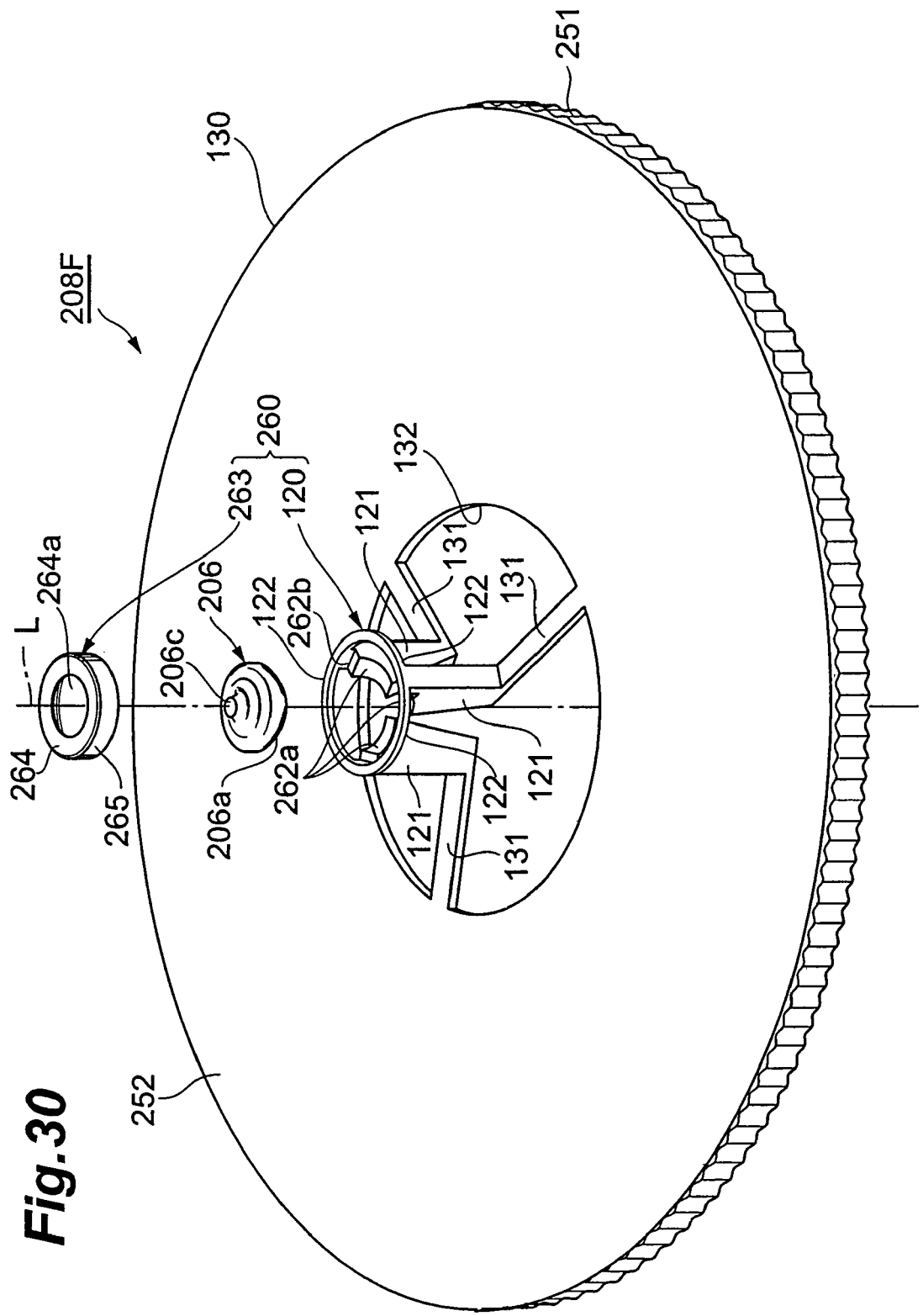
FIG. 30 is an exploded perspective view of the solid immersion lens holder according to the sixth embodiment.

FIG. 30 is an exploded perspective view of solid immersion lens holder 208F according to the sixth embodiment. FIG. 30 shows a case in which the solid immersion lens holder 208F holds a solid immersion lens 206.

The configuration of the solid immersion lens holder 208F is mainly different from the configuration of the solid immersion lens holder 208A shown in FIG. 23, in that three holding pieces 121, 121, 121 of holding member 120 are arranged apart from the center line L of the holding member 120. The solid immersion lens holder 208F will be described with focus on this point.

Each holding piece 121 is radially arranged with respect to the center line L of the holding member 120 passing the center of the base part 130 and is located an equal distance apart from the center line L. Each holding piece 121 extends from an end of each connecting part 131 and in a direction substantially perpendicular to the base part 130 (i.e., in the direction of the optical axis L). The holding pieces 121 adjacent to each other are coupled by a connecting member 122 of arcuate shape integrally formed with the holding pieces 121. For this reason, the positional relation among three holding pieces 121, 121, 121 is securely fixed. Each holding piece 121 has a lens receiving surface 262a and a claw 262b at the end portion thereof as the holding piece 262 shown in FIG. 23 did.

In this configuration, the three holding pieces 121 are not connected on the center line L and the connecting parts 131 do not intersect at the center of the bottom plate 252 (the center of the base part 130) in the base part 130, either. For this reason, the three apertures 253 shown in FIG. 23 are communicated with each other at the center of the bottom plate 252 (the center of the base part 130) to form one aperture. In other words, the solid immersion lens holder 208F has a circular aperture 132 formed as centered on the center of the bottom plate 252, and is configured so that the bottom plate 252 is coupled to the ends of the holding pieces 121 located in the aperture 132, by the connecting parts 131 extending from the peripheral part of the aperture 132 toward the center and shorter than the radius of the aperture 132.

In the solid immersion lens holder 208F having the configuration as described above, the light entering and leaving the upper surface 206a of the solid immersion lens 206 is further prevented from being blocked by the holding pieces 121, whereby the light beam can be effectively utilized. Since the light can pass the center and surroundings of the base part 130 and through the interior of the holding member 120, more image information can be acquired from the semiconductor device 211.

Since the light is also allowed to pass the region near the center line L of the lens holding part 260 in the solid immersion lens holder 208F as described above, it is preferable to adopt the configuration wherein the holding pieces 121 are formed so that the distance from the center line L to each holding piece 121 decreases from the base part 130 side toward the solid immersion lens 206 side, as shown in FIG. 30, in terms of effective utilization of the beam.

The present embodiment adopted the configuration wherein the holding pieces 121 adjacent to each other were coupled by the connecting member 122, but it is also possible to adopt a configuration without the connecting member 122, because the holding pieces 121 adjacent to each other are also coupled by the lens cover 263 fixed to the claws 262b formed in the holding pieces 121.

The effect of the configuration wherein the lens holding part 260 having the holding member 120 and lens cover 263 extends in the direction of the optical axis L is much the same as in the case of the first embodiment, and it is feasible to observe the object up to a region closer to the peripheral part 211a of the semiconductor device 211.

Seventh Embodiment

Figure 31:
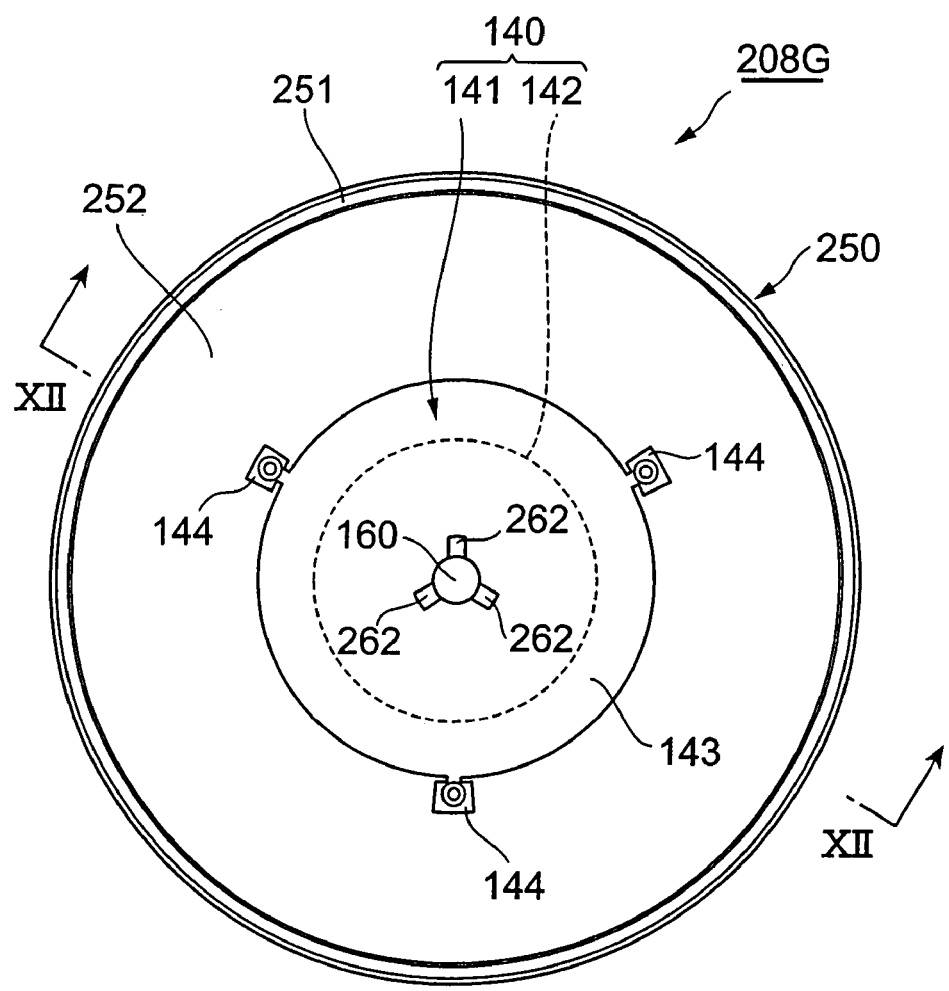
FIG. 31 is a view of the solid immersion lens holder of the seventh embodiment from the objective lens side.
Figure 32:
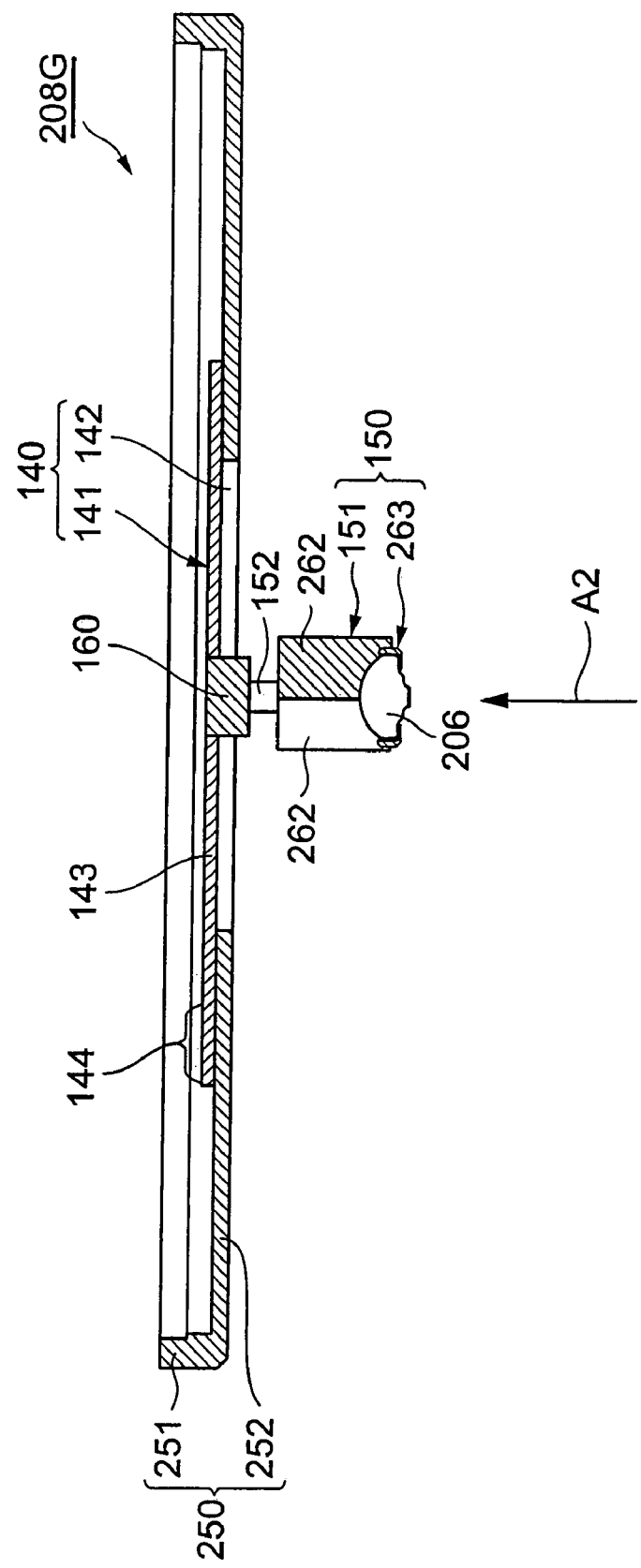
FIG. 32 is a sectional view along line XII-XII in FIG. 31.
Figure 33:
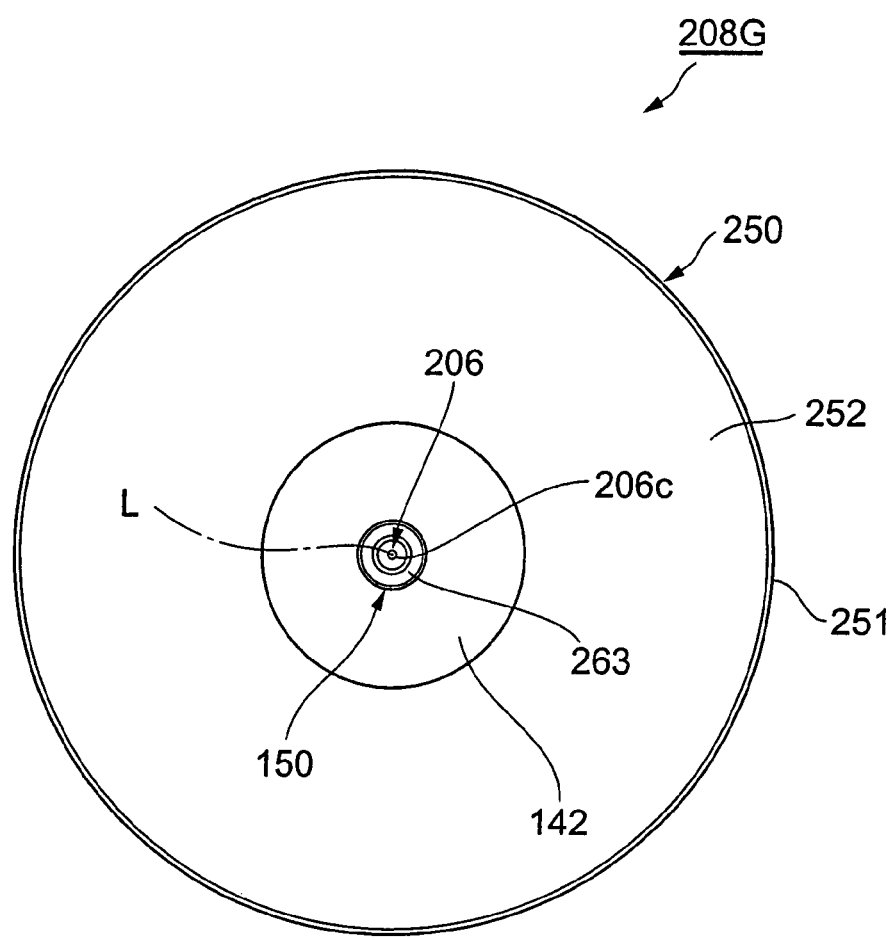
FIG. 33 is a view of the solid immersion lens holder shown in FIG. 32 from a direction of arrow A2 in FIG. 32.

FIG. 31 is a view of solid immersion lens holder 208G according to the seventh embodiment, from the side of objective lens 221. FIG. 32 is a sectional view along line XII-XII in FIG. 31. FIG. 33 is a view of the solid immersion lens holder 208G from a direction of arrow A2 in FIG. 32. FIGS. 31 to 33 show a state in which the solid immersion lens holder 208G holds a solid immersion lens 206.

The configuration of the solid immersion lens holder 208G is mainly different from the configuration of the solid immersion lens holder 208A shown in FIG. 23, in that the light passing portion 140 of the solid immersion lens holder 208G has a glass plate 141 as a light passing member. The solid immersion lens holder 208G will be described with focus on this point.

The light passing portion 140 is comprised of a circular aperture 142 formed concentrically with the center of the base part 250, and a glass plate 141 provided on the upper surface of the base part 250. The glass plate 141 has a glass plate body 143 of disk shape, and mount pieces 144 projecting in radial directions from the peripheral part of the glass plate body 143. The diameter of the glass plate body 143 of the glass plate 141 is larger than the diameter of the aperture 142. For this reason, when the glass plate 141 is placed so as to cover the aperture 142, the mount pieces 144 are located on the bottom plate 252 of the base part 250.

The glass plate 141 is fixed through the mount pieces 144 so that the center of the base part 250 is located on the center line L of the holding member 151. The width of the mount pieces 144 is narrowed in connecting part to the glass plate body 143.

A mount portion 160 of cylindrical shape to engage with a projection 152 of the holding member 151 of the lens holding part 150 is buried in the center of the glass plate 141. By engaging this mount portion 160 with the projection 152, the lens holding part 150 is attached to the glass plate 141. The relation of the mount portion 160 with the holding member 151 having the projection 152 is similar to the relation of the boss 101 with the holding member 291 of the solid immersion lens holder 208D in the fourth embodiment.

In the configuration of this solid immersion lens holder 208G the base part 250 and the lens holding part 150 are attachable to and detachable from each other, and thus the solid immersion lens 206 can be readily replaced with another even in a state in which the base part 250 is fixed to the objective lens 221.

Since the width of the mount pieces 144 is narrowed on the glass plate body 143 side, the glass plate 141 will break before damage to the semiconductor device 211 during position adjustment of the solid immersion lens 206, focusing, or the like, for the same reason as in the case of the solid immersion lens holder 208D shown in FIG. 25. As a result, the semiconductor device 211 is protected.

Furthermore, the aperture 142 can pass the beam in the region except for the mount portion 160 in the base part 250, whereby the blocking of the beam from the solid immersion lens 206 is further suppressed. As a result, the image of the semiconductor device 211 can be formed by more effectively utilizing the beam from the solid immersion lens 206.

The present embodiment adopts the configuration wherein the glass plate 141 is located on the objective lens 221 side of the base part 250, but it is also possible to adopt, for example, a configuration wherein the glass plate 141 has substantially the same shape as the aperture 142 and is fitted in the aperture 142. The lens holding part 150 was described to be detachable from and attachable to the base part 250 through the mount portion 160, but it may be arranged in a state in which it is always fixed to the base part 250. Each holding piece 262 may be buried directly in the glass plate 141.

The effect of the configuration wherein the lens holding part 150 extends in the direction of the optical axis L is much the same as in the case of the first embodiment, and it is thus feasible to observe the object up to a region closer to the peripheral part 211a of the semiconductor device 211.

The preferred embodiments of the present invention were described above, but it is noted that the present invention is by no means limited to the above embodiments. The configurations of the solid immersion lens holders 208A-208G according to the first to seventh embodiments can also be used in combination.

For example, the solid immersion lens holders 208D-208F according to the fourth to sixth embodiments may be configured so as to protect the observation object by narrowing the width of the connecting parts in part in each of them or by sticking the stress detection sensors onto the respective connecting parts. Furthermore, the solid immersion lens holders 208B-208C, 208E, 208F may be configured so that the lens holding part is detachably attached to the base part, as the solid immersion lens holder 208D is. In a further preferred configuration, the solid immersion lens holders 208B-208D, 208F, 208G are configured to have the diaphragm 110 as the solid immersion lens holder 208E is.

Each of the holding members 261, 291, 120, and 151 is comprised of the three holding pieces 262, 121, but there are no particular restrictions on the number of holding pieces 262, 121 as long as the solid immersion lens 206 can be stably received. Furthermore, where each of the solid immersion lens holders 208A-208G of the first to seventh embodiments was applied to the semiconductor inspection apparatus 201, the center line of the lens holding part 260, 290, 150 was arranged to agree with the optical axis L of the objective lens 221; however, they do not always have to agree with each other. In a potential configuration, the lens holding part 260, 290, 150 extends in the direction of the optical axis L and, for example, the center line of the lens holding part 260, 290 150 may be parallel to the optical axis L.

Furthermore, the first to seventh embodiments adopted the holding pieces as lens receivers, but the lens receivers are not limited to the platelike members. The solid immersion lens holders 208A-208G of the first to seventh embodiments are also suitably applicable, for example, to systems for observing objects like wafers. Furthermore, the solid immersion lens holders 208A-208G of the first to seventh embodiments were applied to the semiconductor inspection apparatus 201, but they are also applicable to systems for observing objects except for semiconductors.

Further, in the above-described microscope and sample observation method, it is also preferable that the focusing in the normal mode, used for observing the normal image of the sample, is carried out by using an automatic focusing technique for automatically controlling the focal point. The automatic focusing can be carried out, for example, by utilizing the contrast in the image.

For example, when the images of the sample are acquired at a plurality of positions different from each other in the Z-axis direction, the contrast of the image becomes larger as the focal point is matched. Accordingly, the focal point can be determined by the position with the largest image contrast among the above plurality of positions. As for the contrast of the image, for example, when the luminance profile of the image is considered as a profile surface having a three-dimensional shape corresponding to the luminance variation in the image, the contrast value can be evaluated by using a surface area of the profile surface.

An example of the focusing method by using the above automatic focusing technique is as follows. First, an image of the sample is acquired through the objective lens, and a contrast value of the obtained image (e.g. a surface area of the luminance profile) is extracted. Then, the stage carrying the sample is moved in the Z-axis direction by a predetermined distance, and again the acquisition of the image and the extraction of the contrast value are carried out. Further, the above operations are repeatedly performed. Here, as for the above-described distance in the Z-axis direction for moving the stage carrying the sample, it is preferable that the distance is set based on the resolution and the like in the Z-axis direction.

In the above operations, if the contrast value is increased twice in a row, or the contrast value is increased once and then decreased once, the operations of moving the stage, the acquisition of the image, and the extraction of the contrast value are repeatedly carried out. On the other hand, if the contrast value is decreased twice in a row, the position before the decrease of the contrast value is determined as the focal point. As for the specific focusing method, various methods can be used in addition to the above-described method.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A microscope for observing a sample at a predetermined observation plane, comprising:
    an optical system comprising an objective lens and adapted to guide an image of the sample;
    objective lens driving means for driving the objective lens to achieve aberration correction for the sample;
    a solid immersion lens arranged at a position including an optical axis from the sample to the optical system; and
    controlling means for controlling the objective lens driving means,
    wherein the controlling means has a solid immersion lens mode, as a control mode, in which the aberration correction is carried out by controlling the driving of the objective lens via the objective lens driving means under a correction condition set based on a refractive index $n_0$ of the sample and a thickness $t_0$ of the sample up to the observation plane, and a refractive index $n_1$, a thickness $d_1$, a radius of curvature $R_1$ of the solid immersion lens, and further based on at least a geometric aberration I2 appearing at the interface between the solid immersion lens and the sample given by $$I2 = n_1(n_0^2 - n_1^2)t_0 NA^2/(2n_0^3),$$

where NA is a numerical aperture of the objective lens,
    wherein the objective lens comprises a first lens unit and a second lens unit arranged along the optical axis, and
    wherein the objective lens driving means comprises focusing means for changing a distance between the sample and the objective lens to carry out the focusing, and aberration correcting means for changing a spacing between the first lens unit and the second lens unit in the objective lens to carry out the aberration correction.

2. The microscope according to claim 1, wherein the controlling means comprises an aberration correction table corresponding to the correction condition in the solid immersion lens mode.

3. The microscope according to claim 1, wherein the controlling means has two control modes, a normal mode in which the focusing is carried out by changing a distance between the sample and the objective lens, and the solid immersion lens mode.

4. The microscope according to claim 3, wherein in the normal mode, the focusing is carried out under a normal correction condition set based on the refractive index $n_0$ of the sample and the thickness $t_0$ of the sample up to the observation plane.

5. The microscope according to claim 4, wherein the controlling means comprises a focusing table corresponding to the normal correction condition in the normal mode, and a focusing table and an aberration correction table corresponding to the correction condition in the solid immersion lens mode.

6. The microscope according to claim 1, wherein the refractive index $n_1$ of the solid immersion lens is different from the refractive index $n_0$ of the sample.

7. The microscope according to claim 1, comprising image acquiring means for acquiring the image of the sample guided through the optical system.

8. The microscope according to claim 1, comprising analyzing means for setting optical parameters for the controlling means including the refractive index $n_0$ and the thickness $t_0$ of the sample, and the refractive index $n_1$, the thickness $d_1$, and the radius of curvature $R_1$ of the solid immersion lens.

* * * * *